(12) United States Patent
Dau et al.

(10) Patent No.: US 6,531,282 B1
(45) Date of Patent: Mar. 11, 2003

(54) MULTIPLEX AMPLIFICATION AND ANALYSIS OF SELECTED STR LOCI

(75) Inventors: Peter C. Dau, Winnetka, IL (US); Debang Liu, Wilmette, IL (US)

(73) Assignee: Oligotrail, LLC, Evanston, IL (US)

(*) Notice: Subject to any disclaimer, the term of this patent is extended or adjusted under 35 U.S.C. 154(b) by 0 days.

(21) Appl. No.: 09/580,497

(22) Filed: May 30, 2000

(51) Int. Cl.[7] .................................................. C12Q 1/68
(52) U.S. Cl. .............................. 435/6; 435/5; 435/91.1; 435/91.2; 435/810; 536/24.33; 536/23.1; 536/25.3; 536/25.32; 548/427; 436/519; 430/93; 430/580
(58) Field of Search .................. 435/5, 6, 91.1, 435/91.2, 810; 536/24.33, 23.1, 25.3, 25.32; 430/93, 581; 436/519

(56) References Cited

U.S. PATENT DOCUMENTS

| | | | |
|---|---|---|---|
| 5,599,666 A | * | 2/1997 | Schumm et al. |
| 6,013,444 A | * | 1/2000 | Dau et al. ....................... 435/6 |
| 6,090,558 A | * | 7/2000 | Butler et al. .................... 435/6 |
| 6,110,630 A | * | 8/2000 | Reddy et al. ................... 430/93 |
| 6,207,031 B1 | * | 3/2001 | Adourian et al. |
| 6,238,863 B1 | * | 5/2001 | Schumm et al. ............... 435/6 |

FOREIGN PATENT DOCUMENTS

WO    WO00/31306    2/2000

OTHER PUBLICATIONS

PE Applied Biosystems' Solutions for the CODIS Database.
Promega PowerPlex 1.2 System.

* cited by examiner

*Primary Examiner*—W. Gary Jones
*Assistant Examiner*—Janell E. Taylor
(74) *Attorney, Agent, or Firm*—Whitham, Curtis & Christofferson, P.C.

(57) ABSTRACT

The present invention provides a means to identify the alleles present in a DNA-containing sample by providing subsets of loci for amplification by multiplex PCR. The loci include the thirteen CODIS short tandem repeat (STR) loci and amelogenin. The loci within each subset are grouped so that, upon PCR amplification, the amplicons produced within a given subset do not overlap. Differential labeling of subsets makes it possible to further group the subsets into compound multiplexes for co-amplification in a single reaction vessel, and analysis in a single electrophoretic channel.

24 Claims, 43 Drawing Sheets

MULTIPLEX AMPLIFICATION AND ANALYSIS OF SELECTED STR LOCI

This invention was made using funds from grants from the National Institutes of Health having grant number 2 R44 HGO 1985-02. The government may have certain rights in this invention.

BACKGROUND OF THE INVENTION

1. Field of the Invention

The present invention is generally directed to the detection of short tandem repeat (STR) genetic markers in a genomic system. The present invention is more specifically directed to the simultaneous amplification of the thirteen specific and distinct polymorphic STR genetic loci of the Combined DNA Index System (CODIS) using the polymerase chain reaction (PCR) and the use of locus specific brackets (LSB) in electrophoretic calibration of their fragment lengths to determine in one, two or four PCR reactions and analytical channels the alleles of each locus contained within the multiplex system.

2. Background of the Invention

Due to their highly polymorphic nature, short tandem repeat (STR) loci are extremely useful as genetic markers. For example, the utilization of STRs has been fundamental to the identification and characterization of many disease genes, and to the development of such sophisticated technologies as linkage mapping and DNA genotyping.

STRs are short, tandemly repeated DNA sequences which are interspersed throughout the human genome at up to several hundred thousand loci (Koreth, et al. 1996; Fregeau, et al., 1997). They are also found in animals and plants where they are similarly useful as genetic markers (Orti, et al., 1997; Powell, et al., 1996). STRs are typically 2–7 base pairs in length. These loci are highly polymorphic with respect to the number of repeat units they contain and may vary in internal structure as well. Variation in the number of STR repeat units at a particular locus causes the length of the DNA at that locus to vary from allele to allele and from individual to individual. Thus, many allelic variants exist within the human population, and STRs provide a rich source of genetic markers.

While the alleles at a single STR locus may be the same for two different individuals in a population, especially if the individuals are genetically related, the probability that the alleles of two individuals will be identical at several different loci becomes smaller and smaller as the number of loci which are examined increases. If a sufficient number of loci are examined, the overall allelic pattern will be unique for each individual. As a result, and of particular importance in forensic analysis, by determining the alleles at a sufficiently large number of loci in two different DNA samples it is possible to establish with virtual certainty whether or not the two samples originally came from the same individual.

Characterization of the alleles at specific STR loci for purposes of individual identification usually begins with their PCR amplification from genomic DNA of the individual whose genome contains those loci. Although a particular repeat unit may be common to several different STR loci, identification of a particular STR locus may be effected via PCR amplification by utilizing primer pairs which hybridize to unique DNA sequences which flank the repeat region, i.e. unique sequences located 5' and 3' to the repeat units. Use of such unique primers makes it possible to simultaneously amplify many different STR loci in a single DNA sample, a technique referred to as multiplexing. The resulting PCR products (amplicons) from the various loci may then be separated by electrophoresis and identified by determining their lengths in comparison to known DNA standards.

While the process is in theory straightforward, several factors must be considered in order to ensure correct identification of the STR loci. For example, STR alleles are typically categorized by the number of repeat units they contain, which is convenient for entry into databases. In forensic applications, the preferred alleles are for the most part composed of regular repeat units of a size that is optimally resolved with current electrophoretic technology, usually four bases long (Edwards et al., 1991; Perez-Lezaun, et al., 1997). However, some of the tetrameric STR loci useful in forensic analysis contain non-integer alleles which differ in size by only 1 or 2 nucleotides (Puers, Science 272: 1755–1762, 1993). Therefore, an error of <0.5 nucleotide is necessary for accurate sizing of these alleles. This level of resolution has been reliably obtained only with instruments intended for automated DNA sequencing analysis. Such instruments are designed to analyze the length of DNA fragments produced by the Sanger chain termination chemistry employed in DNA sequencing (Connell, et al., 1987). This sequencing chemistry produces a set of DNA fragments each of which terminates with 1 of the 4 dideoxyribonucleotides. The fragments in the set produced differ in length by only one nucleotide and form a "ladder" of successively longer fragments which must be reliably resolved from one another by electrophoresis.

Electrophoresis instruments used to separate sequencing fragments utilize a slab gel or capillary format, but vary in their method of detection. For example, with the ALF™ and ALFexpress™ slab gel systems (Amersham Pharmacia Biotech, Piscataway, N.J.) all 4 dideoxyribonucleotide-terminating fragment types are labeled with the same fluorophore. The 4 fragments types must therefore be assigned to 4 different lanes for electrophoresis in order to distinguish among them. The ABI Prism 310® capillary and ABI Prism 377® slab gel systems (PE Applied Biosystems, Foster City, Calif.) allow electrophoresis of all fragments in the same channel or lane because different fluorophores are assigned to each of the 4 dideoxyribonucleotides. The newer Visible Genetics Microgene Clipper™ (Visible Genetics, Inc., Toronto, Canada) employs two fluorophores to identify two sets of fragments which are electrophoresed in two gel lanes. The Hitachi FMBIO® II Fluorescent Scanner employs 3 fluorophores. All of these instruments employ computerized measurement of the migration time of each fragment over a fixed distance or time (Hitachi) in order to "call" the nucleotide sequence of the DNA molecule under analysis. Since consecutive fragments differ from each other by only one nucleotide (their sequences being otherwise homologous) their relative mobilities are almost identical. Thus the small differences in length can be measured accurately and allow the alignment of fragments relative to each other when constructing the sequencing "ladder" which represents the oligonucleotide sequence.

Sequencing gel electrophoretic instruments therefore provide the resolution necessary to discriminate between DNA fragments which differ in length by only 1 nucleotide (Carrano et al., 1989). When these instruments were later adapted to STR analysis a problem arose, because there was no longer an entire series of similarly mobile fragments to be aligned in correct series, but rather only one or two alleles from each amplified locus, depending upon whether the subject was homo- or heterozygous. Now the lengths of these fragments had to be measured by means of calibration standards in order to assign them the correct allele number. The standards employed were no longer almost identical in sequence like the series of Sanger gene termination fragments, but were heterologous, usually produced by restriction enzymatic digestion of microbial DNA. Sequence differences and the ensuing electrophoretic mobility differences (Frank, R. et al., 1979) between the calibration standards and their target DNA caused a large and variable calibration error of up to 3 nt (AMPFlSTR® User's Manual, 1998). Manufacturers have corrected this error with either a heterologous or chemically compounded internal and external lane standard labeled with its own fluorophore distinct from that of their target alleles combined with an external lane allelic ladder (Schumm, J. W., 1997). Allelic ladders themselves are not co-electrophoresed as internal lane standards because by migrating in the same position as the sample alleles they could interfere with their measurement by obscuring small sample peaks, by spectral interference or by peak broadening.

LSB overcome many of the difficulties in calibration of STR measurement with markers of incompatible electrophoretic mobility. They are made through the deletion or addition of tandem repeat units within the polymorphic regions of STR containing genetic loci to produce bracketing variant alleles just shorter and longer than all alleles or common alleles of their locus. They differ from true alleles of their locus only by containing fewer or more repeat units in their polymorphic regions. Therefore, their electrophoretic mobility is in register with true alleles of their locus of origin even during changed operating conditions because true alleles and LSB are affected in almost the same way due to their comparable length and chemical structure.

However, the resolution of PCR amplicons from multiplexed STR alleles presents additional challenges since typically the alleles of many loci in a sample are most efficiently analyzed together. Therefore, the potential length range of the PCR amplicons from a given STR locus must not overlap the length range of any other locus, the arnplicons of which are to be co-electrophoresed in the same lane. Barring the use of some means of differential labeling, it is not possible to individually distinguish the loci of origin of overlapping alleles. Overlapping amplicons are most commonly identified by labeling them with different fluorophores, each of which specifically labels either a single locus or several loci which do not overlap and can therefore be identified solely by migration time (Sullivan et al., 1992).

The electrophoresis system which is to be utilized must be equipped with a fluorometer capable of separating and detecting photon emissions of different wavelengths from the different fluorophores (Carrano et al., 1989). Several adequate electrophoresis systems are available. For example, Applied Biosystems, Inc. has developed a four fluorophore slab gel system. Three of the fluorophores are used to label each of three overlapping triplexes and the fourth is used to label an internal lane calibration standard (Ziegle et al., 1992). The four-fluorophore detector has been adapted to capillary electrophoresis systems (Demers et al., 1998). In order to correct for deviant mobility compared to the target alleles, the internal lane standard is calibrated against allelic ladders derived from each locus by co-electrophoresis with them in an external lane on the 377 Prism® slab gel instrument (Ziegel) or by another electrophoresis with them in the same capillary on the 310 Prism® instrument (Lazaruk et al., 1998). Visible Genetics, Inc. has developed an electrophoresis instrument (VGI Microgene Clipper™) capable of detecting fluorescence from two fluorophores which can therefore discriminate two STR multiplexes simultaneously in a single gel lane. Hitachi Genetic Systems (South San Francisco, Calif.) has developed a three fluorophore detector (FIMBIO II™).

Another important constraint on the multiplexing of STR fragments is the limit to the maximum size of PCR amplicons which can be accurately resolved by electrophoresis with a standard size gel or capillary system within a reasonable period of time. Additionally, in forensic samples longer alleles are more subject to degradation (Walsh et al., 1992; Edwards et al., 1994). A desirable fragment size range for human identification testing is therefore up to about 400 bp (Gill et al., 1996). Depending upon the potential size range of the alleles to be amplified, the number of STR amplicons which can be multiplexed in a single gel lane will be limited by their length, even if the amplicons of the selected markers do not overlap (Klimpton et al., 1993; Schumm, U.S. Pat. No. 5,843,660).

The analysis of highly polymorphic STR genetic loci has become the preeminent method of forensic identification (Robertson, 1995). In the United States, the Federal Bureau of Investigation (FBI) has established a national data base called the Combined DNA Index System (CODIS) to allow state and local crime laboratories to store and match forensic DNA test results. These loci have met extensive evaluation and selection criteria including: 1) a high degree of polymorphism ensuring their power to discriminate between individuals, 2) a sufficient number of loci with a large power of exclusion to prevent false matching of crime samples, 3) reproducible amplification by PCR from forensic DNA samples, and 4) alleles accurately discriminated by electrophoresis. Since its inception, the CODIS system is proving its worth by providing crucial evidence leading to the conviction of many criminals.

Current processing of forensic samples for CODIS still requires two PCR reaction vessels and two electrophoretic lanes, be it with a slab gel or capillary device. For example, both Applied Biosystems, Inc. 310 and 377 Prism® machines can simultaneously resolve the emission spectra of up to four of the currently available fluorophores. But one color must be reserved for the internal lane calibration standard, leaving only three fluorophores to label the thirteen polymorphisms (Ziegle, 1992). The strategy for PCR amplification in this system has therefore been restricted to the development of three multiplex subsets, each labeled with its own fluorophore. With currently known primer pairs, labeling with only three fluorophores has not been enough to accommodate all thirteen CODIS loci in a manner which allows them to be co-amplified in a single reaction vessel producing fragment lengths of <400 bp for analysis in a single electrophoretic channel.

For several reasons it is desirable that all 13 CODIS loci be amplified in a single reaction vessel and analyzed in a single electrophoretic lane. The reasons include: 1) conservation of sample DNA; 2) avoidance of potential mix-ups due to split samples; 3) uniform PCR reaction conditions to maximize the opportunity for uniform, readable electrophoretic peak heights, and uniform extra nucleotide addition by DNA polymerase to increase accuracy of DNA fragment length measurements; 4) uniform electrophoretic conditions without any lane to lane variation; 5) uniform polynucleotide fragment detection conditions to increase accuracy; 6) enhanced sample throughput; 7) more opportunity for automation; and 8) lower cost.

It would be of benefit to have available multiplex configurations which are designed to amplify all CODIS alleles together in one vessel in order to produce a similar abundance of each, with preferred minimum and maximum amplicon lengths of between 100–400 bp or more preferred 100–350 bp. PCR amplicons of <100 bp may be difficult to distinguish from primer/dimer amplification artifacts. The system would have to amplify and detect all known or all common polymorphisms of the CODIS loci. In addition, the multiplex PCR groupings detected by the same label would need to produce non-overlapping amplicons within each subset, and multiplex subsets must be limited to those that can be amplified, differentially labeled and distinguished using technology which is currently available (Miscicka-Sliwka et al, 1997; Oldroyd et al, 1995). Further, it would be of benefit if the method utilized internal lane standards accurate in calibration which were fully compatible with and specific for the loci which were being amplified, and did not require separate labeling (Dau, U.S. Pat. No. 6,013,444, which is herein incorporated by reference).

SUMMARY OF THE INVENTION

The invention provides a method of determining the alleles present at a plurality of loci in a DNA-containing sample using multiplex PCR amplification of the loci. PCR amplification is carried out using primer pairs which are specific for each locus. The loci include the thirteen CODIS loci (FGA, vWA, TH01, TPOX, CSF1PO, D3S1358, D5S818, D7S820, D8S1179, D13S317, D16S539, D18S51, D21S11) which have been selected by the Federal Bureau of Investigation as those to be utilized in forensic databases (Schumm et al., 1999) with or without amelogenin for sex determination (Sullivan, 1993). The DNA sequence of loci D3S1358 and D13S317 is described. The loci have been organized into several different "multiplex subsets" (A1, B1, C1, D1, A2, B2, C2, D2, A3, B3, C3, D3, A4, C4, D4, C5, D5, C6, D6 and C7) such that, within a given multiplex subset, the amplicons produced by PCR amplification of the loci in that subset do not overlap one another in length and are detected by means of the same label. Multiplex subsets are amplified in a single reaction vessel and detected in a single electrophoretic channel. Their amplicons may be assigned fragment lengths based upon calibration by LSB electrophoresed as internal and/or external channel standards. In addition to LSB, multiple markers composed of heterologous or chemically compounded DNA may also be applied as internal and/or external lane standards and alleles from the loci to be measured may also be applied as external lane standards.

The multiplex subsets have been further configured into groups of "compound multiplexes" which contain 2 or more multiplex subsets. The compound multiplexes can be amplified (and concomitantly labeled) in a single PCR reaction vessel, and analyzed in a single channel of, for example, an electrophoresis apparatus. While the amplicons produced by two different multiplex subsets may overlap in length, the overlapping amplicons may be distinguished from one another by differential labeling of the group of primers for each multiplex subset. Compound multiplexes are detected by analytical electrophoresis using multiple calibration for their multiplex subsets. Also provided are kits containing primer pairs and LSB for use in carrying out the methods of the present invention.

The invention further provides a method of determining the lengths of the alleles of a genetic locus by utilizing both internal and external lane calibration standards. Various combination of internal and external lane calibration standards may be utilized, including but not limited to: LSB as internal lane standards, and LSB combined with at least one true allele as external lane standards; MM as internal lane standards, and LSB combined with at least one true allele and MM as external lane standards; MM as internal lane standards, and MM and locus specific alleleic ladders as external lane standards.

The invention further provides a method for the analysis of the data obtained via the use of both internal and external lane calibration standards, and software to carry out the analysis.

DETAILED DESCRIPTION OF THE PREFERRED EMBODIMENTS OF THE INVENTION

Definitions

Figure 1:
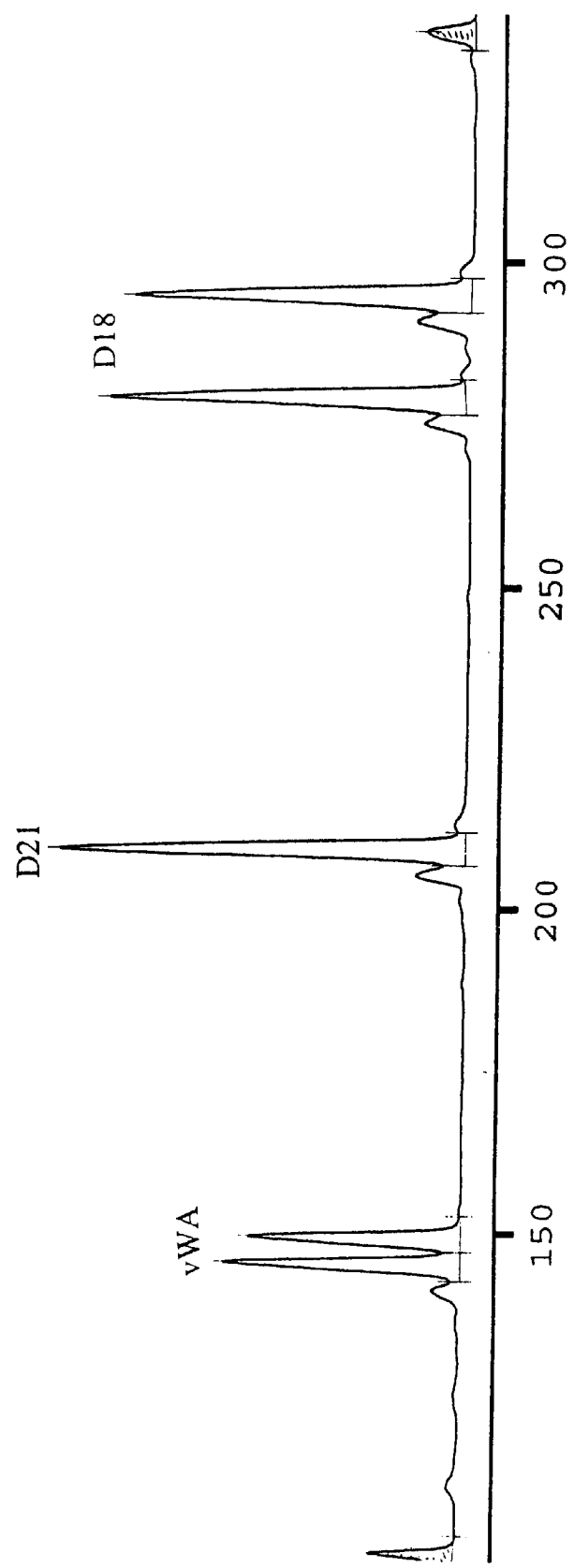
FIG. 1 is a printed image from the ALFexpress automated sequencer (Amersham Pharmacia Biotech) showing the fluorescent detection upon electrophoresis of the PCR product after amplification of the loci from multiplex subset A1: vWA, D21 S11, and D18S51. Peak areas correspond to fluorescence intensity and are depicted graphically as a function of fragment length (nt). Fluorescent peaks measured at 101 and 335 nt represent DNA size standards.

The following definitions are intended to assist in providing a clear and consistent understanding of the scope and detail of the terms therein.

Allele: a genetic variation associated with a segment of DNA, i.e., one of two or more alternate forms of a DNA sequence occupying the same locus.

Alleic ladder: standard size marker consisting of amplified alleles from its locus.

Amplicon: the DNA fragment which is produced by a PCR amplification reaction.

Biochemical nomenclature: standard biochemical nomenclature is used herein in which the nucleotide bases are designated as adenine (A); thymine (T); guanine (G); and cytosine (C). Corresponding nucleotides are, for example, deoxyguanosine-5'-triphosphate (dGTP).

Compound Multiplex PCR: at least one multiplex subset is amplified together with at least one other genetic locus or multiplex subset in the same reaction vessel, producing DNA fragments of potentially overlapping lengths which may be discriminated from one another by differential labeling.

DNA polymorphism: the condition in which two or more different nucleotide sequences in a DNA sequence coexist in the same interbreeding population.

Forward primer: hybridizes with the antisense strand of DNA to produce the sense strand by PCR.

Locus (or genetic locus): a specific position on a chromosome. Alleles of a locus are located at identical sites on homologous chromosomes.

Locus Specific Bracket (LSB): refers to a pair of locus specific DNA molecular weight markers, one of which is slightly longer than the longest common allele of a locus, and one of which is slightly shorter than the shortest common allele of a locus, and which otherwise have sequences homologous to the longest and shortest common alleles of the locus, respectively. Analogous LSB can also be designed to bracket uncommon alleles whose length falls outside of the range of common alleles. LSB may be 1) added in the lane (together with the amplicons of their locus) at the time of electrophoresis, or 2) the DNA template for the LSB may be added during the PCR reaction for co-amplification with their loci from genomic DNA. LSB are generated according to the method outlined in U.S. Pat. No. 6,013,444 to Dau and Liu, which is incorporated herein in its entirety by reference.

Locus-specific primer: a primer that specifically hybridizes with a portion of the stated locus or its complementary strand, at least for one allele of the locus, and does not hybridize efficiently with other DNA sequences under the conditions used in the amplification method.

Multiple Markers (MM): DNA calibration markers derived from heterologous or other DNA not specific for the loci to be measured.

Multiplex PCR: more than one genetic loci are simultaneously PCR amplified together in the same reaction vessel. For example, the multiplex PCR amplification of STR loci for human identification is described in U.S. Pat. No. 5,843,660 to Schumm et al. which is incorporated herein by reference.

Multiplex subset: a set of genetic loci which, when PCR amplified, produces amplicons which do not overlap in length. The amplicons produced via PCR amplification of a multiplex subset can thus all be labeled with the same detectable label, separated by electrophoresis in a single channel, and accurately identified.

Polymerase chain reaction (PCR): a technique which utilizes forward and reverse primer pairs specific for regions which flank a target DNA (for example, a specific genetic locus) in order to amplify the number of copies of the target DNA sequence by approximately $10^6$ times or more. The technique employs cycles of denaturation, annealing with primer, and extension with DNA polymerase. The polymerase chain reaction process for amplifying nucleic acid is described in U.S. Pat. No. 4,683,195 to Mullis et al. and U.S. Pat. No. 4,683,202 to Mullis, each of which are incorporated herein by reference.

Polymorphic short tandem repeat loci: STR loci in which the number of repetitive sequence elements (and net length of sequences) in a particular region of genomic DNA varies from allele to allele, and from individual to individual.

Primers: two single-stranded oligonucleotides or DNA fragments which hybridize with opposing strands of a locus such that the 3' termini of the primers are in closest proximity.

Primer pair: two primers including, primer 1 that hybridizes to a single strand at one end of the DNA sequence to be amplified, and primer 2 that hybridizes with the other end on the complementary-strand-of-the-DNA-sequence to be amplified.

Primer site: the area of the target DNA to which a primer hybridizes.

Reverse Primer: a primer which hybridizes with the sense strand of DNA to produce the antisense strand by PCR.

Short tandem repeat loci (STR loci): regions of the human genome which contain short, repetitive sequence elements of 2 to 7 base pairs in length.

Size Range (common alleles): refers to the range in length (the number of nucleotides) of the most common alleles (i.e. those alleles which occur most frequently in the human population tested to date) present at the locus.

Size Range (LSB): refers to the range in length (the number of nucleotides) of the calibration standard Locus Specific Brackets.

Multiplex Groupings

The present invention provides a method for determining the alleles which are present at a plurality of STR loci in a DNA containing sample. In a preferred embodiment of the present invention, the STR loci are the thirteen loci specified for analysis by CODIS: vWA, TH01, TPOX, CSF1PO, D13S317, D5S818, D7S820, D16S539, D21S11, D18S51, D3S1358, D8S1179, and FGA. The method of the present invention encompasses multiplex PCR amplification of all the loci in a single reaction vessel and subsequent analysis of all of the amplicons produced from all thirteen loci in a single electrophoretic channel. Calibration standards, preferably in the form of LSB, MM, or locus specific alleles are included in the same electrophoretic channel and/or in an external channel. Accurate identification of each amplicon is assured at two levels: first, the primer pairs for each multiplex subset have been selected so that the amplicons generated within a given multiplex subset do not overlap in length. Secondly, multiplex subsets are grouped into "compound multiplexes" which contain several multiplex subsets and encompass all the loci of interest. Each multiplex subset is labeled with a different detectable label. Therefore, amplicons from different multiplex subsets within the compound multiplex which do overlap will still be readily distinguishable from each other (i.e. their locus of origin will be accurately assigned) because of the attached label, which is unique to the multiplex subset associated with that locus.

In a further preferred embodiment of the present invention, the amelogenin locus is included as part of a multiplex subset. Amelogenin is a single copy X-Y homologous region which can be amplified in order to determine the sex of the DNA donor (Sullivan, et al., 1993). Only one pair of primers is required to amplify the amelogenin locus from both the X and Y chromosomes. In females, a 106 base pair PCR product is produced from the X chromosome. In males, two PCR products are produced: the 106 base pair product from the X chromosome and a 112 base pair product from the Y chromosome. Detection of the amelogenin locus affords an additional level of discrimination in human identification which can be of use in certain forensic and other situations.

In addition, the method encompasses utilizing LSB internal lane standards (Dau, 1997). LSBs for a STR polymorphic locus are created by either adding or subtracting tandem repeat units to STR alleles to create novel alleles which are either longer or shorter, respectively, than all known or common true alleles of this locus of origin. This strategy generates calibration markers useful in electrophoresis to accurately determine the DNA fragment lengths of alleles of the locus of origin. Because, these markers "bracket" (i.e. do not overlap) all common or known alleles of their locus, they can be labeled with the same detectable label and electrophoresed in the same channel, freeing the additional detectable label usually employed on the calibration standard for use. in labeling another multiplex subset. As a result, by using four different detectable labels, the amplicons of all thirteen CODIS loci plus their highly homologous (and therefore accurate) LSB internal calibration standards may be analyzed in a single electrophoretic channel with or without additional external lane calibration. For amelogenin, any of the smaller appropriately sized LSBs (e.g. D13S317 short and D5S818 short, which are 99 and 135 bp, respectively) may be used as molecular weight calibration markers.

In a preferred embodiment of the present invention, the thirteen CODIS loci and amelogenin are grouped into multiplex subsets as shown in Table 1. Salient characteristics of each locus are also given in the Table, including the repeat sequence, the Genebank accession number or locus specific DNA sequence, number of common alleles, size range of alleles, size range of their corresponding LSBs, and the number of repeat units in LSBs.

In other preferred embodiments of the present invention, additional, alternative primer pairs have been designed for the PCR amplification of the loci D18S51, D21S11, D3S1358, FGA, D5S818, TH01, and TPOX. Their usefulness establishes that multiple alternative primer designs can be conceived which can serve to amplify and co-amplify CODIS loci in multiplex configurations. Multiplex subsets A2, A3, A4, B2, C3, C4, C6, C7, D4, D5 and D6 have been developed using alternative primers in combination with original primers from other CODIS loci. When a locus in a multiplex subset has been amplified using an alternative primer or primer pair, the locus will be marked with prime ('). For example, "D18S51'" indicates that the D18S51 locus was amplified by the original primer pair, but "D18S51'" indicates that the vWA locus was amplified by the alternative primer pair. Marking of a locus with a double prime (") indicates a second alternative primer or primer pair at that locus.

TABLE 1

MULTIPLEX SUBSETS AND LOCI CHARACTERISTICS

| Locus | Repeat Sequence | Genebank Accession # | Number of Common Alleles | Size Range: Alleles | Size Range: LSBs | # of Repeats in LSBs |
|---|---|---|---|---|---|---|
| Multiplex Subset A1 | | | | | | |
| vWA | tcta | m25858 | 13 to 20 | 128–156 | 116–168 | 10 |
| | | | | | | 23 |
| D21S11 | tcta | m84567 | 24 to 38 | 185–241 | 181–245 | 23 |
| | | | | | | 39 |
| D18S51 | agaa | x91255 | 9 to 26 | 256–324 | 248–332 | 7 |
| | | | | | | 28 |
| Multiplex Subset B1 | | | | | | |
| D3S1358 | tcta | refer to *[1] and *[3] | 12 to 19 | 115–143 | 99–151 | 8 |
| | | | | | | 21 |
| D8S1179 | tcta | g8710 | 8 to 19 | 168–212 | 160–216 | 6 |
| | | | | | | 20 |
| D16S539 | agat | g07925 | 5 to 15 | 248–288 | 244–296 | 4 |
| | | | | | | 17 |
| CSF1PO | agat | g30238 | 6 to 5 | 303–339 | 299–343 | 5 |
| | | | | | | 16 |
| Multiplex Subset C1 | | | | | | |
| D5S818 | agat | g08446 | 7 to 16 | 139–175 | 135–179 | 6 |
| | | | | | | 17 |
| D7S820 | gata | g08616 | 6 to 15 | 196–232 | 192–236 | 5 |
| | | | | | | 16 |
| FGA | cttt | m64982 | 18 to 30 | 284–332 | 260–340 | 12 |
| | | | | | | 32 |
| Multiplex Subset D1 | | | | | | |
| D13S317 | gata | g09017*[2] | 7 to 15 | 107–139 | 95–143 | 4 |
| | | | | | | 16 |
| TH01 | aatg | g220099 | 5 to 11 | 189–213 | 177–233 | 2 |
| | | | | | | 16 |
| TPOX | aatg | g307519 | 6 to 13 | 240–268 | 236–272 | 5 |

TABLE 1-continued

MULTIPLEX SUBSETS AND LOCI CHARACTERISTICS

| Locus | Repeat Sequence | Genebank Accession # | Number of Common Alleles | Size Range: Alleles | Size Range: LSBs | # of Repeats in LSBs |
|---|---|---|---|---|---|---|
| | | | | | | 14 |
| Multiplex Subset C2 | | | | | | |
| Amelogenin | X,Y | n.a. | X,Y | 106,112 | n.a. | n.a. |
| D5S818 | agat | g08446 | 7 to 16 | 139–175 | 135–179 | 6 |
| | | | | | | 17 |
| D7S820 | gata | g08616 | 6 to 15 | 196–232 | 192–236 | 5 |
| | | | | | | 16 |
| FGA | cttt | m64982 | 18 to 30 | 284–332 | 260–340 | 12 |
| | | | | | | 32 |
| Multiplex Subset A2 | | | | | | |
| vWA | tcta | m25858 | 13 to 20 | 128–156 | | |
| D21S11' | tcta | m84567 | 24 to 38 | 191–247 | | |
| D18S51 | agaa | x91255 | 9 to 26 | 256–324 | | |
| Multiplex Subset B2 | | | | | | |
| D3S1358' | tcta | refer to *1 and *4 | 12 to 19 | 112–140 | | |
| D8S1179 | tcta | g08710 | 8 to 19 | 168–212 | | |
| FGA' | cttt | m64982 | 18 to 30 | 261–309 | | |
| Multiplex Subset C3 | | | | | | |
| D13S317 | gata | g09017*2 | 7 to 15 | 107–139 | | |
| D5S818' | agat | g08446 | 7 to 16 | 142–178 | | |
| D7S820 | gata | g08616 | 6 to 15 | 196–232 | | |
| D16S539 | agat | g07925 | 5 to 15 | 248–288 | | |
| Multiplex Subset D2 | | | | | | |
| vWA | tcta | m25858 | 13 to 20 | 128–156 | | |
| TH01' | aatg | g220099 | 5 to 11 | 191–215 | | |
| TPOX | aatg | g307519 | 6 to 13 | 240–268 | | |
| CSF1PO | agat | g30238 | 6 to 15 | 303–339 | | |
| Multiplex Subset A3 | | | | | | |
| vWA | tcta | m25858 | 13 to 20 | 128–156 | 116–168 | 10 |
| | | | | | | 23 |
| D21S11" | tcta | m845567 | 24 to 38 | 182–238 | 178–242 | 23 |
| | | | | | | 39 |
| D18S51' | agaa | x91255 | 9 to 26 | 260–328 | 252–336 | 7 |
| | | | | | | 28 |
| Multiplex Subset B3 | | | | | | |
| D351358' | tcta | refer to *1 and *5 | 12 to 19 | 113–141 | 97–149 | 8 |
| | | | | | | 21 |
| D8S1179 | tcta | g08710 | 8 to 19 | 168–212 | 160–216 | 6 |
| | | | | | | 20 |
| D165539 | agat | g07925 | 5 to 15 | 248–288 | 244–296 | 4 |
| | | | | | | 17 |
| CSF1PO | agat | g30238 | 6 to 15 | 303–339 | 299–343 | 5 |
| | | | | | | 16 |
| Multiplex Subset C4 | | | | | | |
| D5S818' | agat | g08446 | 7 to 16 | 142–178 | 138–182 | 6 |
| | | | | | | 17 |
| D75820 | gata | g08616 | 6 to 15 | 196–232 | 192–236 | 5 |
| | | | | | | 16 |
| FGA | cttt | m64982 | 18 to 30 | 284–332 | 260–340 | 12 |
| | | | | | | 32 |
| Multiplex Subset D3 | | | | | | |
| D13S317 | gata | g09017*2 | 7 to 15 | 107–139 | 95–143 | 4 |
| | | | | | | 16 |
| TH01 | aatg | g220099 | 5 to 11 | 189–213 | 177–233 | 2 |
| | | | | | | 16 |
| TPOX' | aatg | g307519 | 6 to 13 | 247–275 | 243–279 | 5 |
| | | | | | | 14 |
| Multiplex Subset C5 | | | | | | |
| Amelogenin | X,Y | n.a. | X,Y | 106,112 | n.a. | |
| D5S818' | agat | g08446 | 7 to 16 | 142–178 | 138–182 | 6 |
| | | | | | | 17 |
| D7S820 | gata | g08616 | 6 to 15 | 196–232 | 192–236 | 5 |

TABLE 1-continued

MULTIPLEX SUBSETS AND LOCI CHARACTERISTICS

| Locus | Repeat Sequence | Genebank Accession # | Number of Common Alleles | Size Range: Alleles | Size Range: LSBs | # of Repeats in LSBs |
|---|---|---|---|---|---|---|
| FGA | cttt | m64982 | 18 to 30 | 284–332 | 260–340 | 16 12 32 |
| Multiplex Subset A4 | | | | | | |
| vWA | tcta | m25858 | 13 to 20 | 128–156 | 116–168 | 10 23 |
| D21S11 | tcta | m84567 | 24 to 38 | 185–241 | 178–242 | 23 39 |
| D18S51' | agaa | x91255 | 9 to 26 | 261–329 | 253–337 | 7 28 |
| Multiplex Subset D4 | | | | | | |
| D13S317 | gata | g09017*² | 7 to 15 | 107–139 | 95–143 | 4 16 |
| TM01 | aatg | g220099 | 5 to 11 | 189–213 | 177–233 | 2 16 |
| TPOX | aatg | g307519 | 6 to 13 | 240–268 | 236–272 | 5 14 |
| CSF1PO | agat | g30238 | 6 to 15 | 303–339 | 299–343 | 5 16 |
| Multiplex Subset C6 | | | | | | |
| D13S317 | gata | g09017*² | 7 to 15 | 107–139 | 95–143 | 4 16 |
| FGA" | cttt | m64982 | 18 to 30 | 218–266 | 194–274 | 12 32 |
| Multiplex Subset D5 | | | | | | |
| Amelogenin | X,Y | n.a. | X,Y | 106,112 | n.a. | |
| D5S818' | agat | g08616 | 7 to 16 | 142–178 | 138–182 | 6 17 |
| D7S820 | gata | g08616 | 6 to 15 | 196–232 | 192–236 | 5 16 |
| TPOX' | aatg | g307519 | 6 to 13 | 247–275 | 243–279 | 5 14 |
| TH01" | aatg | g220099 | 5 to 11 | 298–322 | 286–342 | 2 16 |
| Multiplex Subset C7 | | | | | | |
| Amelogenin | X,Y | n.a. | X,Y | 106,112 | n.a. | |
| D5S818' | agat | g08446 | 7 to 16 | 142–178 | 138–182 | 6 17 |
| FGA" | cttt | m64982 | 18 to 30 | 218–266 | 194–274 | 12 32 |
| Multiplex Subset D6 | | | | | | |
| D13S317 | gata | g09017*² | 7 to 15 | 107–139 | 95–143 | 4 16 |
| D7S820 | gata | g08616 | 6 to 15 | 196–232 | 192–236 | 5 16 |
| TPOX' | aatg | g307519 | 6 to 13 | 247–275 | 243–279 | 5 14 |
| TH01" | aatg | g220099 | 5 to 11 | 298–322 | 286–342 | 2 16 |

Prime (') or double prime (") indicates that a locus is amplified with an alternative primer pair.
*¹= D3S1358 sequences from sample K562 (SEQ ID # 43):
1 actgcagtcc aatctgggtg acagagcaag accctgtctc atagatagat agatagatag
61 atagatagat agatagatag atagatagat agacagacag atagatacat gcaagcctct
121 gttgatttca t
*²= D13S317 sequences from sample K562 (SEQ ID # 44):
1 tgctggacat ggtatcacag aagtctggga tgtggaggag agttcatttc tttagtgggc
61 atccgtgact ctctggactc tgacccatct aacgcctatc tgtatttaca aatacattat
121 ctatctatct atctatctat ctatctatca atcaatcatc tatctatctt tctgtctgtc
181 ttttggggct gcctatggct caacccaagt tgaaggagaa gatttgacca acaattcaag
241 ctctctgaa
*³= Forward and reverse primers from Li et al.
*⁴= Forward and reverse primers from Liu et al.
*⁵= Forward primer from Liu et al.; reverse primer from Li et al.
n.a. = not applicable Table 2 gives pertinent information concerning primers used in the practice of several preferred embodiments of the present invention, including their genetic locus, sequence, length, Tm, %GC, 5' position in the Genebank sequence and SEQ ID #. The primers in Table 2 are grouped according to the multiplex subsets in which they are used and therefore may appear more than once in the Table. The primers are named according to the locus which they amplify, and are designated "F" or "R" for "forward" and "reverse", respectively. Further, as mentioned above, alternative primers have been designed for several of the thirteen loci and these are indicated by the placement of prime (') or double prime (") directly after the "F" or "R" in the locus designation. For example, D18S51.R is the original forward reverse primer for the D18S51 locus, and D18S51.R' is an alternative forward primer.

TABLE 2

Primer characteristics.

| Locus | Sequence 5' to 3' | Length (nt) | Tm °C. | % GC | 5' position | SEQ ID # |
|---|---|---|---|---|---|---|
| Multiplex Subset A1 | | | | | | |
| vWA.F | gatgtgaaagccctagtgga | 20 | 60 | 50 | 1630 | 1 |
| vWA.R | cataggatggatggatagatgga | 23 | 61 | 43 | 1777 | 2 |
| D21S11.F | aattccccaagtgaattgccttcta | 25 | 61 | 40 | 133 | 3 |
| D21S11.R | tcaatgttctccagagacagac | 22 | 61 | 45 | 319 | 4 |
| D18S51.F | ttcatgccactgcacttcactct | 23 | 63 | 48 | 9 | 5 |
| D18S51.R | ccgactaccagcaacaacac | 20 | 62 | 55 | 280 | 6 |
| Multiplex Subset B1 | | | | | | |
| D3S1358.F | actgcagtccaatctgggt | 20 | 60 | 50 | 1[*1] | 7 |
| D3S1358.R | atgaaatcaacagaggcttg | 20 | 56 | 40 | 127[*1] | 8 |
| D8S1179.F | atgtattttgtatttcatgtgtacattcg | 30 | 59 | 27 | 12 | 9 |
| D8S1179.R | cacgtagctataattagttcattttcatca | 30 | 61 | 30 | 195 | 10 |
| D16S539.F | tgtacaagtgccagatgctcgtt | 23 | 63 | 48 | 115 | 11 |
| D16S539.R | ccatttacgtttgtgtgtgcatctgt | 26 | 63 | 42 | 386 | 12 |
| CSF1PO.F | ctgtgtctcagtttcctacctgt | 24 | 63 | 46 | 11887 | 13 |
| CSF1PO.R | tggaggtcatccttatctcctttc | 24 | 63 | 46 | 12213 | 14 |
| Multiplex Subset C1 | | | | | | |
| D5S818.F | gacaagggtgattttcctctttggt | 25 | 63 | 44 | 65 | 15 |
| D5S818.R | gtgattccaatcatagccacag | 22 | 61 | 45 | 227 | 16 |
| D7S820.F | aggctgactatggagttatttaagg | 26 | 61 | 38 | 45 | 17 |
| D7S820.R | ttatcctcattgacagaattgcac | 24 | 59 | 38 | 264 | 18 |
| FGA.F | gcagggcataacattatccaaaag | 24 | 61 | 42 | 2795 | 19 |
| FGA.R | gatcctctgacactcggttgta | 22 | 63 | 50 | 3090 | 20 |
| Multiplex Subset D1 | | | | | | |
| D13S317.F | tctgacccatctaacgcctat | 21 | 60 | 48 | 79[*2] | 21 |
| D13S317.R | gcccaaaaagacagacagaaaga | 23 | 61 | 43 | 189[*2] | 22 |
| TH01.F | ggcaaatagggggcaaaattcaaag | 25 | 63 | 44 | 1093 | 23 |
| TH01.R | gaaaagctcccgattatccag | 21 | 61 | 48 | 1297 | 24 |
| TPOX.F | cttcctctgcttcactttttcacc | 23 | 63 | 48 | 1691 | 25 |
| TPOX.R | ccttctgtccttgtcagcgttta | 23 | 63 | 48 | 1950 | 26 |
| Multiplex Subset C2 | | | | | | |
| Ame1.F[1] | cctgggctctgtaaagaatagtg | 23 | 63 | 48 | 71959 | 27 |
| Ame1.R[1] | atcagagcttaaactgggaagctg | 24 | 63 | 46 | 72063 | 28 |
| D5S818.F | gacaagggtgattttcctctttggt | 25 | 63 | 44 | 65 | 15 |
| D5S818.R | gtgattccaatcatagccacag | 22 | 61 | 45 | 227 | 16 |
| D7S820.F | aggctgactatggagttatttaagg | 26 | 61 | 38 | 45 | 17 |
| D7S820.R | ttatcctcattgacagaattgcac | 24 | 59 | 38 | 264 | 18 |
| FGA.F | gcagggcataacattatccaaaag | 24 | 61 | 42 | 2795 | 19 |
| FGA.R | gatcctctgacactcggttgta | 22 | 63 | 50 | 3090 | 20 |
| Multiplex Subset A2 | | | | | | |
| vWA.F | gatgtgaaagccctagtgga | 20 | 60 | 50 | 1630 | 1 |
| vWA.R | cataggatggatggatagatgga | 23 | 61 | 43 | 1777 | 2 |
| D21S11.F | aattccccaagtgaattgccttcta | 25 | 61 | 40 | 133 | 3 |
| D21S11.R[1] | tattagtcaatgttctccagagacagac | 28 | 63 | 39 | 325 | 29 |
| D18S51.F | ttcatgccactgcacttcactct | 23 | 63 | 48 | 9 | 5 |
| D18S51.R | ccgactaccagcaacaacac | 20 | 62 | 55 | 280 | 6 |
| Multiplex Subset B2 | | | | | | |
| D3S1358.F' | tgcagtccaatctgggtgaca | 21 | 63 | 52 | 3[*1] | 30 |
| D3S1358.R' | tgaaatcaacagaggcttgcatgt | 24 | 61 | 42 | 126[*1] | 31 |
| D8S1179.F | atgtattttgtatttcatgtgtacattcg | 30 | 59 | 27 | 12 | 9 |
| D8S1179.R | cacgtagctataattagttcattttcatca | 30 | 61 | 30 | 195 | 10 |
| FGA.F' | atgccccataggttttgaactcac | 24 | 63 | 46 | 2823 | 32 |
| FGA.R' | tctcagatcctctgacactcg | 21 | 63 | 52 | 3095 | 33 |
| Multiplex Subset C3 | | | | | | |
| D13S317.F | tctgacccatctaacgcctat | 21 | 60 | 48 | 79[*2] | 21 |

TABLE 2-continued

_Primer characteristics._

| Locus | Sequence 5' to 3' | Length (nt) | Tm °C. | % GC | 5' position | SEQ ID # |
|---|---|---|---|---|---|---|
| D13S317.R | gcccaaaaagacagacagaaaga | 23 | 61 | 43 | 189*2 | 22 |
| D5S818.F | gacaagggtgattttcctctttggt | 25 | 63 | 44 | 65 | 15 |
| D5S818.R' | caagtgattccaatcatagccacag | 25 | 63 | 44 | 230 | 34 |
| D7S820.F | aggctgactatggagttattttaagg | 26 | 61 | 38 | 45 | 17 |
| D7S820.R | ttatcctcattgacagaattgcac | 24 | 59 | 38 | 264 | 18 |
| D16S539.F | tgtacaagtgccagatgctcgtt | 23 | 63 | 48 | 115 | 11 |
| D16S539.R | ccatttacgtttgtgtgtgcatctgt | 26 | 63 | 42 | 386 | 12 |
| Multiplex Subset D2 | | | | | | |
| vWA.F | gatgtgaaagccctagtgga | 20 | 60 | 50 | 1630 | 1 |
| vWA.R | cataggatggatggatagatgga | 23 | 61 | 43 | 1777 | 2 |
| TH01.F | ggcaaatagggggcaaaattcaaag | 25 | 63 | 44 | 1093 | 23 |
| TH01.R' | ctgaaaagctcccgattatccag | 23 | 63 | 48 | 1299 | 35 |
| TPOX.F | cttcctctgcttcactttcacc | 23 | 63 | 48 | 1691 | 25 |
| TPOX.R | ccttctgtcctgtcagcgttta | 23 | 63 | 48 | 1950 | 26 |
| CSF1PO.F | ctgtgtctcagttttcctacctgt | 24 | 63 | 46 | 11887 | 13 |
| CSF1PO.R | tggaggtcatccttatctcctttc | 24 | 63 | 46 | 12213 | 14 |
| Multiplex Subset A3 | | | | | | |
| vWA.F | gatgtgaaagccctagtgga | 20 | 60 | 50 | 1630 | 1 |
| vWA.R | cataggatggatggatagatgga | 23 | 61 | 43 | 1777 | 2 |
| D21S11.F' | tccccaagtgaattgccttcta | 22 | 61 | 44 | 136 | 36 |
| D21S11.R | tcaatgttctccagagacagac | 22 | 61 | 45 | 319 | 4 |
| D18S51.F | ttcatgccactgcacttcactct | 23 | 63 | 48 | 9 | 5 |
| D18S51.R' | aaacccgactaccagcaacaacac | 24 | 65 | 50 | 284 | 37 |
| Multiplex Subset B3 | | | | | | |
| D3S1358.F' | tgcagtccaatctgggtgaca | 21 | 63 | 52 | 3*1 | 30 |
| D3S1358.R | atgaaatcaacagaggcttg | 20 | 56 | 40 | 127*1 | 8 |
| D8S1179.F | atgtattttgtatucatgtgtacattcg | 30 | 59 | 27 | 12 | 9 |
| D8S1179.R | cacgtagctataattagttcattttcatca | 30 | 61 | 30 | 195 | 10 |
| D16S539.F | tgtacaagtgccagatgctcgtt | 23 | 63 | 48 | 115 | 15 |
| D16S539.R | ccatttacgtttgtgtgtgcatctgt | 26 | 63 | 42 | 386 | 16 |
| CSF1PO.F | ctgtgtctcagttttcctacctgt | 24 | 63 | 46 | 11887 | 13 |
| CSF1PO.R | tggaggtcatccttatctcctttc | 24 | 63 | 46 | 12213 | 14 |
| Multiplex Subset C4 | | | | | | |
| D5S818.F | gacaagggtgattttcctctttggt | 25 | 63 | 44 | 65 | 15 |
| D5S818.R | caagtgattccaatcatagccacag | 25 | 63 | 44 | 230 | 34 |
| D7S820.F | aggctgactatggagttattttaagg | 26 | 61 | 38 | 45 | 17 |
| D7S820.R | ttatcctcattgacagaattgcac | 24 | 59 | 38 | 264 | 18 |
| FGA.F | gcagggcataacattatccaaaag | 24 | 61 | 42 | 2795 | 19 |
| FGA.R | gatcctctgacactcggttgta | 22 | 63 | 50 | 3090 | 20 |
| Multiplex Subset D3 | | | | | | |
| D13S317.F | tctgacccatctaacgcctat | 21 | 60 | 48 | 79*2 | 21 |
| D13S317.R | gcccaaaaagacagacagaaaga | 23 | 61 | 43 | 189*2 | 22 |
| TH01.F | ggcaaatagggggcaaaattcaaag | 25 | 63 | 44 | 1093 | 23 |
| TH01.R | gaaaagctcccgattatccag | 21 | 61 | 48 | 1297 | 24 |
| TPOX.F | cttcctctgcttcactttcacc | 23 | 63 | 48 | 1691 | 25 |
| TPOX.R' | gctaggcccttctgtcctt | 19 | 62 | 58 | 1957 | 38 |
| Multiplex Subset C5 | | | | | | |
| Amel.F | ccttctgtcctgtcagcgttta | 23 | 63 | 48 | 71959 | 27 |
| Amel.R | atcagagcttaaactgggaagctg | 24 | 63 | 46 | 72063 | 28 |
| D5S818.F | gacaagggtgattttcctctttggt | 25 | 63 | 44 | 65 | 15 |
| D5S818.R' | caagtgattccaatcatagccacag | 25 | 63 | 44 | 230 | 34 |
| D7S820.F | aggctgactatggagttattttaagg | 26 | 61 | 38 | 45 | 17 |
| D7S820.R | ttatcctcattgacagaattgcac | 24 | 59 | 38 | 264 | 18 |
| FGA.F | gcagggcataacattatccaaaag | 24 | 61 | 42 | 2795 | 19 |
| FGA.R | gatcctctgacactcggttgta | 22 | 63 | 50 | 3090 | 20 |
| Multiplex Subset A4 | | | | | | |
| vWA.F | gatgtgaaagccctagtgga | 20 | 60 | 50 | 1630 | 1 |
| vWA.R | cataggatggatggatagatgga | 23 | 61 | 43 | 1777 | 2 |
| D21S11.F | aattccccaagtgaattgccttcta | 25 | 61 | 40 | 133 | 3 |
| D21S11.R | tcaatgttctccagagacagac | 22 | 61 | 45 | 319 | 4 |
| D18S51.F | ttcatgccactgcacttcactct | 23 | 63 | 48 | 9 | 5 |
| D18S51.R" | caaatcttactaccagcaacaacac | 25 | 61 | 40 | 285 | 39 |
| Multiplex Subset D4 | | | | | | |
| D13S317.F | tctgacccatctaacgcctat | 21 | 60 | 48 | 79*2 | 21 |
| D13S317.R | gcccaaaaagacagacagaaaga | 23 | 61 | 43 | 139*2 | 22 |
| TH01.F | ggcaaatagggggcaaaattcaaag | 25 | 63 | 44 | 1093 | 23 |

TABLE 2-continued

Primer characteristics.

| Locus | Sequence 5' to 3' | Length (nt) | Tm °C. | % GC | 5' position | SEQ ID # |
|---|---|---|---|---|---|---|
| TH01.R | gaaaagctcccgattatccag | 21 | 61 | 48 | 1297 | 24 |
| TPOX.F | cttcctctgcttcactttcacc | 23 | 63 | 48 | 1691 | 25 |
| TPOX.R' | gctaggcccttctgtcctt | 19 | 62 | 58 | 1957 | 38 |
| CSF1PO.F | ctgtgtctcagttttcctacctgt | 24 | 63 | 46 | 11887 | 13 |
| CSF1PO.R | tggaggtcatccttatctcctttc | 24 | 63 | 46 | 12213 | 14 |
| Multiplex Subset C6 | | | | | | |
| D13S317.F | tctgacccatctaacgcctat | 21 | 60 | 48 | 79*2 | 21 |
| D13S317.R | gcccaaaaagacagacagaaaga | 23 | 61 | 43 | 189*2 | 22 |
| FGA.F | gcagggcataacattatccaaaag | 24 | 61 | 42 | 2795 | 19 |
| FGA.R" | ctgctgagtgatttgtctgtaattg | 25 | 61 | 40 | 3024 | 40 |
| Multiplex Subset D5 | | | | | | |
| Amel.F | ccttctgtccttgtcagcgttta | 23 | 63 | 48 | 71959 | 27 |
| Amel.R | atcagagcttaaactgggaagctg | 24 | 63 | 46 | 72063 | 28 |
| D5SS18.F | gacaagggtgattttcctctttggt | 25 | 63 | 44 | 65 | 15 |
| D5S818'.R | caagtgattccaatcatagccacag | 25 | 63 | 44 | 230 | 34 |
| D7S820.F | aggctgactatggagttattttaagg | 26 | 61 | 38 | 45 | 17 |
| D7S820.R | ttatcctcattgacagaattgcac | 24 | 59 | 38 | 264 | 18 |
| TPOX.F | cttcctctgcttcactttcacc | 23 | 63 | 48 | 1691 | 25 |
| TPOX.R' | gctaggcccttctgtcctt | 19 | 62 | 58 | 1957 | 38 |
| TH01.F | ggcaaatagggggcaaaattcaaag | 25 | 63 | 44 | 1093 | 23 |
| TH01.R" | tcacaccacatttcaatcaaggtccat | 27 | 63 | 41 | 1406 | 41 |
| Multiplex Subset C7 | | | | | | |
| Amel.F | ccttctgtccttgtcagcgttta | 23 | 63 | 48 | 71959 | 27 |
| Amel.R | atcagagcttaaactgggaagctg | 24 | 63 | 46 | 72063 | 28 |
| D5S818.F | gacaagggtgattttcctctttggt | 25 | 63 | 44 | 65 | 15 |
| D5S818'.R | caagtgattccaatcatagccacag | 25 | 63 | 44 | 230 | 34 |
| FGA.F | gcagggcataacattatccaaaag | 24 | 61 | 42 | 2795 | 19 |
| FGA.R" | ctgctgagtgatttgtctgtaattg | 25 | 61 | 40 | 3024 | 40 |
| Multiplex Subset D6 | | | | | | |
| D13S317.F | tctgacccatctaacgcctat | 21 | 60 | 48 | 89 | 21 |
| D13S317.R | gcccaaaaagacagacagaaaga | 23 | 61 | 43 | 215 | 22 |
| D7S820.F | aggctgactatggagttattttaagg | 26 | 61 | 38 | 45 | 7 |
| D7S820.R | ttatcctcattgacagaattgcac | 24 | 59 | 38 | 264 | 18 |
| TPOX.F | cttcctctgcttcactttcacc | 23 | 63 | 48 | 1691 | 25 |
| TPOX.R' | gctaggcccttctgtcctt | 19 | 62 | 58 | 1957 | 38 |
| TH01.F | ggcaaatagggggcaaaattcaaag | 25 | 63 | 44 | 1093 | 23 |
| TH01.R" | tcacaccacatttcaatcaaggtccat | 27 | 63 | 41 | 1406 | 41 |
| D13S317 Extended Primer Pair Data | | | | | | |
| D13S31.FE* | tgctggacatggtatcacagaagtc | 25 | 65 | 48 | 1 | 42 |
| D13S31.RE* | ttcagagagcttgaattgttggtca | 25 | 61 | 40 | 249 | 43 |

[1]"Amel" is used to abbreviate amelogenin.
Prime (') or double prime (") indicates an alternative primer pair.
FE* represents the forward extended primer.
RE* represents the reverse extended primer.

Compound Multiplexes

To carry out the methods of the present invention, the multiplex subsets are further grouped into combinations of two, three or four, forming compound multiplexes for the purpose of co-amplification in a single vessel and electrophoresis in a single electrophoretic channel. Compound multiplex subsets may also be amplified independently in separate vessels and subsequently combined for electrophoresis in a single channel. Examples of some compound multiplexes which are encompassed by the methods of the present invention are given in Table 3 below. It lists the multiplex subsets forming each compound multiplex, the total number of loci analyzed by the combination, and the number of detectable labels the combination is designed to utilize, thus indicating the number of colors a detection system must be capable of detecting in order to use that combination. In preferred embodiments of the present invention, some compound multiplexes with four subsets can be used to coamplify all thirteen CODIS loci in a single reaction vessel and analyze the amplicons produced in a single electrophoretic channel using a four-color detector. In this case, each multiplex subset within a compound multiplex is labeled with a different detectable label during PCR coamplification.

TABLE 3

Compound Multiplexes

| Compound Multiplex | Subsets | Loci Detected | # of Detectable Labels |
|---|---|---|---|
| I | A1 + B1 + C1 + D1 | 13 CODIS | 4 |
| II | A1 + B1 + C2 + D1 | 13 CODIS and amelogenin | 4 |
| III | A2 + B2 + C3 + D2 | 13 CODIS | 4 |
| IV | A3 + B3 + C4 + D3 | 13 CODIS | 4 |
| V | A3 + B3 + C5 + D3 | 13 CODIS and amelogenin | 4 |

TABLE 3-continued

Compound Multiplexes

| Compound Multiplex | Subsets | Loci Detected | # of Detectable Labels |
|---|---|---|---|
| VI | A4 + B1 + C2 + D3 | 13 CODIS and amelogenin | 4 |
| VII | A1 + B1 | 7 CODIS | 2 |
| VIII | C1 + D1 | 6 CODIS | 2 |
| IX | C2 + D4 | 7 CODIS and amelogenin | 2 |
| X | A1 + C2 | 6 CODIS and amelogenin | 2 |
| XI | B1 + D1 | 7 CODIS | 2 |
| XII | B1 + C2 | 7 CODIS and amelogenin | 2 |
| XIII | C6 + D5 | 6 CODIS and amelogenin | 2 |
| XIV | A1 + B1 + C6 + D5 | 13 CODIS and amelogenin | 4 |
| XV | C7 + D6 | 6 CODIS and amelogenin | 2 |
| XVI | A1 + B1* + C7 + D6 | 13 CODIS and amelogenin | 4 |

*D3S1358 primer pair was replaced by D3S1358' primer pair.

While in preferred embodiments of the present invention, such as compound multiplexes IV and V, subsets are differentially labeled during PCR so that the resulting amplicons can be electrophoresed in a single channel for use with a four-color detection system, those of skill in the art will recognize that such compound multiplexes can also be amplified in 2 PCR, each containing 2 distinctively labeled subsets, such as A3+B3 and C4+D3, for electrophoresis in two channels with a two-color detection system. In addition, a two color system can work by combining compound multiplexes VII and VIII composed of multiplex subsets A1+B1 and C1+D1, respectively. In compound multiplex VII the multiplex subsets A1 and B1 are each differentially labeled in the same PCR with fluorophores detectable by the analytical instrument upon their electrophoresis in a single channel. Subset multiplexes C1 and D1 from compound multiplex VIII are amplified, labeled, and processed in the same manner. Overlapping amplicons are thus distinguished via differential labeling.

Similarly, all thirteen CODIS loci are detected in 2 electrophoretic channels with a two-color instrument by employing either compound multiplexes VII+VIII, VII+IX, X+XI, VII+XIII or VII+XV. Note that compound multiplex III repeats the vWA locus and VII+IX repeats the CSF1PO locus. The inclusion of duplicate loci helps to identify two separate multiplex PCR reactions as originating from the same DNA sample, thus providing a means of verifying that the separated components of the sample are back together; both halves of the sample should contain identical amplified alleles from their duplicated loci. It should also be pointed out that in several compound multiplexes (II, V, VI, IX, XII, XIV, XV and XVI) the amelogenin locus, whose products are sex determinants, could be successfully co-amplified and co-electrophoresed in the same lane with CODIS loci.

In a further embodiment of the present invention, a single color detector may be utilized to detect the amplicons produced by any of the multiplex subsets described in the present invention. In this case, each subset of a compound multiplex is amplified in a different reaction vessel and the same detectable label may be used in each reaction. The resulting amplicons from each reaction are analyzed in different channels of an electrophoretic instrument equipped with a suitable detector.

Primer Selection

In a preferred embodiment of the present invention primers for the thirteen CODIS loci are selected in a manner which avoids the creation of overlapping amplicons within a multiplex subset. The inappropriate selection of primers can produce several undesirable effects, such as lack of reliably detectable amplification from a desired locus, differential amplification of alleles of a locus, amplification at multiple sites, primer dimer formation, undesirable interaction of primer sequences from different loci, production of alleles from one locus which overlap with alleles from another locus, or the need for amplification conditions or protocols for the different loci which are incompatible with multiplex amplification (Walsh, 1992; Edwards, 1994).

The method of the present invention contemplates selecting an appropriate set of primers and amplification protocols which result in the generation of amplified alleles from multiple co-amplified CODIS loci which either do not overlap in size, or may be labeled in some way to make the amplified alleles which do overlap in size distinguishable from one another.

Of particular importance in the practice of the method of this invention is the size range of amplified alleles produced from the individual loci which are amplified together in the multiplex amplification reaction step. For completeness of amplification of forensic samples and ease of analysis with current technologies, systems which can be detected by amplification of fragments up to 400 bp in size are preferred, and fragment sizes less than or equal to 350 bp are most preferred. Examples of preferred embodiments of combinations of loci, primers and amplification techniques which result in the production of amplified alleles in this lower size range are described in the Examples section and the size of the products amplified in the multiplex subsets are listed in Table 1.

Successful combinations of the CODIS STR loci in addition to those disclosed herein can be generated by trial and error of locus combinations, by selection of primer pair sequences, and by adjustment of primer concentrations to identify an equilibrium in which all included loci may be amplified. Therefore, once the method and materials of this invention are disclosed, various methods of selecting loci, primer pairs and amplification techniques for use in the method and kit of this invention are likely to be suggested to one skilled in the art. All such methods are intended to be within the scope of the appended claims.

For example, a new locus can be added to an existing subset to generate a new subset as exemplified in Examples 6 and 7 where the amelogenin locus was added to multiplex subset C1 to form multiplex subset C2. All such subsets which can be generated by the addition of one or more loci to the subsets of the present invention are encompassed by the methods of the present invention, so long as PCR amplification of such subsets results in the generation of amplified alleles from multiple co-amplified CODIS loci which either do not overlap in size, or may be labeled in some way to make the amplified alleles which do overlap in size distinguishable from one another, and the resulting amplicons are ≦450 bps, or more preferably ≦400 bps, or most preferably ≦350 bps.

Similarly, modifications may be made to the primers utilized in the present invention which change the exact sequence of a primer but still allow the primer to function as stipulated in the present invention during PCR amplification. For example, modifications may be made at the 5' or the 3' ends of the primers. This is illustrated in Example 8, where 6 nucleotides were added to the 5' end of the reverse primer for D21S11 in subset A1, generating a new primer as given in subset A2. Also, in Example 13, the forward primer for D21S11 was shortened and the reverse primers for loci D5S818, D18S51, and TPOX were extended at the 5' end, forming primers which were utilized in Compound Multiplex IV. In Example 9, subset B2, both the forward and reverse primers for locus D3S1358 were modified at both the 3' and 5' ends. In each case, the majority of the primer sequences remained the same.

Modifications to the 5' end of a primer may be made, for example, in order to 1) avoid potential overlap of loci, i.e. to "make room" between adjacent loci (loci which run next to each other during electrophoresis) within a multiplex, or 2) in order to adjust the Tm of hybridization. Changes to the 3' end of a primer may be made, for example, in order to 1) reduce the generation of non-specific, artifactual PCR products (the addition of deletion of 1 or 2 bases can make a dramatic difference in terms of hybridization specificity), and 2) in order to take into account the case of a mutation in the DNA sample at the 3' binding site (the 3' end can, for example, be modified as a degenerate primer in order to allow amplification of the mutated allele). Those of skill in the art will recognize that many such changes in the sequences of the primers employed in the practice of the present invention may be made without impairing the utility of the primer in the practice of the present invention. All such changes are intended to be encompassed by the methods of the present invention. Any primers whose sequences are based on the primers disclosed in the present invention (i.e. which have greater than about 65% homology to the primers utilized in the present invention) and which can function as equivalents of the primers actually utilized in the Examples of the present invention (i.e. can be used in a PCR amplification of subsets resulting in the generation of amplified alleles from multiple co-amplified CODIS loci which either do not overlap in size, or may be labeled in some way to make the amplified alleles which do overlap in size distinguishable from one another, and produce amplicons which are $\leq 450$ bps, or more preferably $\leq 400$ bps, or most preferably $\leq 350$ bps in length) are intended to be encompassed by the present invention.

Further, those of skill in the art will recognize that other primers with totally different sequences than those employed in the Examples of the present invention may be employed to effect the PCR amplification of the multiplex subset and the compound multiplex subset groupings of the present invention. All such primers pairs are intended to be covered by the scope of the present invention. Any primer pairs which can be used to PCR amplify the multiplex subsets of the present invention may be used in the practice of the present invention, so long as PCR amplification of the subsets of the present invention results in the generation of amplified alleles from multiple co-amplified CODIS loci which either do not overlap in size, or may be labeled in some way to make the amplified alleles which do overlap in size distinguishable from one another, and the resulting amplicons are $\leq 450$ bps, or more preferably $\leq 400$ bps, or most preferably $\leq 350$ bps in length.

Further, a locus (or multiple loci) may be moved within or between subsets, (with or without concomitant alterations in the sequence of the primers used to amplify the loci of the subset). A locus (or loci) may be omitted from a subset, or loci may be substituted by other appropriate loci, i.e. loci which are also useful for the identification of alleles present in a DNA-containing sample. Additionally, one or more loci may be utilized in more than one subset. Those of skill in the art will recognize that many such arrangements of loci within subsets can be designed which, upon PCR amplification of the subsets so formed, result in the generation of amplified alleles from multiple co-amplified CODIS loci which either do not overlap in size, or may be labeled in some way to make the amplified alleles which do overlap in size distinguishable from one another, and produce amplicons which are $\leq 450$ bps, or more preferably $\leq 400$ bps, or most preferably $\leq 350$ bps in length. All such arrangements are encompassed within the present invention.

Additionally, the primers utilized in the present invention may be modified by the insertion of non-template related nucleotides in order to satisfy certain PCR requirements, such as compatible melting temperatures (Example 16), to minimize primer dimer formation, and to minimize non-locus specific primer binding. All primers generated by such modifications are intended to be encompassed by the present invention so long as PCR amplification of the subsets of the present invention using such primers results in the generation of amplified alleles from multiple co-amplified CODIS loci which either do not overlap in size, or may be labeled in some way to make the amplified alleles which do overlap in size distinguishable from one another, and produces amplicons which are $\leq 450$ bps, or more preferably $\leq 400$ bps, or most preferably $\leq 350$ bps in length.

Synthesis of the primers used in the present invention can be conducted using any standard procedure for oligonucleotide synthesis. Many such procedures are well-known to those skilled in the art and are suitable for use in the practice of the present invention.

Preparation of DNA Samples

Those of skill in the art will recognize that the DNA samples to be analyzed by the method of the present invention may come from any of a wide variety of sources, including but not limited to blood, semen, vaginal cells, hair, saliva, urine, placental cells, fetal cells, buccal cells, and the like.

Samples of human genomic DNA can be prepared for use in the method of this invention using any method of DNA preparation which is compatible with the amplification of a single locus. Many suitable methods are known to those of skill in the art and include, but are not limited to, DNA sample preparation as described by Pate, et al. (1984) "Organization of the HPRT gene and related sequences in the human genome, *Somat. Cell Mol. Genet.* 10:483–493; and Gill et al., (1985) "Forensic Application of DNA 'Fingerprints'," *Nature* 318:577–579.

DNA concentrations can be measured prior to use in the method of the present invention using any standard method of DNA detection. In a preferred embodiment of the present invention, the DNA concentration is measured fluorometrically using a technique such as that described by Brunk et al. (1979) "Assay for nanogram quantities of DNA in cellular homogenates," *Anal. Biochem.* 92:497–500. In another preferred embodiment, the DNA concentration is measured by comparison of the amount of hybridization of DNA standards with a human-specific probe such as that described by Waye et al. (1991) "Sensitive and specific quantitation of human genomic deoxyribonucleic acid (DNA) in forensic science specimens: casework examples," *J. Forensic Sci.* 36:1198–1203. The use of too much template DNA in the amplification reactions can produce artifacts which appear as "extra" bands, and which may be confused with true alleles.

PCR Amplification of DNA

Once a sample of human genomic DNA is isolated and its concentration determined as described above, the targeted loci can be co-amplified in the multiplex amplification steps of the present invention. Many different amplification methods are well-known to those of skill in the art and can be used to amplify the loci by the method of the present invention, including but not limited to, the method described by Saiki et al. (1985) "Enzymatic amplification of beta-globin genomic sequences and restriction site analysis for diagnosis of sickle cell anemia," *Science* 230:1350–1354. In a preferred embodiment of the present invention, the DNA sample is subjected to PCR amplification using primer pairs and thermocycling conditions specific to each locus in the set. Reference is made to the Sequence Listing at the end of this specification for details of the primer sequences used in the Examples below.

Details of the most preferred amplification protocol for each of the most preferred combinations of loci for use in the method of this invention are given in the Examples below. Reference is also made to the Examples for additional details of the specific procedure relating to each multiplex. The sequences of the locus-specific primers used in the examples include a number of nucleotides which, under the conditions used in the hybridization, are sufficient to hybridize with an allele of the locus to be amplified and to be essentially free from amplification of alleles of other loci. U.S. Pat. No. 5,192,659 to Simons, the teaching of which is incorporated herein by reference, provides a detailed description of locus-specific primers.

In the most preferred embodiments of the present invention, the selection of primers and the PCR amplification protocol has been worked out so that all thirteen CODIS loci, with or without the amelogenin locus, can be simultaneously amplified using the same protocol (i.e. same temperatures for each step of denaturation, annealing and elongation) so that the amplification will result in the production of a sufficient concentration of amplicons for each locus.

Separation and Detection of DNA Fragments

Once a set of amplified alleles has been produced from the multiplex amplification step of the present method, the amplified alleles are separated and evaluated. A number of suitable means for separation are well-known to those of skill in the art and include but are not limited to polyacrylamide gel electrophoresis, and capillary electrophoresis.

In a preferred embodiment of the present invention, the products of the multiplex amplification reaction are separated by electrophoresis. Preferred gel preparation and electrophoresis procedures and conditions for use in the evaluating step of the method of this invention are described below in the Methods section, and may be carried out by either denaturing slab gel or capillary electrophoresis systems. Identification of the separated allelic fragments then occurs based on fragment size.

In a preferred embodiment of the present invention, the electrophoresis of all thirteen CODIS loci, (and optionally, amelogenin) plus corresponding LSB molecular weight markers, is carried out in a single electrophoretic channel. However, one of skill in the art will recognize that analysis of the multiplex groupings of the present invention may be carried out by electrophoresis in a plurality of channels, if desired.

Once the amplified alleles are separated in a slab gel or capillary electrophoresis system, the alleles and any other DNA (e.g. DNA markers or an allelic ladder) can then be analyzed. Detection of separated DNA fragments can be accomplished using any one of a number of techniques which are well-known to those of skill in the art. These include but are not limited to silver staining, using reporters such as radioisotopes, fluorophores, chemiluminescers and enzymes in combination with detectable substrates, and the like.

In a preferred embodiment of the present invention, the method of detection is via the use of fluorescently-labeled (Ziegle et al., 1992) primers for each locus in the multiplexing reaction followed by detection of the labeled products using a fluorometric detector.

The alleles present in the DNA sample are preferably determined by comparison of their electrophoretic migration to that of calibration standards. of known length to determine the allelic fragment lengths present at each locus within the sample. In a preferred embodiment of the present invention, the size markers for evaluation of multiplex amplification containing the 13 CODIS polymorphic STR loci consists of Locus Specifics Brackets (LSB) for each of the loci being evaluated. LSB are a new type of lane standard with electrophoretic mobility compatible with that of the alleles of the locus they are designed to bracket (Dau, 1997).

The preferred size marker for evaluation of a multiplex amplification containing two or more CODIS STR loci which are generated using fluorescently-labeled primers for each locus consists of a combination of fluorescently-labeled LSB for the loci being evaluated. Following the construction of LSB for individual loci, they may be mixed and loaded for gel electrophoresis at the same time as the loading of amplified samples occurs. Each pair of LSB co-migrates in register with the alleles of its locus of origin within the electrophoretic channel and may be employed together with MM in the same internal lane. LSB may also be employed as external calibration standards, with or without MM or allelic calibration standards.

However, those of skill in the art will recognize that the amplicons produced by PCR amplification of the multiplex groupings of the present invention may be analyzed in comparison to other molecular weight markers as well. Any molecular weight markers which provide sensitive and accurate determination of the molecular weight of the amplicons may be used in the practice of the present invention.

Detection of Amplified Alleles

In a preferred embodiment of the present invention, fluorescence detection is utilized to evaluate the amplified alleles in the mixture produced by the multiplex amplification reaction. Below is a summary of how that method of detection is preferably practiced.

With automated fluorescent imaging, rapid detection and analysis of multiplex amplification products can be achieved. For fluorescent analyses, one fluoresceinated primer can be included in the amplification reaction of each locus. A single strand of DNA, either sense or antisense, will then be labeled at each locus by PCR. Separation of the amplified fragments produced using labeled primers may then be achieved by electrophoresis, and the labeled strand from each locus can be detected by its fluorescent emission upon excitation by photons of the appropriate wavelength post-electrophoresis. The gel can be analyzed by, for example, a FluorImager™ analyzer (from Molecular Dynamics, Sunnyvale, Calif.) or FMBIO™ (Hitachi Corp., San Bruno, Calif.), which can scan the gel, locate and measure the distance of migration of the DNA fragments.

Alternatively, measurements can be made in real time during an electrophoresis run as each labeled DNA molecule is excited by a laser beam during migration near the end of its channel, and its running time is recorded, for example with the ALF, ALFexpress, VGI Microgene Clipper, or ABI Prism™ analyzer. Under denaturing conditions, fragment length is proportional to run time, and can be calculated from the sample and calibration standard run times and known calibration fragment lengths. Preferably, LSB are employed as calibration standards for each locus to be measured, and the size of each locus-specific amplified fragment is described by a formula relating it to the known lengths of its LSB (Dau, U.S. Pat. No. 6,013,444).

In summary, in a preferred embodiment of the present invention, the method of detection of the evaluating step is fluorescence detection. In this preferred method of detection, one of each pair of primers used in the multiplex amplification reaction has a fluorescent label covalently attached thereto, and as a result one strand of DNA from each of the amplified alleles produced in the amplification reaction is fluorescently labeled. In this embodiment of the invention, the amplified alleles are subsequently separated on a denaturing polyacrylamide gel and the labeled DNA strand of each allele is visualized and analyzed online using a fluorescence detector. Additionally, the use of multiple fluorophores allows the detection in a single electrophoretic channel of alleles from STR loci which potentially overlap in fragment length.

Kit

The present invention is also directed to kits that utilize the processes described above. A basic kit comprises a container having one or more locus-specific primer pairs for each locus. Instructions for use of the kit may optionally be included.

Other optional kit components include LSB for each of the specified loci, other heterologous multiplex markers or allelic calibration standards and a sufficient quantity of enzyme for amplification, amplification buffer, loading solution for preparation of the amplified material for gel electrophoresis, human genomic DNA as a template control, and a protocol and manual to educate the user. The amounts of the various reagents in the kits also can be varied depending upon a number of factors, such as the optimum sensitivity of the process. It is within the scope of the present invention to provide test kits for use in manual applications or test kits for use with automated detectors or analyzers.

Method for Utilization of Internal and External Lane Standards

The present invention also encompasses a method for the highly accurate measurement of the length of the alleles of a genetic locus by utilizing simultaneously both internal and external lane standards.

In a preferred embodiment of this aspect of the invention, the internal lane standards are LSB for the locus and the external lane standards comprise LSB for the locus plus at least one allele of known length (true allele) from the locus. In a most preferred embodiment, the external standards consist of LSB and two alleles from each locus, and preferably, the two alleles from each locus are evenly distributed (equidistant) between their LSB.

Those of skill in the art will recognize that other combinations of internal and external lane calibration standards may also be used in the practice bf the present invention. Examples of other combinations of internal and external lane calibration standards include but are not limited to: bracketing MM as internal lane standards, and LSB combined with at least one true allele and bracketing MM as external lane standards, bracketing MM as internal lane standards, and bracketing MM and locus specific allelic ladders as external lane standards; and bracketing MM as internal lane standards, and bracketing MM and locus specific allelic ladders plus LSB as external lane standards. Any appropriate combination of internal and external lane calibration standards may be used in the practice of the present invention.

By "bracketing MM" we mean non-overlapping MM which bracket the sample alleles being measured. The MM may, for example, bracket or partially bracket the alleles of individual loci being analyzed, and/or the MM may bracket the shortest and longest alleles of all alleles being measured in their electrophoretic channel. In any case, the MM do not overlap the expected fragment length range of the alleles being measured.

According to the method of the present invention, the initial electrophoretic run times of the PCR amplicons of the locus and the internal and external lane calibration standards are determined as described. The initial run times values for the internal and external lane calibration standards are used to construct an external standard curve. In a preferred embodiment of the present invention, such an external standard curve may be defined by piece-wise third order polynomials using, for example, Equation 1:

$$P(x)=P_0+(P_1*x)+(P_2*x^2)+(P_3*x^3)$$

where "x" is the run time in minutes, as described in ALFwin™ Fragments Analyser 1.00 User Manual, edition AA (Amersham Pharmacia Biotech) page C-9, section C.3.1. Those of skill in the art will be well-acquainted with the generation of standard curves using such equations.

The lengths of the alleles of the locus under analysis is ultimately determined by plotting the run times of the amplicons of the locus against the standard curve. However, use of the internal standards allows for adjustments of the standard curve, or calibration of the run times of the amplicons, or both, in order to increase the accuracy of the measurement. Such adjustment and/or calibration compensates for lane-to-lane variations in run times due to non-uniform electrophoresis conditions (e.g. small deviations in the thickness of the gel, temperature across the gel, etc.).

Thus, in one embodiment of the present invention, the standard curve itself may be adjusted in order to account for the mobility of corresponding internal standards. For example, an "offset value" (described in more detail below) may be calculated as the average difference between standards run simultaneously in internal and external lanes, and may be applied to each standard value to adjust its position in generating the external lane curve.

Alternatively, or in addition, the initial run times of the PCR amplicons of the locus being analyzed may be calibrated. In one embodiment of the present invention, the calibration may be carried out in the following manner:

1) the initial run time of an internal standard short LSB as measured in the lane with the amplicons (the sample channel) is subtracted from the initial run time of an external standard short LSB as measured in the external standard lane, yielding a short LSB "difference value".

2) The initial run time of an internal standard long LSB as measured in the lane with the amplicons (the sample channel) is subtracted from the initial run time of an external standard long LSB as measured in the external standard lane, yielding a long LSB "difference value".

3) The long LSB and short LSB difference values are averaged to obtain an "offset value".

4) The offset value is added to the initial measured run time of each amplicon, producing an adjusted run time value.

5) The adjusted run time values of the amplicons are plotted against the standard curve generated as described above in order to determine the allele length.

Those of skill in the art will recognize that other ways of adjusting the external standard curve and/or calibrating the run times of PCR amplicons with respect to the run times of the internal standards exist or may be developed which may also be utilized in the practice of the method of the present invention. All such ways of adjusting external standard curves and calibrating amplicon run times are intended to be encompassed by the method of the present invention. Further, the invention also contemplates software capable of carrying out the necessary calculations.

Accommodation for the Measurement of Rare Alleles

In order to obtain accurately measured PCR amplicons of <350 bp in length from rare (Griffiths, 1998) in addition to common alleles from the FGA locus, more room needed to be created within its subset to allow a detection range adequate to encompass the entire polymorphism. Thus, another embodiment of the present invention is found in Examples 32–43, where measurement of such rare alleles is illustrated.

Sequences

The present invention also provides two novel DNA sequences represented by SEQ ID 43 and SEQ ID 44. SEQ ID 43 is the first correct sequence of locus D13S317 (see *2 footnote of Table 2) ever to be published. The sequence given for locus D13S317 in the Gene Bank database and which is relied upon by other forensic testing methods is incorrect: only one "AATC" sequence is listed after the repeats, however two AATC sequences are actually present. The two repeats are indicated in bold in footnote *2 of Table 1. SEQ ID 44 represents the previously unpublished repeat and flanking sequences of locus D3S1358 (see *1 footnote of Table 1).

The sequence data revealed in the present application from both of these loci is novel and useful for a variety of purposes in the area of human genetic identification. In particular, the sequences are useful in forensic testing and paternity testing. However, those of skill in the art will recognize that many other specific uses for the sequences in the field of human genetic identification exist. All such uses are intended to be within the scope of the present invention.

EXAMPLES

Methods

A human genomic DNA template, NA09947A (NIGMS Human Genetic Mutant Cell Repository, Coriell Institute for Medical Research, Camden, N.J.), was amplified simultaneously by PCR at the loci indicated in each example in a single reaction vessel. Taq DNA Polymerase and its 10× buffer (Boehringer Mannheim Corporation, Indianapolis, Ind.) were used in the amplification reaction. 10× buffer includes 100 mM Tris-HCl and 15 mM MgCl, pH 8.3 (20° C.). For electrophoresis with the ALFexpress, PCR was performed in a total volume of 10 µl, including 0.5 µl (100 ng/µl) DNA template, 1.0 µl 10× buffer, 0.15 µl Taq DNA Polymerase (5 U/µl), 0.15 µl 10 mM dNTPs (Ultrapure Solution dNTPs, Amersham Pharmacia Biotech Inc., Piscataway, N.J.), and 1.0 µl of a 10× primer mixture at the concentration given in each example. In PCR reactions where the amplicon fragment length was to be measured, Pfu DNA polymerase was used instead of Taq DNA polymerase in order to avoid variable "extra A" nt addition by Taq. Coriell DNA template NA09948A and DNA from the K562 human cell line were tested in addition to Coriell NA09947A in order to determine the accuracy of fragment length measurement with LSB. Water was added to bring the final volume to 10 µl. One primer of each pair was labeled with the Cy5 fluorophore. 25 µl of mineral oil, molecular biology grade (Sigma Chemical Co., St. Louis, Mo.), was laid on top of the reaction.

A Thermal Cycler 480 (Perkin Elmer, Foster City, Calif.) was employed with the following amplification protocol:

94° C. for 5 minutes, followed by a first cycle of: 94° C. for 30 seconds, 71° C. (annealing temperature) for 45 seconds, and 72° C. for 45 seconds. The first cycle of PCR is then repeated except that the annealing temperature of each successive cycle set 1° C. lower than the preceding cycle, until the annealing temperature is reduced to 57–63° C. Twenty-five to thirty additional cycles of the last PCR cycle (i.e. 57° C. annealing temperature) are then performed, followed by a 10 minute extension at 72° C., and finally cooling at 40° C.

To separate the PCR products by DNA fragment length with the ALFexpress, the sample PCR amplicons were labeled with a single fluorophore, electrophoresed in 0.5 mm thick, denaturing 6% polyacrylamide gels (Long Ranger PreMix solution, FMC Bioproducts, Rockland, Me.) with a fluorescent automated DNA sequencer (ALFexpress, Amersham Pharmacia Biotech). From 0.5 to 3 µl of the PCR reaction mix was loaded per channel. This amount can vary, depending on the detection system used, the size of the channel, etc. The settings for the ALFexpress were: 1500 V, 60 mA, 55V C., 3 mW of laser power, and 2 sec sampling interval. Two LSB DNA size markers made in our own laboratory, of 101 and 335 bp were loaded in each sample containing lane. The fluorescent signal from PCR products was analyzed by Fragment Manager™ 1.2 software (Amersham Pharmacia Biotech, Piscataway, N.J.).

In order to sequence DNA molecules, their PCR amplicons were first cloned into the vector according to the PCR-Script™ Amp cloning Kit instruction manual (Stratagene, La Jolla, Calif.). Sequencing reactions were performed with dye terminator chemistry according to the technical manual for the fmol® DNA System (Promega, Madison, Wis.). Subsequent electrophoresis and sequence analysis were carried out automatically on the ALFexpress instrument.

To separate PCR products by DNA fragment length employing the Prizm 310 analyzer for samples labeled with multiple fluorophores, LSB were added to some samples just prior to electrophoresis in order to determine their accuracy in calibration of CODIS target alleles as previously demonstrated for other STR loci (Dau, U.S. Pat. No. 6,013,444).

Fluorophores utilized as indicated in the Examples were: Cy5 (indodicarbocyanine), 5-FAM (5-carboxy-fluorescein), TAMRA (tetramethyl-6-carboxyrhodamine), JOE (6-carboxy-4',5'-dichloro-2',7'-dimethoxy fluorescein), and ROX (6-carboxy-X-rhodamine).

Example 1

Amplification and Electrophoresis of Multiplex Subset A1 Loci vWA, D21S11, and D18S51

This example demonstrates that triplex subset, vWA, D21S11 and D18S51, can be co-amplified from genomic DNA by its PCR primers labeled with a common fluorophore (Cy5) and co-electrophoresed in a single gel lane without overlap, as judged by their relative position expected amplicon fragment length ranges (Table 1). In this example, PCR, electrophoretic conditions and data analysis were carried out as described in Methods. The last 25 cycles of PCR were performed at a constant annealing temperature of 61° C. The loci in this example were amplified in a single PCR vessel in a total 10 µl reaction volume and their PCR amplicons were analyzed in a single electrophoretic gel lane on ALFexpress. The final primer concentrations in this PCR for each locus were: 1.2 µM each of vWA primers 1 [SEQ ID NO: 1] and 2 [SEQ ID NO: 2], 0.3 µM each of D21S11 primers 1 [SEQ ID NO: 3] and 2 [SEQ ID NO: 4], and 0.3 µM each of D18S51 primers 1 [SEQ ID NO: 5] and 2 [SEQ ID NO: 6]. Reference is made to FIG. 1 which displays the amplified DNA fragments from each locus according to their size (nt) dependent migration in a single gel lane. Individual fragments are identified by the length of the expected amplicons from their locus.

Figure 2:
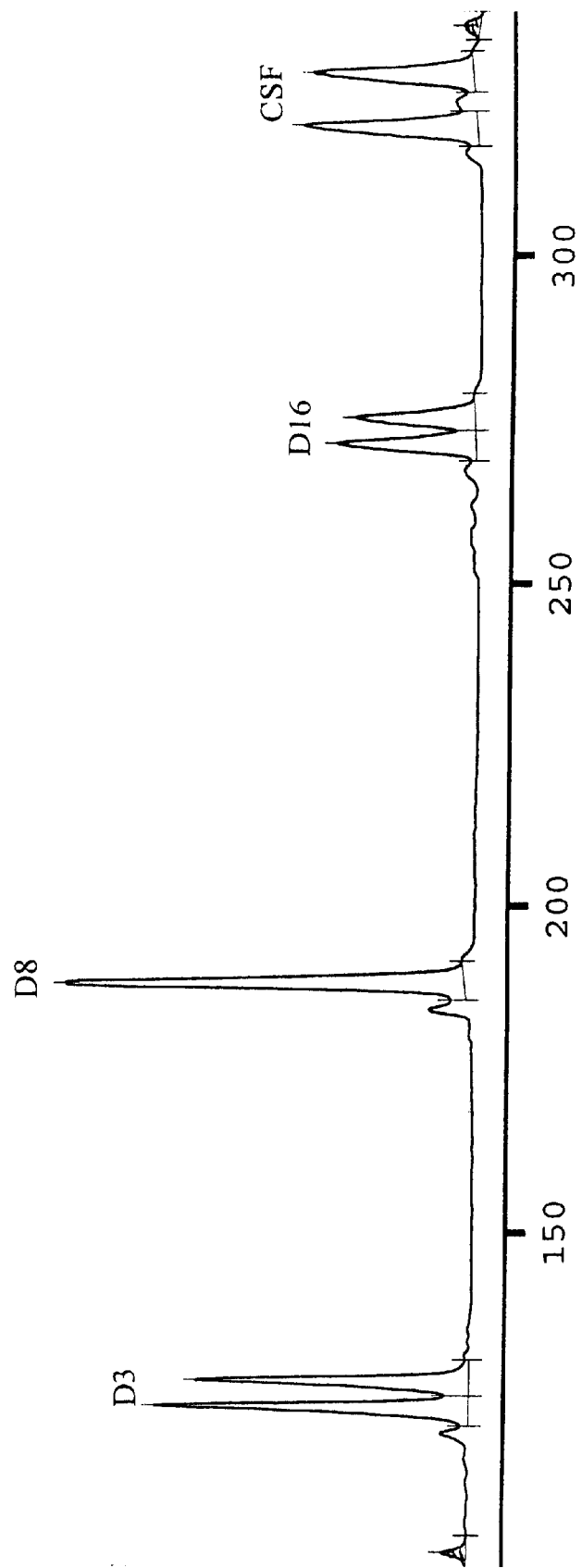
FIG. 2 is a printed image from the ALFexpress automated sequencer (Amersham Pharmacia Biotech) showing the fluorescent detection upon electrophoresis of the PCR product after amplification of the loci from multiplex subset B1: D3S1358, D8S1179, D16S539, and CSF1PO. Peak areas correspond to fluorescence intensity and are depicted graphically as a function of fragment length (nt). Fluorescent peaks measured at 101 and 335 nt represent the DNA size standards.

Example 2
Amplification and Electrophoresis of Multiplex Subset B1 Loci D3S1358, D8S1179, D16S539, and CSF1PO This example demonstrates that quadriplex subset, D3S1358, D8S1179, D6S539, and CSF1PO, can be co-amplified from genomic DNA by its PCR primers labeled with a common fluorophore (Cy5) and co-electrophoresed in a single gel lane without overlap, as judged by their relative position expected amplicon fragment length ranges (Table 1). In this example, PCR, electrophoretic conditions and data analysis were carried out as described in Methods. The last 25 cycles of PCR were performed at a constant annealing temperature of 61° C. The loci in this example were amplified in a single PCR vessel in total 10 µl reaction volume and their PCR amplicons were analyzed in a single electrophoretic gel lane on ALFexpress. The final primer concentrations in this PCR were: 0.3 µM each of D3S1358 primers 1 [SEQ ID NO: 7] and 2 [SEQ ID NO: 8], 0.6 µM each of D8S1179 primers 1 [SEQ ID NO: 9] and 2 [SEQ ID NO: 10], 0.6 µM each of D16S539 primers 1 [SEQ ID NO: 11] and 2 [SEQ ID NO: 12], and 0.3 µM each of CSF1PO primers 1 [SEQ ID NO: 13] and 2 [SEQ ID NO: 14]. Reference is made to FIG. 2 which displays the amplified DNA fragments from each locus according to their size (nt) dependent migration in a single gel lane. Individual fragments are identified by the length of the expected amplicons from their locus.

Figure 3:
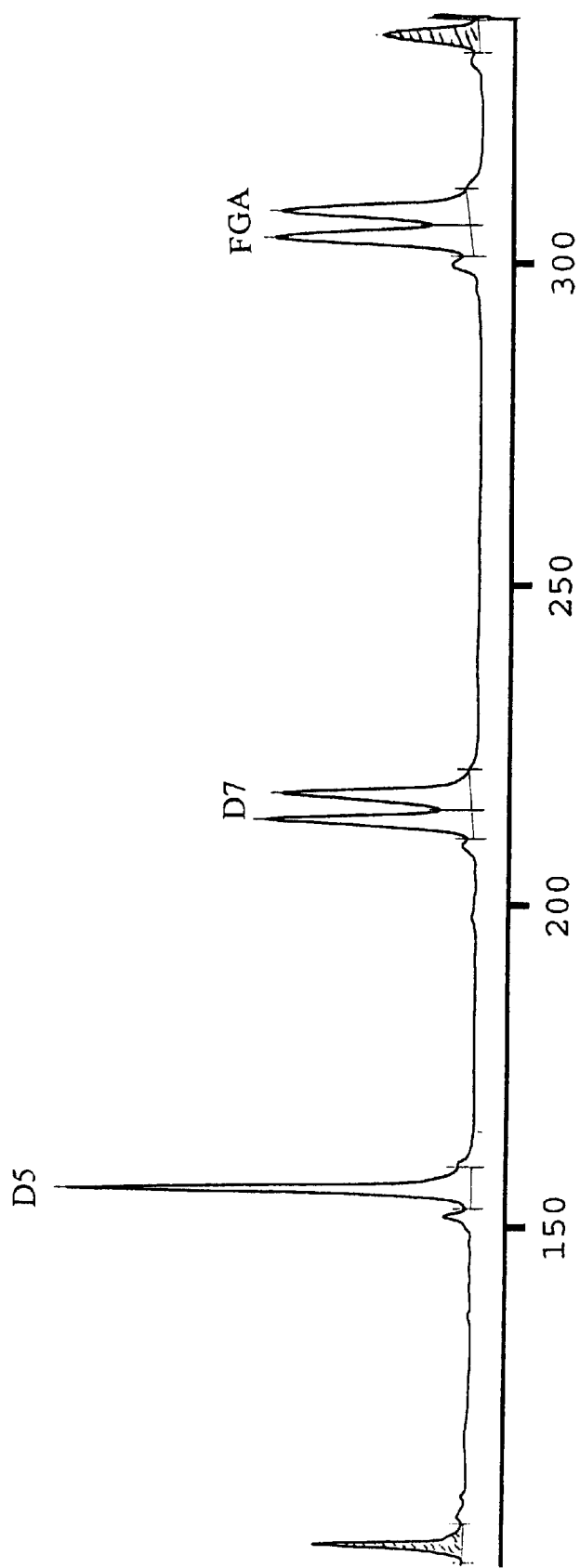
FIG. 3 is a printed image from the ALFexpress automated sequencer (Amersham Pharmacia Biotech) showing the fluorescent detection upon electrophoresis of the PCR product after amplification of the loci from multiplex subset C1: D5S818, D7S820, and FGA. Peak areas correspond to fluorescence intensity and are depicted graphically as a function of fragment length (nt). Fluorescent peaks measured at 101 and 335 nt represent DNA size standards.

Example 3
Amplification and Electrophoresis of Multiplex Subset C1 Loci D5S818, D7S820, and FGA This example demonstrates that triplex subsets D5S818, D7S820, and FGA, can be co-amplified from genomic DNA by its PCR primers labeled with a common fluorophore (Cy5) and co-electrophoresed in a single gel lane without overlap, as judged by their relative position expected amplicon fragment length ranges (Table 1). In this example, PCR, electrophoretic conditions and data analysis were carried out as described in Methods. The last 25 cycles of PCR were performed at a constant annealing temperature of 61° C. The loci in this example were amplified in a single PCR vessel in total 10 µl reaction volume and their PCR amplicons were analyzed in a single electrophoretic gel lane on ALFexpress. The final primer concentrations in this PCR for each locus were: 0.3 µM each of DSS818 primers 1 [SEQ ID NO: 15] and 2 [SEQ ID NO: 16], 0.96 µM each of D7S820 primers 1 [SEQ ID NO: 17] and 2 [SEQ ID NO: 18], and 0.6 µM each of FGA-primers 1 [SEQ ID NO: 19] and 2 [SEQ ID NO: 20]. Reference is made to FIG. 3 which displays the amplified DNA fragments from each locus according to their size (nt) dependent migration in a single gel lane. Individual fragments are identified by the length of the expected amplicons from their locus.

Figure 4:
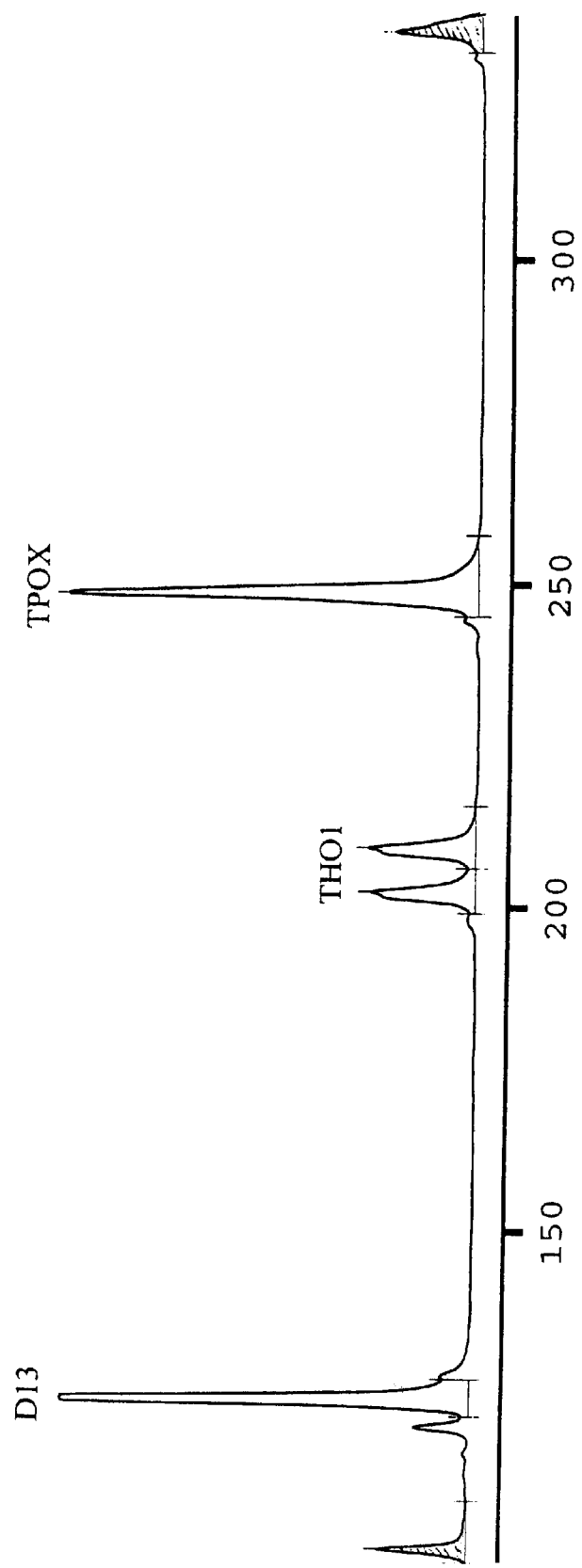
FIG. 4 is a printed image from the ALFexpress automated sequencer (Amersham Pharmacia Biotech) showing the fluorescent detection upon electrophoresis of the PCR product after amplification of the loci from multiplex subset D1: D13S317, TH01, and TPOX. Peak areas correspond to fluorescence intensity and are depicted graphically as a function of fragment length (nt). Fluorescent peaks measured at 101 and 335 nt represent DNA size standards.

Example 4
Amplification and Electrophoresis of Multiplex Subset D1 Loci D13S317, TH01, and TPOX This example demonstrates that triplex subset D13S317, TH01, and TPOX can be co-amplified from genomic DNA by its PCR primers labeled with a common fluorophore (Cy5) and co-electrophoresed in a single gel lane without overlap, as judged by their relative position and expected amplicon fragment length ranges (Table 1). In this example, PCR, electrophoretic conditions and data analysis were carried out as described in Methods. The last 25 cycles of PCR were performed at a constant annealing temperature of 61° C. The loci in this example were amplified in a single PCR vessel in total 10 µl reaction volume and their PCR amplicons were analyzed in a single electrophoretic gel lane on ALFexpress. The final primer concentrations in this PCR for each locus were: 0.09 µM each of D13S317 primers 1 [SEQ ID NO: 21] and 2 [SEQ ID NO: 22], 0.6 µM each of TH01 primers 1 [SEQ ID NO: 23] and 2 [SEQ ID NO: 24], and 0.05 µM each of TPOX primers 1 [SEQ ID NO: 25] and 2 [SEQ ID NO: 26]. Reference is made to FIG. 4 which displays the amplified DNA fragments from each locus according to their size (nt) dependent migration in a single gel lane. Individual fragments are identified by the length of the expected amplicons from their locus.

Figure 5:
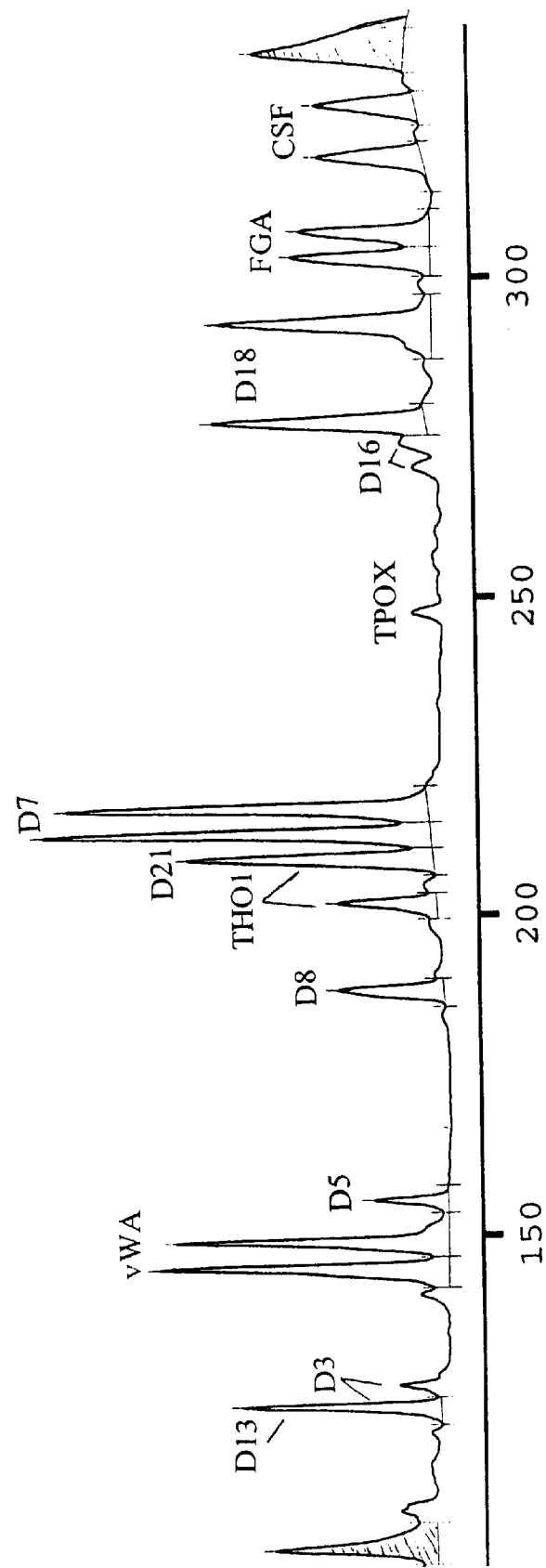
FIG. 5 is a printed image from the ALFexpress automated sequencer (Amersham Pharmacia Biotech) showing the fluorescent detection upon electrophoresis of the PCR product after amplification of the loci from Compound Multiplex I, subsets A1+B1+C1+D1: vWA, D21S11, D18S51, D3S1358, D8S1179, D16S539, CSF1PO, D5S818, D7S820, FGA, D13S317, TH01 and TPOX. Peak areas correspond to fluorescence intensity and are depicted graphically as a function of fragment length (nt). Fluorescent peaks measured at 101 and 335 nt represent DNA size standards.

Example 5
Amplification and Electrophoresis of Compound Multiplex I: A1 Loci vWA, D21S11, and D18S51; B1 Loci D3S1358, D8S1179, D16S539, and CSF1PO; C1 Loci D5S818, D7S820, and FGA; and D1 Loci D13S317, TH01, and TPOX This example demonstrates that subsets A1, B1, C1 and D1 can be co-amplified from genomic DNA by their PCR primers labeled with a common fluorophore (Cy5) and co-electrophoresed in a single gel lane. Alleles were judged by their relative position and expected amplicon fragment length ranges (Table 1). In this example, PCR, electrophoretic conditions and data analysis were carried out as described in Methods. The last 25 cycles of PCR were performed at a constant annealing temperature of 61° C. The loci in this example were amplified in a single PCR vessel in total 10 µl reaction volume and their PCR amplicons were analyzed in a single electrophoretic gel lane on ALFexpress. The final primer concentrations in this PCR for each locus were: 0.15 µM each of vWA primers 1 [SEQ ID NO: 1] and 2 [SEQ ID NO: 2], 0.11 µM each of D21S11 primers 1 [SEQ ID NO: 3] and 2 [SEQ ID NO: 4], and 0.08 µM each of D18S51 primers 1 [SEQ ID NO: 5] and 2 [SEQ ID NO: 6], 0.12 µM each of D3S1358 primers 1 [SEQ ID NO: 7] and 2 [SEQ ID NO: 8], 0.15 µM each of D8S1179 primers 1 [SEQ ID NO: 9] and 2 [SEQ ID NO: 10], 0.1875 µM each of D16S539 primers 1 [SEQ ID NO: 11] and 2 [SEQ ID NO: 12], and 0.075 µM each of CSF1PO primers 1 [SEQ ID NO: 13] and 2 [SEQ ID NO: 14], 0.11 µM each of D5S818 primers 1 [SEQ ID NO: 15] and 2 [SEQ ID NO: 16], 0.225 µM each of D7S820 primers 1 [SEQ ID NO: 17] and 2 [SEQ ID NO: 18], and 0.1875 µM each of FGA primers 1 [SEQ ID NO: 19] and 2 [SEQ ID NO: 20], 0.045 µM each of D13S317 primers 1 [SEQ ID NO: 21] and 2 [SEQ ID NO: 22], 0.225 µM each of TH01 primers 1 [SEQ ID NO: 23] and 2 [SEQ ID NO: 24], and 0.06 µM each of TPOX primers 1 [SEQ ID NO: 25] and 2 [SEQ ID NO: 26]. The results are shown in FIG. 5. All alleles of the 13 CODIS loci are readily identifiable as peaks of the expected amplicon fragment length corresponding to those found in their multiple subsets shown in FIGS. 1–4. Overlapped alleles from different subsets are differentially displayed by peak area (homogenous alleles from D13S317 overlapping with the first allele of D3S1358 and homogenous alleles of D21S11 overlapping with the second allele of TH01).

Figure 6:
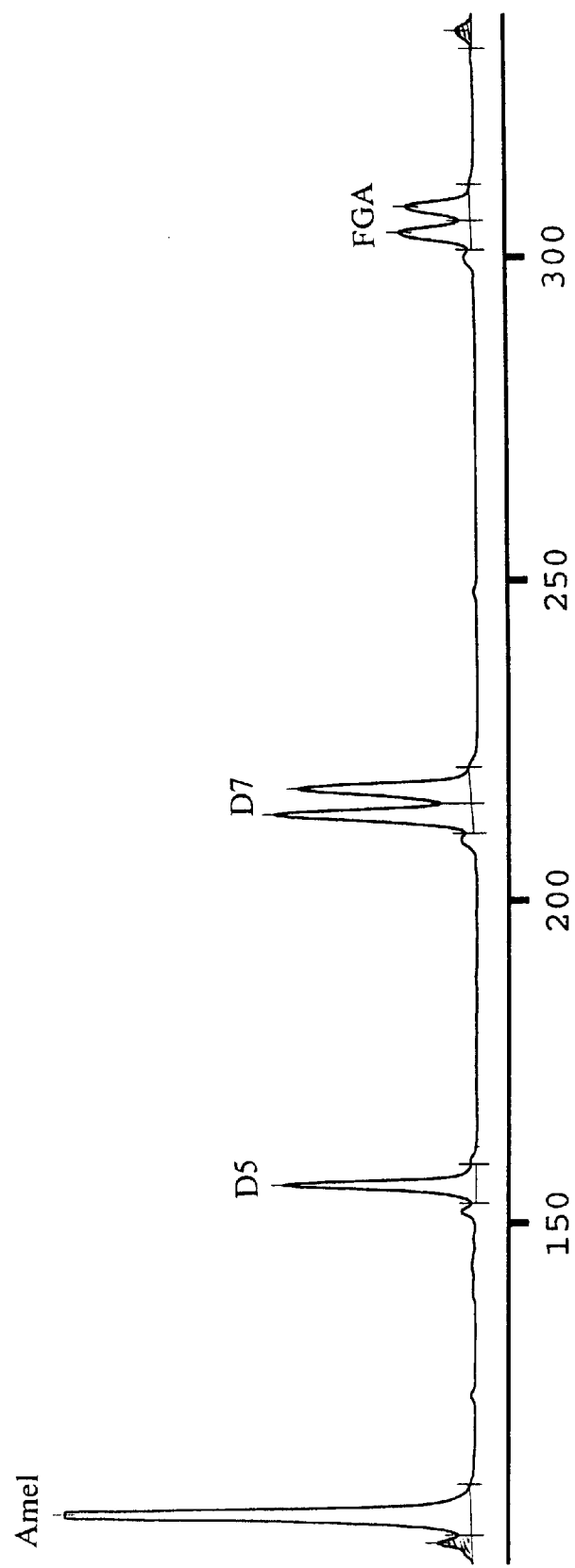
FIG. 6 is a printed image from the ALFexpress automated sequencer (Amersham Pharmacia Biotech) showing the fluorescent detection upon electrophoresis of the PCR product after amplification of the loci from multiplex, subset C2: amelogenin, D5S818, D7S820 and FGA. Peak areas correspond to fluorescence intensity and are depicted graphically as a function of fragment length (nt). Fluorescent peaks measured at 101 and 335 nt represent DNA size standards.

Example 6
Amplification and Electrophoresis of Multiplex Subset C2 Loci Amelogenin, D5S818, D7S820, and FGA This example demonstrates that the locus amelogenin can be added to multiplex subset C1 without interfering with identification of other alleles. In this example, PCR, electrophoresis conditions and data analysis were carried out as described in Methods. The last 25 cycles of PCR were performed at a constant annealing temperature of 61° C. The loci in this example were amplified in a single PCR vessel in total 10 µl reaction volume and their PCR amplicons were analyzed in a single electrophoretic gel lane on ALFexpress. The final primer concentrations in this PCR for each locus were: 0.21 µM each of Amelogenin primers 1 [SEQ ID NO: 27] and 2 [SEQ ID NO: 28], 0.3 µM each of D5S818 primers 1 [SEQ ID NO: 15] and 2 [SEQ ID NO: 16], 0.96 µM each of D7S820 primers 1 [SEQ ID NO: 17] and 2 [SEQ ID NO: 18], and 0.6 µM each of FGA primers 1 [SEQ ID NO: 19] and 2 [SEQ ID NO: 20]. Reference is made to FIG. 6 which displays the amplified DNA fragments from each locus according to their size (nt) dependent migration in a single gel lane. Individual fragments are identified by the length of the expected amplicons from their locus.

Figure 7:
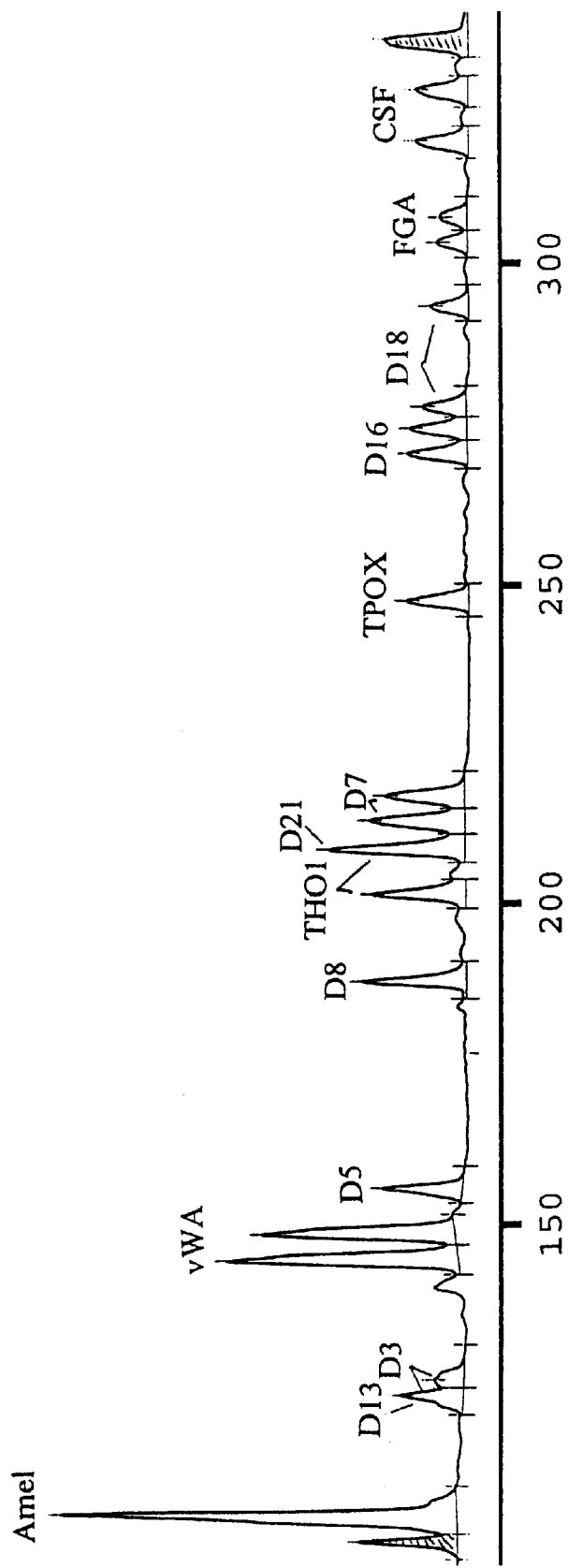
FIG. 7 is a printed image from the ALFexpress automated sequencer (Amersham Pharmacia Biotech) showing the fluorescent detection upon electrophoresis of the PCR product after amplification of the loci from Compound Multiplex II, subsets A1+B1+C2+D1: vWA, D21S11, D18S51, D3S1358, D8S1179, D16S539, CSF1PO, amelogenin, D5S818, D7S820, FGA, D13S317, TH01, and TPOX. Peak areas correspond to fluorescence intensity and are depicted graphically as a function of fragment length (nt). Fluorescent peaks measured at 101 and 335 nt represent DNA size standards.

Example 7
Compound Multiplex II: Amplification and Electrophoresis of Amelogenin Locus with the Thirteen CODIS Loci In compound multiplex II, original subset C1 was replaced by subset C2 so that amelogenin was co-amplified with other CODIS 13 loci. In this example, PCR, electrophoretic conditions and data analysis were carried out as described in Methods. The last 25 cycles of PCR were performed at a constant annealing temperature of 61° C. Subset A1, B1, C2, and D1 loci were amplified in a single PCR vessel in total 20 µl reaction volume and their PCR amplicons were analyzed in a single electrophoretic gel lane on ALFexpress. The final primer concentrations in this PCR for each locus were: 0.83 µM each of vWA primers 1 [SEQ ID NO: 1] and 2 [SEQ ID NO: 2], 0.17 µM each of D21S11 primers 1 [SEQ ID NO: 3] and 2 [SEQ ID NO: 4], and 0.08 µM each of D18S51 primers 1 [SEQ ID NO: 5] and 2 [SEQ ID NO: 6], 0.17 µM each of D3S1358 primers 1 [SEQ ID NO: 7] and 2 [SEQ ID NO: 8], 0.41 µM each of D8S1179 primers 1 [SEQ ID NO: 9] and 2 [SEQ ID NO: 10], 0.40 µM each of D16S539 primers 1 [SEQ ID NO: 11] and 2 [SEQ ID NO: 12], and 0.11 µM each of CSF1PO primers 1 [SEQ ID NO: 13] and 2 [SEQ ID NO: 14], 0.08 µM each of Amelogenin primers 1 [SEQ ID NO: 27] and 2 [SEQ ID NO: 28], 0.19 µM each of D5S818 primers 1 [SEQ ID NO: 15] and 2 [SEQ ID NO: 16], 0.45 µM each of D7S820 primers 1 [SEQ ID NO: 17] and 2 [SEQ ID NO: 18], and 0.23 µM each of FGA primers 1 [SEQ ID NO: 19] and 2 [SEQ ID NO: 20], 0.09 µM each of D13S317 primers 1 [SEQ ID NO: 21] and 2 [SEQ ID NO: 22], 0.72 µM each of TH01 primers 1 [SEQ ID NO: 23] and 2 [SEQ ID NO: 24], and 0.09 µM each of TPOX primers 1 [SEQ ID NO: 25] and 2 [SEQ ID NO: 26]. The results are shown in FIG. 7. All alleles of the 13 CODIS loci and amelogenin are readily identifiable as peaks of the expected amplicon fragment length corresponding to those found in their multiple subsets as shown in FIGS. 1, 2, 4, and 6.

Example 8
Amplification and Electrophoresis of Multiplex Subset A2 Loci vWA, D21S11, and D18S51

Figure 8:
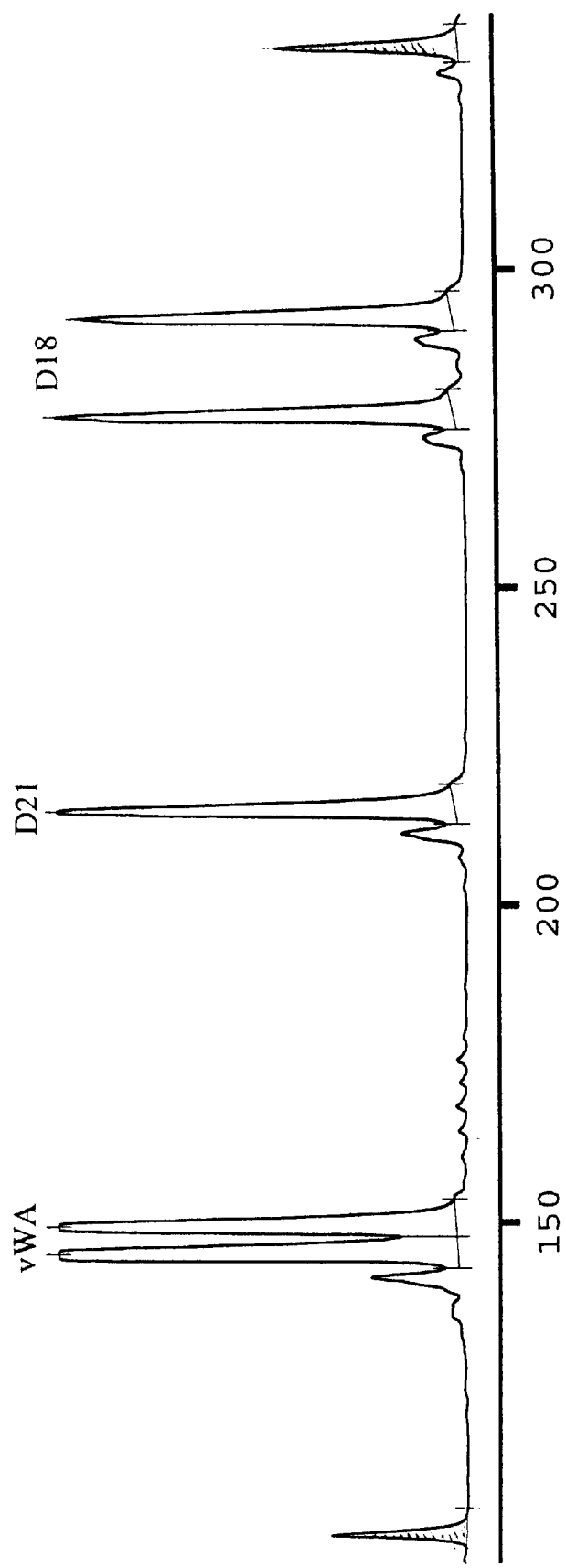
FIG. 8 is a printed image from the ALFexpress automated sequencer (Amersham Pharmacia Biotech) showing the fluorescent detection upon electrophoresis of the PCR product after amplification of the loci from multiplex subset A2: vWA, D21S11' and D18S51. Peak areas correspond to fluorescence intensity and are depicted graphically as a function of fragment length (nt). Fluorescent peaks measured at 101 and 335 nt represent DNA size standards.

This example demonstrates that the fragment length of a PCR amplicon can be changed by adjusting the 5' end of its primer pair. In subset A2 the only difference from subset A1 is the reverse primer of D21S11 which is 6 nt longer at its 5' end (Table 2). In this example, PCR, electrophoretic conditions and data analysis were carried out as described in Methods. The last 30 cycles of PCR were performed at a constant annealing temperature of 57° C. The loci in this example were amplified in a single PCR vessel in total 10 µl reaction volume and their PCR amplicons were analyzed in a single electrophoretic gel lane on ALFexpress. The final primer concentrations in this PCR for each locus were: 0.6 µM each of vWA primers 1 [SEQ ID NO: 1] and 2 [SEQ ID NO: 2], 0.12 µM each of D21S11 primers 1 [SEQ ID NO: 3] and 2 [SEQ ID NO: 29], and 0.3 µM each of D18S51 primers 1 [SEQ ID NO: 5] and 2 [SEQ ID NO: 6]. Reference is made to FIG. 8 which displays the amplified DNA fragments from each locus according to their size (nt) dependent migration in a single gel lane. Individual fragments are identified by the length of the expected amplicons from their locus.

Figure 9:
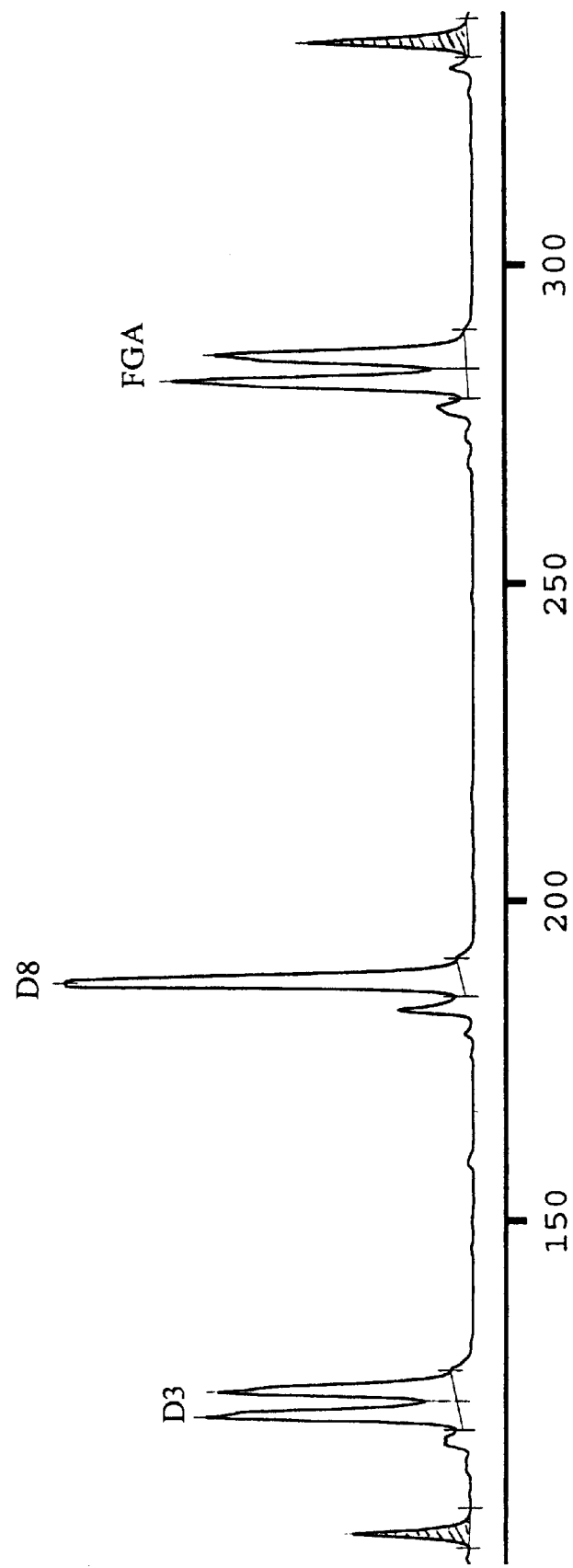
FIG. 9 is a printed image from the ALFexpress automated sequencer (Amersham Pharmacia Biotech) showing the fluorescent detection upon electrophoresis of the PCR product after amplification of the loci from multiplex subset B2: D3S1358', D8S1179 and FGA'. Peak areas correspond to fluorescence intensity and are depicted graphically as a function of fragment length (nt). Fluorescent peaks measured at 101 and 335 nt represent DNA size standards.

Example 9
Amplification and Electrophoresis of Multiplex Subset B2 Loci D3S1358, D8S1179, and FGA This example demonstrates that the loci in a subset may be exchangeable among subsets and that primers amplifying particular loci can be redesigned. In subset B1 loci D16S539 and CSF1PO were replaced by locus FGA to form subset B2. Primers for loci FGA and D3S1358 were redesigned (Table 2) thereby changing the fragment lengths of their PCR amplicons, (Table 1). The ensuing triplex subset, D3S1358, D8S1179 and FGA, can be co-amplified from genomic DNA by its PCR primer pairs labeled with a common fluorophore (Cy5) and co-electrophoresed in a single gel lane without overlap, as judged by their relative position and expected amplicon fragment length ranges (Table 1). In this example, PCR, electrophoretic conditions and data analysis were carried out as described in Methods. The last 30 cycles of PCR were performed at a constant annealing temperature of 57° C. The loci in this example were amplified in a single PCR vessel in total 10 µl reaction volume and their PCR amplicons were analyzed in a single electrophoretic gel lane on ALFexpress. The final primer concentrations in this PCR were: 0.45 µM each of D3S1358 primers 1 [SEQ ID NO: 30] and 2 [SEQ ID NO: 31], 0.45 µM each of D8S1179 primers 1 [SEQ ID NO: 9] and 2 [SEQ ID NO: 10], and 0.18 µM each of FGA primers 1 [SEQ ID NO: 32] and 2 [SEQ ID NO: 33]. Reference is made to FIG. 9 which displays the amplified DNA fragments from each locus according to their size (nt) dependent migration in a single gel lane. Individual fragments are identified by the length of the expected amplicons from their locus.

Example 10
Amplification and Electrophoresis of Multiplex Subset C3 Loci D13S317, D5S818, D7S820, and D16S539

This example demonstrates another restructured subset with different loci and the minor primer change of 3 nt enlongation at the 5' end of the reverse primer of D5S818

Figure 10:
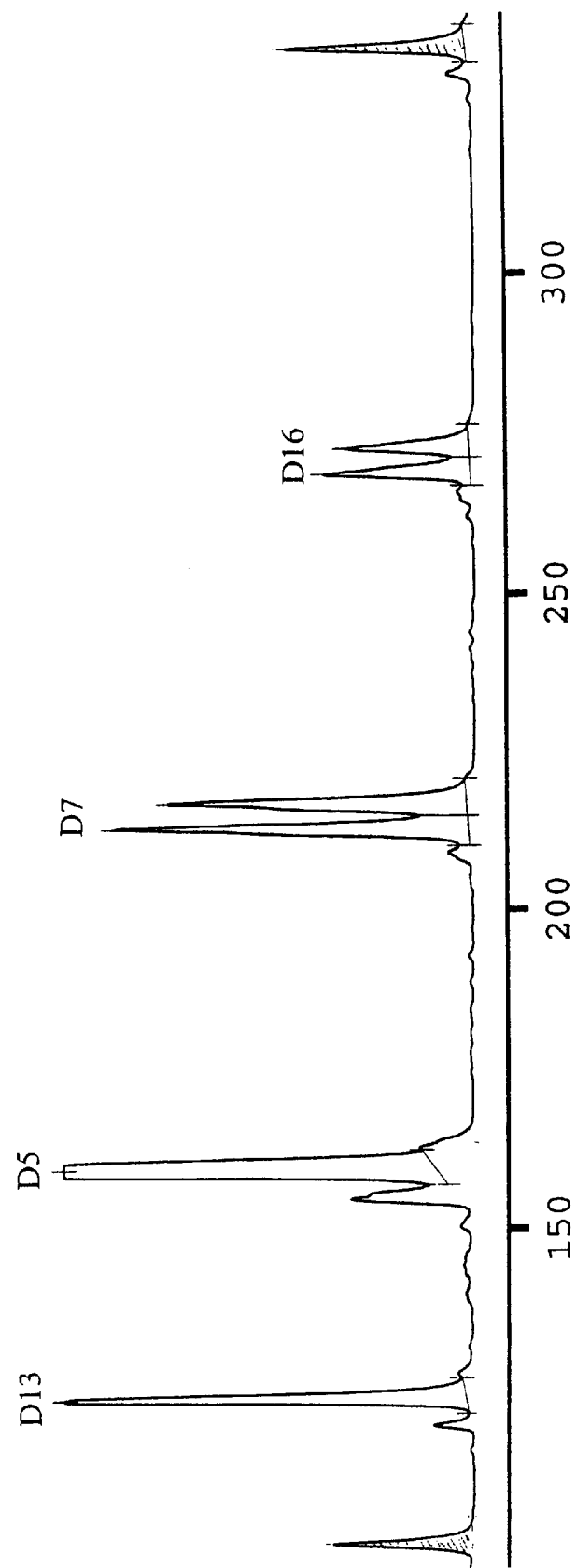
FIG. 10 is a printed image from the ALFexpress automated sequencer (Amersham Pharmacia Biotech) showing the fluorescent detection upon electrophoresis of the PCR product after amplification of the loci from multiplex subset C3: D13S317, D5S818', D7S820, and D16S539. Peak areas correspond to fluorescence intensity and are depicted graphically as a function of fragment length (nt). Fluorescent peaks measured at 101 and 335 nt represent DNA size standards.

(Table 2). Quadriplex subset, D13S317, D5S818, D7S820, and D16S539, can be co-amplified from genomic DNA by their PCR primers labeled with a common fluorophore (Cy5) and co-electrophoresed in a single gel lane without overlap, as judged by their relative position and expected amplicon fragment length ranges (Table 1). In this example, PCR, electrophoretic conditions and data analysis were carried out as described in Methods. The last 30 cycles of PCR were performed at a constant annealing temperature of 57° C. The loci in this example were amplified in a single PCR vessel in total 10 μl reaction volume and their PCR amplicons were analyzed in a single electrophoretic gel lane on ALFexpress. The final primer concentrations in this PCR for each locus were: 0.24 μM each of D13S317 primers 1 [SEQ ID NO: 21] and 2 [SEQ ID NO: 22], 0.24 μM each of D5S818 primers 1 [SEQ ID NO: 15] and 2 [SEQ ID NO: 34], 0.7 μM each of D7S820 primers 1 [SEQ ID NO: 17] and 2 [SEQ ID NO: 18], and 0.15 μM each of D16S539 primers 1 [SEQ ID NO: 11] and 2 [SEQ ID NO: 12]. Reference is made to FIG. 10 which displays the amplified DNA fragments from each locus according to their size (nt) dependent migration in a single gel lane. Individual fragments are identified by the length of the expected amplicons from their locus.

Figure 11:
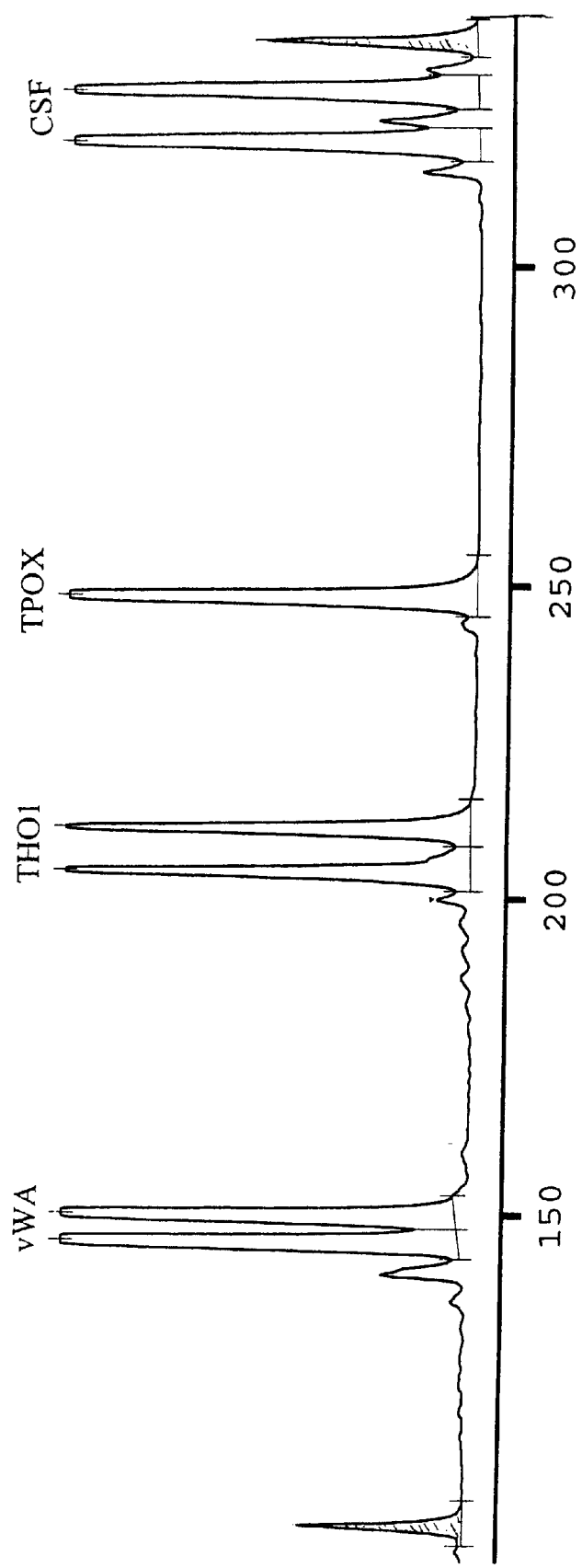
FIG. 11 is a printed image from the ALFexpress automated sequencer (Amersham Pharmacia Biotech) showing the fluorescent detection upon electrophoresis of the PCR product after amplification of the loci from multiplex subset D2: vWA, TH01', TPOX, and CSF1PO. Peak areas correspond to fluorescence intensity and are depicted graphically as a function of fragment length (nt). Fluorescent peaks measured at 101 and 335 nt represent DNA size standards.

Example 11
Amplification and Electrophoresis of Multiplex Subset D2 Loci vWA, TH01, TPOX, and CSF1PO This example demonstrates another restructured quadriplex subset consisting of vWA, TH01, TPOX, and CSF1PO, with the minor primer change of 2 nt elongation at the 5' end of the reverse primer TH01 (Table 2). These 4 loci can be co-amplified from genomic DNA by their PCR primers labeled with a common fluorophore (Cy5) and co-electrophoresed in a single gel lane without overlap, as judged by their relative position and expected amplicon fragment length ranges (Table 1). A duplicated locus vWA, (with subset A2) and three remaining loci, TH01, TPOX, and CSF1PO, of the 13 CODIS loci left by subsets A2, B2, and C2 form this subset D2. The reverse primer of TH01 locus has two extra nucleotides at its 5' end. In this example, PCR, electrophoresis conditions and data analysis were carried out as described in Methods. The last 30 cycles of PCR were performed at constant annealing temperature of 57° C. The loci in this example were amplified in a single PCR vessel in total 10 μl reaction volume and their PCR amplicons were analyzed in a single electrophoretic gel lane on ALF Express. The final primer concentrations in this PCR were: 1.2 μM each of vWA primers 1 [SEQ ID NO: 1] and 2 [SEQ ID NO: 2], 0.4 μM each of TH01 primers 1 [SEQ ID NO: 23] and 2 [SEQ ID NO: 35], 0.12 μM each of TPOX primers 1 [SEQ ID NO: 25] and 2 [SEQ ID NO: 26], and 0.15 μM each of CSF1PO primers 1 [SEQ ID NO: 13] and 2 [SEQ ID NO: 14]. Reference is made to FIG. 11 which displays the amplified DNA fragments from each locus according to their size (nt) dependent migration in a single gel lane. Individual fragments are identified by the length of the expected amplicons from their locus.

Figure 12:
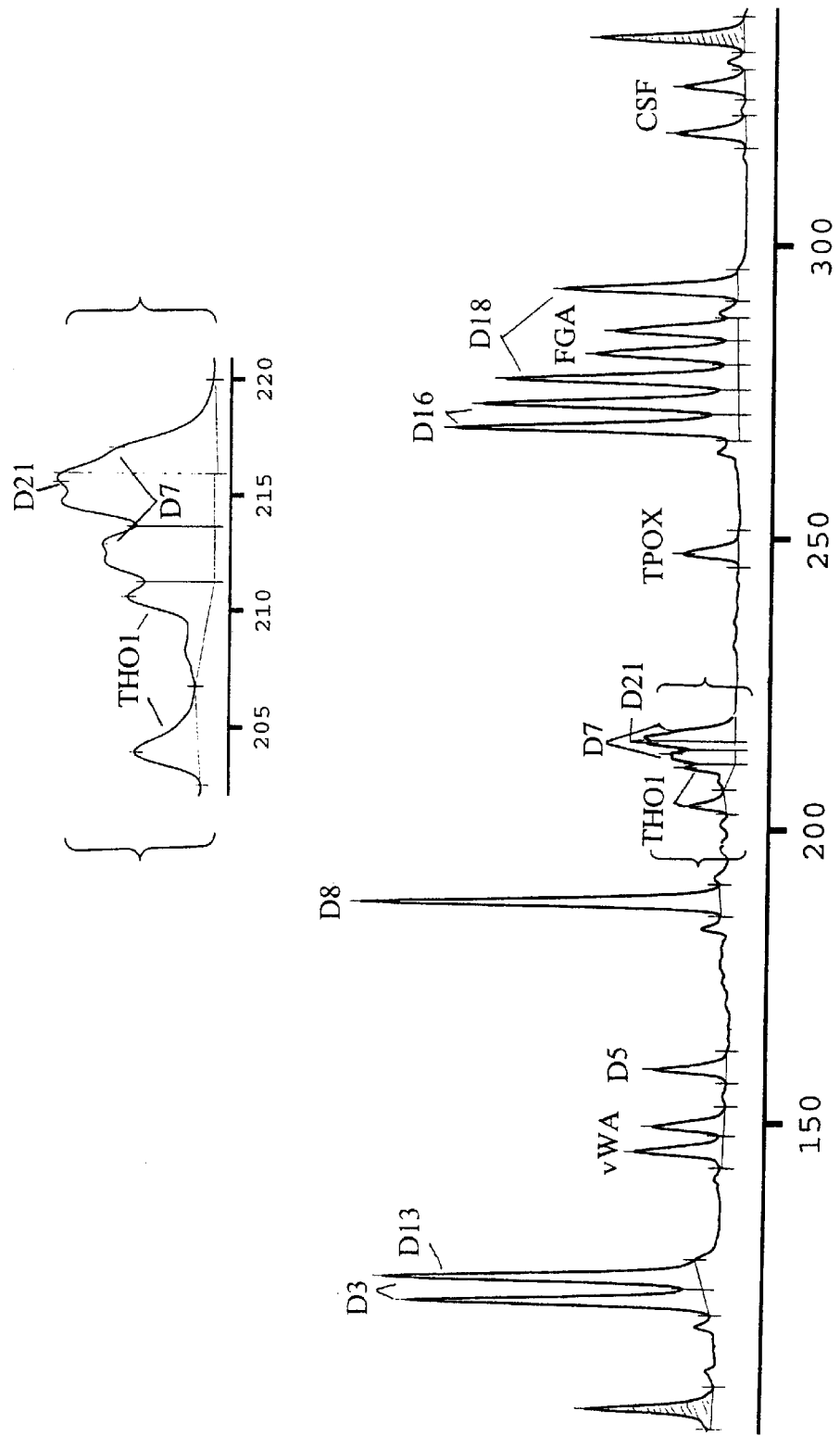
FIG. 12 is a printed image from the ALFexpress automated sequencer (Amersham Pharmacia Biotech) showing the fluorescent detection upon electrophoresis of the PCR product after amplification of the loci from Compound Multiplex III, subsets A2+B2+C3+D2: vWA, D21S11', D18S51, D3S1358', D8S1179, FGA', D13S317, D5S818', D7S820, D16S539, vWA, TH01', TPOX, and CSF1PO. Peak areas correspond to fluorescence intensity and are depicted graphically as a function of fragment length (nt). Fluorescent peaks measured at 101 and 335 nt represent DNA size standards.

Example 12
Amplification and Electrophoresis of Compound Multiplex III: All Thirteen Loci This example demonstrates that all 13 CODIS loci contained in the 4 restructured subsets, A2, B2, C3, and D2, can be co-amplified in one PCR and co-electrophoresed in a single gel lane. In this example, PCR, electrophoretic conditions and data analysis were carried out as described in Methods. The last 30 cycles of PCR were performed at a constant annealing temperature of 57° C. Subsets A2, B2, C3, and D2 loci were amplified in a single PCR vessel in total 20 μl reaction volume and their PCR amplicons were analyzed in a single electrophoretic gel lane on ALFexpress. The final primer concentrations in this PCR for each locus were: 1.2 μM each of vWA primers 1 [SEQ ID NO: 1] and 2 [SEQ ID NO: 2], 0.22 μM each of D21S11 primers 1 [SEQ ID NO: 3] and 2 [SEQ ID NO: 29], and 0.19 μM each of D18S51 primers 1 [SEQ ID NO: 5] and 2 [SEQ ID NO: 6], 0.32 μM each of D3S1358 primers 1 [SEQ ID NO: 30] and 2 [SEQ ID NO: 31], 1.65 μM each of D8S1179 primers 1 [SEQ ID NO: 9] and 2 [SEQ ID NO: 10], 0.28 μM each of FGA primers 1 [SEQ ID NO: 32] and 2 [SEQ ID NO: 33], 0.24 μM each of D13S317 primers 1 [SEQ ID NO: 21] and 2 [SEQ ID NO: 22], 0.24 μM each of D5S818 primers 1 [SEQ ID NO: 15] and 2 [SEQ ID NO: 34], 0.85 μM each of D7S820 primers 1 [SEQ ID NO: 17] and 2 [SEQ ID NO: 18], 0.34 μM each of D16S539 primers 1 [SEQ ID NO: 11] and 2 [SEQ ID NO: 12], 0.28 μM each of TH01 primers 1 [SEQ ID NO: 23] and 2 [SEQ ID NO: 35], and 0.12 μM each of TPOX primers 1 [SEQ ID NO: 25] and 2 [SEQ ID NO: 26], and 0.2 μM each of CSF1PO primers 1 [SEQ ID NO: 13] and 2 [SEQ ID NO: 14]. The results are shown in FIG. 12. All alleles of the 13 CODIS loci are readily identifiable as peaks of the expected amplicon fragment length corresponding to those found in their multiple subsets shown in FIGS. 8–11. The inset shows an expanded view of the TH01, D7 and D21 amplicon peaks.

Figure 13:
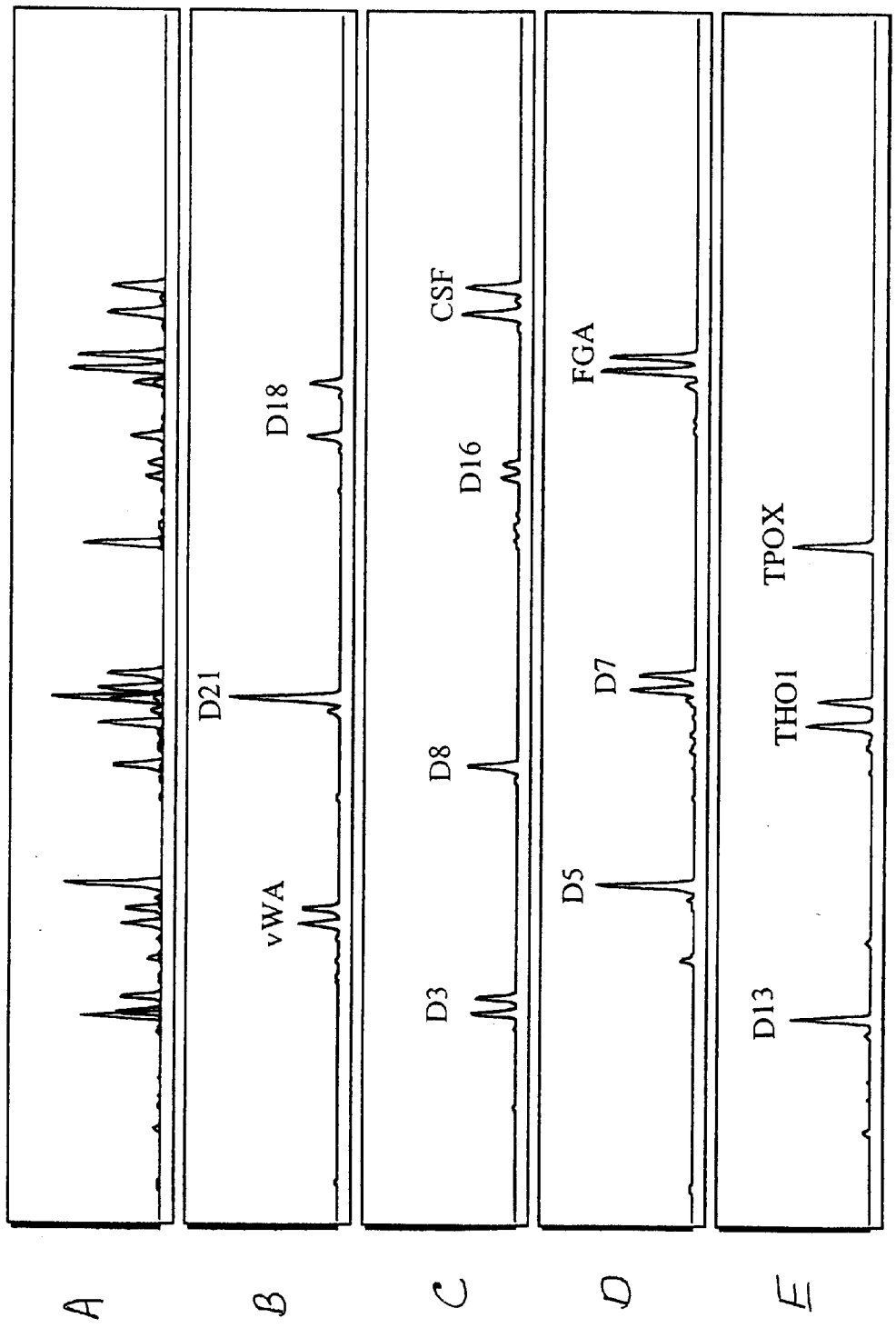
FIGS. 13A, 13B, 13C, 13D and 13E are printed images from the ABI PRISM 310 Genetic Analyzer automated sequencer (PE Applied Biosystems, Foster City, Calif.) showing the fluorescent detection upon electrophoresis of the PCR product after amplification of the loci from individual multiplex subsets A3: vWA, D21S11" and D18S51' (FIG. 13B); B3: D3S1358', D8S1179, D16S539, and CSF1PO (FIG. 13C); C4: D5S818', D7S820, and FGA (FIG. 13D), and D3: D13S317, TH01, and TPOX' (FIG. 13E); and after combined amplification as Compound Multiplex IV (FIG. 13A). Peak areas correspond to fluorescence intensity and are depicted graphically as a function of fragment length (nt).

Example 13
Amplification and Electrophoresis of Compound Multiplex IV: A3 Loci: vWA, D21S11, and D18S51; B3 Loci: D3S1358, D8S1179, D16S539, and CSF1PO; C4 Loci: D5S818, D7S820, and FGA; and D3 Loci: D13S317, TH01, and TPOX This example demonstrates that all 13 CODIS STR loci can be divided into 4 subsets, each labeled with a different fluorophore. Subset A3: vWA, D21S11, and D18S51; subset B3: D3S1358, D8S1179, D16S539, and CSF1PO; subset C4: D5S818, D7S820, and FGA; and subset D3: D13S317, TH01, and TPOX, can be co-amplified from genomic DNA by their PCR primers labeled with different fluorophores, TAMRA to A3, ROX to B3, JOE to C4, and FAM to D3, and co-electrophoresed in a single channel without overlap, as judged by their relative position and expected amplicon fragment length ranges (Table 1). The 4 subsets in this compound multiplex are similar to those in example 5 with a few primer changes, indicated by prime marks (Table 2). In this example, PCR was carried out as described in Methods. The last 25 cycles of PCR were performed at a constant annealing temperature of 61° C. Subset A3, B3, C4, and D3 loci were amplified in a single PCR vessel in total 20 μl reaction volume and the PCR amplicons were electrophoresed on an ABI PRISM 310 Genetic Analyzer. The data was analyzed by the GeneScan Analysis Software, using filter A. The final primer concentrations in this PCR for each locus were: 0.15 μM each of vWA primers 1 [SEQ ID NO: 1] and 2 [SEQ ID NO: 2], 0.11 μM each of D21S11 primers 1 [SEQ ID NO: 36] and 2 [SEQ ID NO: 4], and 0.08 μM each of D18S51 primers 1 [SEQ ID NO: 5] and 2 [SEQ ID NO: 37], 0.12 μM each of D3S1358 primers 1 [SEQ ID NO: 7] and 2 [SEQ ID NO: 31], 0.15 μM each of D8S1179 primers 1 [SEQ ID NO: 9] and 2 [SEQ ID NO: 10], 0.1875 μM each of D16S539 primers 1 [SEQ ID NO: 11] and 2 [SEQ ID NO: 12], and 0.075 μM each of CSF1PO primers 1 [SEQ ID NO: 13] and 2 [SEQ ID NO: 14], 0.11 μM each of D5S818 primers 1 [SEQ ID NO: 15] and 2 [SEQ ID NO: 34], 0.225 μM each of D7S820 primers 1 [SEQ ID NO: 17] and 2 [SEQ ID NO: 18], and 0.1875 μM each of FGA primers 1 [SEQ ID NO: 19] and 2 [SEQ ID NO: 20], 0.045 μM each of D13S317 primers 1 [SEQ ID NO: 21] and 2 [SEQ ID NO: 22], 0.225 μM each of TH01 primers 1 [SEQ ID NO: 23] and 2 [SEQ ID NO: 24], and 0.06 μM each of TPOX primers 1 [SEQ ID NO: 25] and 2 [SEQ ID NO: 38]. The results are shown in FIGS. 13A–13E. FIG. 13A displays combined alleles from 13 CODIS loci labeled with 4 different fluorophores; FIG. 13B displays subset A3 labeled with TAMRA; FIG. 13C displays subset B3 labeled with ROX; FIG. 13D displays subset C4: labeled with JOE; and FIG. 13E displays subset D3 labeled with FAM. All alleles of the. 13 CODIS loci are readily identifiable as peaks of the expected amplicon fragments lengths of their locus.

Alternative configurations of Compound Multiplex IV could be devised to accommodate certain rare alleles of its loci if desired. For example, rare FGA alleles with 42.2 to 50.2 repeats have been reported (Griffiths et al., 1998). In order to maintain an overall multiplex PCR amplicon length of ≦350 bp, subsets C4 and D3 could be rearranged. Locus D7S820 could be removed from subset C4 and added to subset D3 to replace locus TH01. A new reverse primer for TH01 could be designed so that its PCR amplicon size difference of 54 bp in subset C4 (long LSB 236 bp, short LSB 192 bp) would fit in subset D3 beyond the long LSB of TPOX but still be shorter that 350 bp. Then the remaining size range in subset C4 beyond locus D5S818 (LSB long of 182 bp) could be assigned to FGA, allowing all reported FGA alleles to be amplified with amplicon lengths greater that 182 and less than 350 bp.

Figure 14:
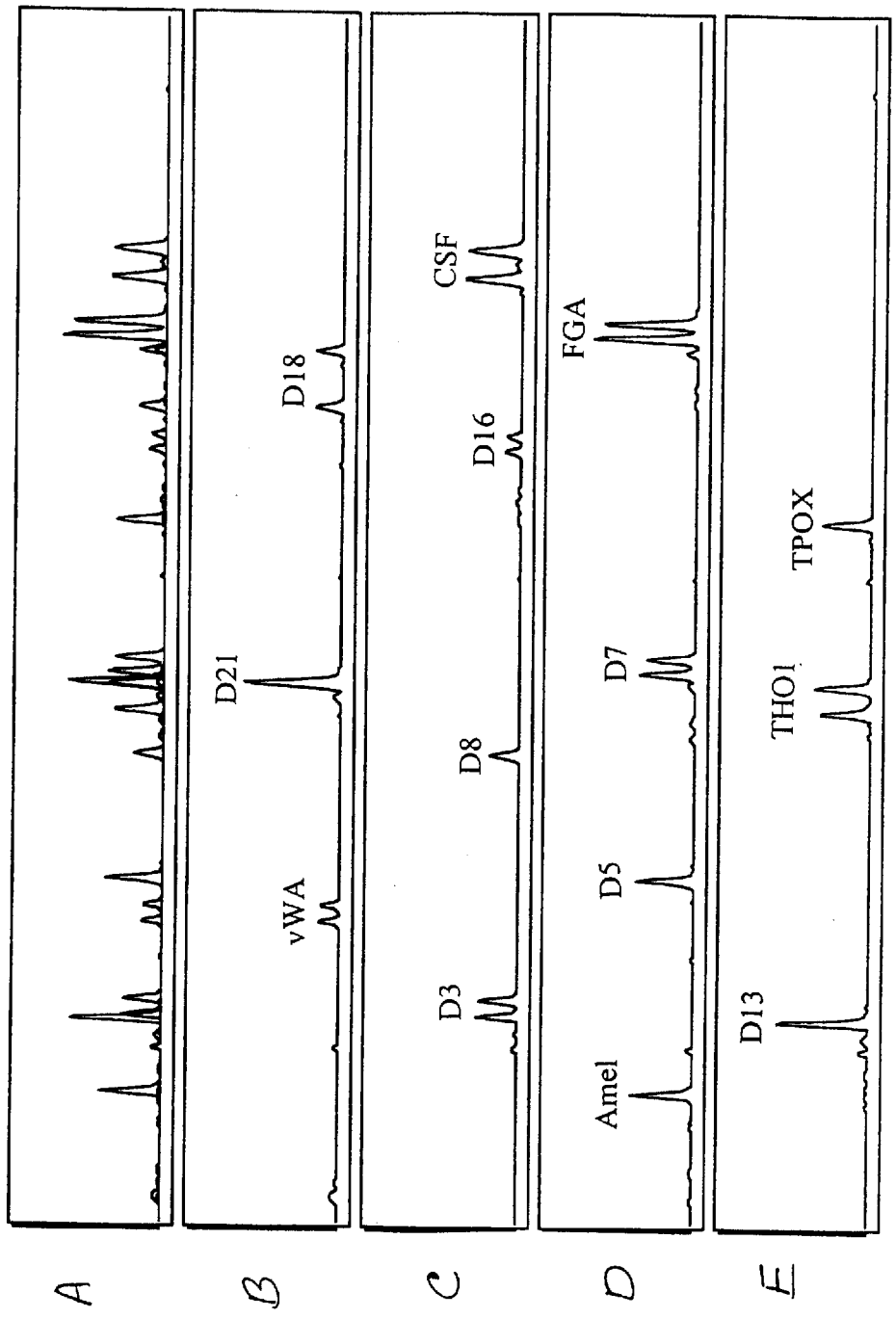
FIGS. 14A, 14B, 14C, 14D and 14E are printed images from the ABI PRISM 310 Genetic Analyzer (PE Applied Biosystems, Foster City, Calif.) showing the fluorescent detection upon electrophoresis of the PCR product after amplification of the loci from individual multiplex subsets A3: vWA, D21S11", and D18S51' (FIG. 14B); B3: D3S1358', D8S1179, D16S539, and CSF1PO (FIG. 14C); C5: amelogenin, D5S818', D7S820, and FGA (FIG. 14D); and D3: D13S317, TH01, and TPOX' (FIG. 14E); and after combined amplification as Compound Multiplex V (FIG. 14A). Peak areas correspond to fluorescence intensity and are depicted graphically as a function of fragment length (nt).

Example 14
Amplification and Electrophoresis of Compound Multiplex V: A3 Loci: vWA, D21S11, and D18S51; B3 Loci: D3S1358, D8S1179, D16S539, and CSF1PO; C5 Loci: Amelogenin, D5S818, D7S820, and FGA; and D3 Loci: D13S317, TH01, and TPOX Example 14 is same as Example 13 except an additional amelogenin locus was added into the compound multiplex. Amelogenin was labeled with JOE and added into subset C4 to become a new multiplex subset C5. The final concentration of this primer pair is 0.08 μM each of amelogenin primers 1 [SEQ ID NO: 27] and 2 [SEQ ID NO: 28]. All other conditions were the same as those used in Example 13. The results are shown in FIGS. 14A–14E. FIG. 14D displays an allele amplified from the amelogenin locus along with alleles amplified from the other 3 loci of subset C5. All alleles of the 13 CODIS loci and amelogenin are readily identifiable as peaks of the expected amplicon fragment lengths of their locus.

Example 15
Amplification and Electrophoresis of Multiplex Subset A4 Loci vWA, D21S11, and D18S51

Figure 15:
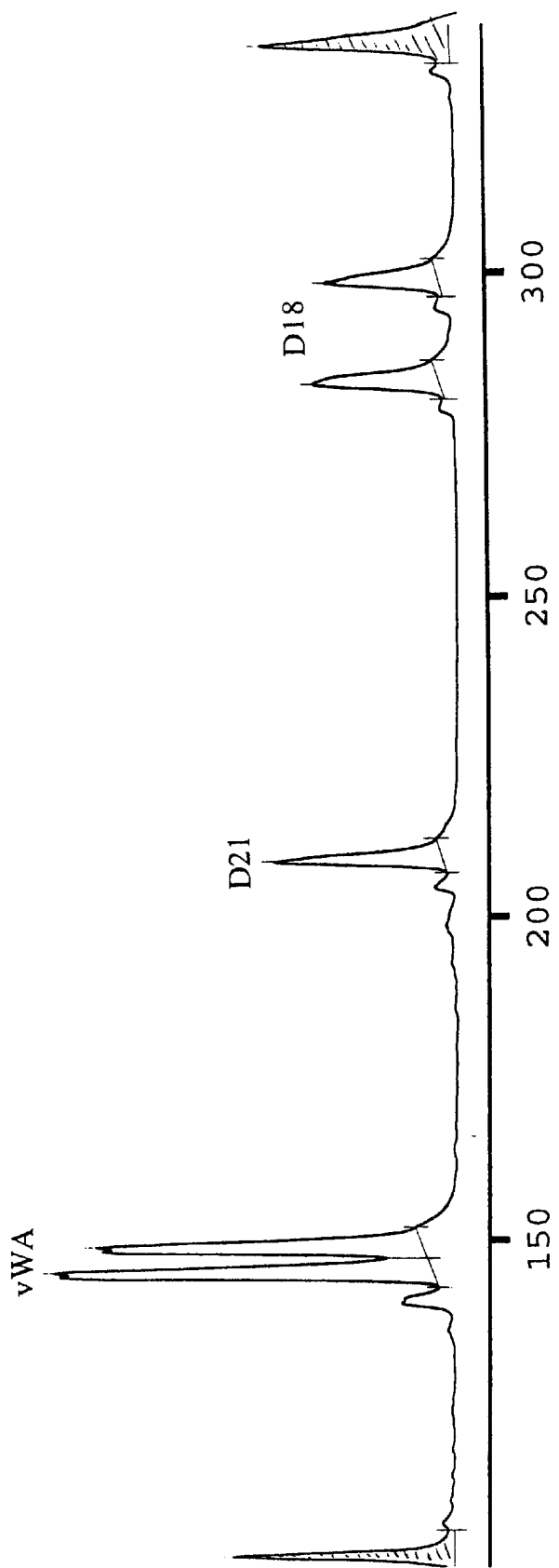
FIG. 15 is a printed image from the ALFexpress automated sequencer (Amersham Pharmacia Biotech) showing the fluorescent detection upon electrophoresis of the PCR product after amplification of the loci from multiplex subset A4: vWA, D21S11, and D18S51". Peak areas correspond to fluorescence intensity and are depicted graphically as a function of fragment length (nt). Fluorescent peaks measured at 101 and 335 nt represent DNA size standards.

This example demonstrates a mutagenetic primer design which may improve the balance of primer melting temperatures and reduce primer dimer formation, as well as increase space between loci within a subset. The reverse primer of locus D18S51 has 3 mutagenetic nuleotides at its 5' end (Table 2). Triplex subset, vWA, D21S11, and D18S51, can be co-amplified from genomic DNA by its PCR primers labeled with a common fluorophore (Cy5) and co-electrophoresed in a single gel lane without overlap, as judged by their relative position and expected amplicon fragment length ranges (Table 1). In this example, PCR, electrophoresis conditions and data analysis were carried out as described in Methods. The last 25 cycles of PCR were performed at a constant annealing temperature of 61° C. The loci in this example were amplified in a single PCR vessel in total 10 μl reaction volume and their PCR amplicons were analyzed in a single electrophoretic gel lane on ALF Express. The final primer concentrations in this PCR for each locus were: 1.5 μM each of vWA primers 1 [SEQ ID NO: 1] and 2 [SEQ ID NO: 2], 0.3 μM each of D21S11 primers 1 [SEQ ID NO: 3] and 2 [SEQ ID NO: 4], and 0.9 μM each of D18S51 primers 1 [SEQ ID NO: 5] and 2 [SEQ ID NO: 39]. Reference is made to FIG. 15 which displays the amplified DNA fragments from each locus according to their size (nt) dependent migration in a single gel lane. Individual fragments are identified by the length of the expected amplicons from their locus.

Figure 16:
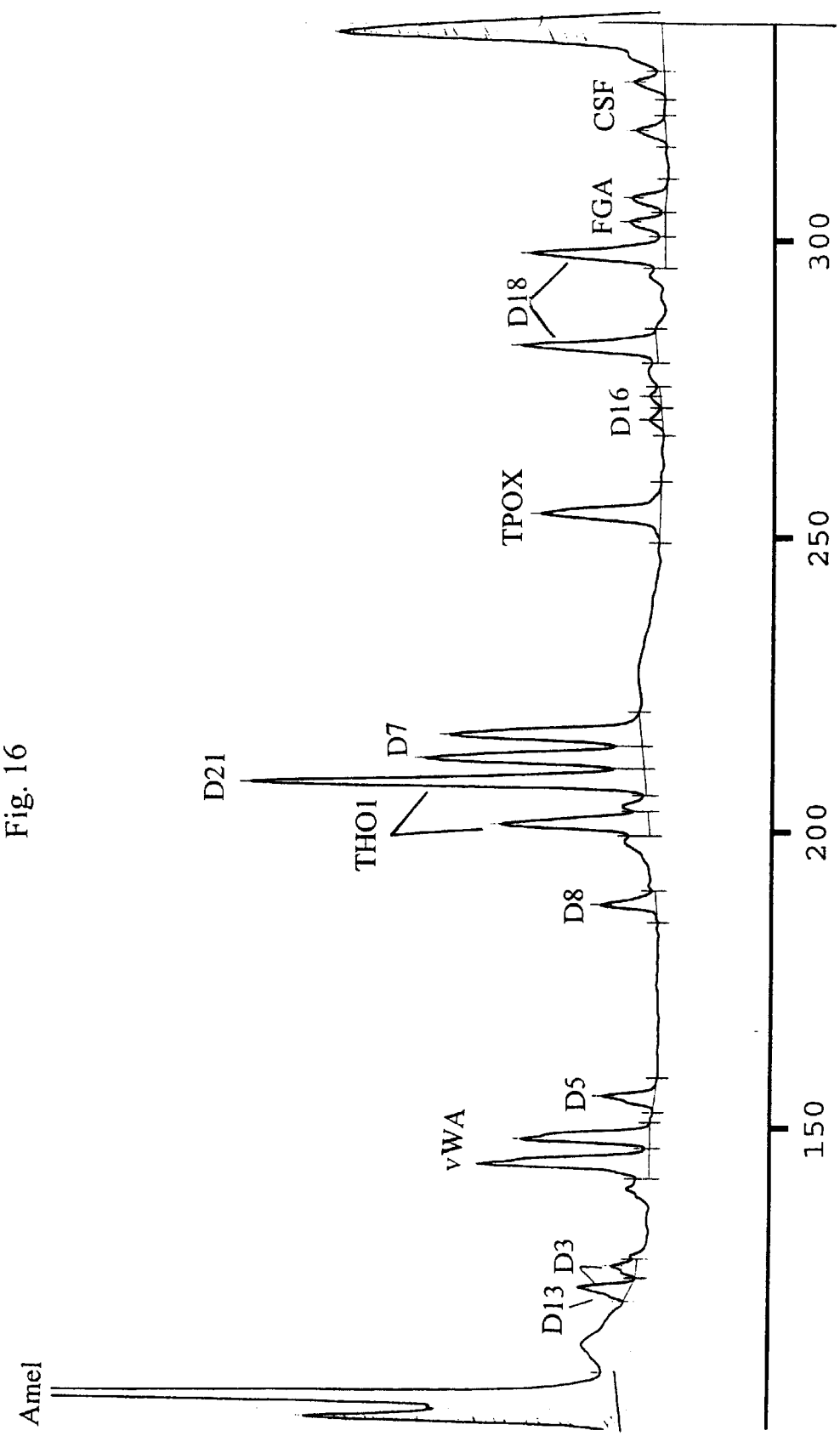
FIG. 16 is a printed image from the ALFexpress automated sequencer (Amersham Pharmacia Biotech) showing the fluorescent detection upon electrophoresis of the PCR product after amplification of the loci from Compound Multiplex VI, subsets A4+B1+C2+D3: vWA, D21S11, D18S51", D3S1358, D8S1179, D16S539, CSF1PO, amelogenin, D5S818, D7S820, FGA, D13S317, TH01, and TPOX'. Peak areas correspond to fluorescence intensity and are depicted graphically as a function of fragment length (nt). Fluorescent peaks measured at 101 and 335 nt represent DNA size standards.

Example 16
Compound Multiplex VI: Amplification Including a Mutagenetic D18S51 Reverse Primer and Electrophoresis of the Amelogenin Locus and the Thireen CODIS Loci This example demonstrates that with a mutagenetic reverse primer of D18S51, amelogenin and all 13 CODIS loci can still be co-amplified from genomic DNA by their PCR primers labeled with a common fluorophore (Cy5) and co-electrophoresed in a single gel lane. Alleles were judged by their relative position and expected amplicon fragment length ranges (Table 1). In this example, PCR, electrophoretic conditions and data analysis were carried out as described in Methods. The last 25 cycles of PCR were performed at a constant annealing temperature of 61° C. Subset A4, B1, C2, and D3 loci were amplified in a single PCR vessel in total 20 μl reaction volume and their PCR amplicons were analyzed in a single electrophoretic gel lane on ALFexpress. The final primer concentrations in this PCR for each locus were: 0.6 μM each of vWA primers 1 [SEQ ID NO: 1] and 2 [SEQ ID NO: 2], 0.23 μM each of D21S11 primers 1 [SEQ ID NO: 3] and 2 [SEQ ID NO: 4], and 0.45 μM each of D18S51 primers 1 [SEQ ID NO: 5] and 2 [SEQ ID NO: 39], 0.23 μM each of D3S1358 primers 1 [SEQ ID NO: 7] and 2 [SEQ ID NO: 8], 0.45 μM each of D8S1179 primers 1 [SEQ ID NO: 9] and 2 [SEQ ID NO: 10], 0.38 μM each of D16S539 primers 1 [SEQ ID NO: 11] and 2 [SEQ ID NO: 12], and 0.15 μM each of CSF1PO primers 1 [SEQ ID NO: 13] and 2 [SEQ ID NO: 14], 0.12 μM each of Amelogenin primers 1 [SEQ ID NO: 27] and 2 [SEQ ID NO: 28], 0.45 μM each of D5S818 primers 1 [SEQ ID NO: 15] and 2 [SEQ ID NO: 16], 0.60 μM each of D7S820 primers 1 [SEQ ID NO: 17] and 2 [SEQ ID NO: 18], and 0.38 μM each of FGA primers 1 [SEQ ID NO: 19] and 2 [SEQ ID NO: 20], 0.12 μM each of D13S317 primers 1 [SEQ ID NO: 21] and 2 [SEQ ID NO: 22], 0.6 μM each of TH01 primers 1 [SEQ ID NO: 23] and 2 [SEQ ID NO: 24], and 0.15 μM each of TPOX primers 1 [SEQ ID NO: 25] and 2 [SEQ ID NO: 38]. The results are shown in FIG. 16. All other alleles of the 13 CODIS loci and amelogenin are readily identifiable as peaks of the expected amplicon fragments length corresponding to those found in their multiple subsets shown in FIGS. 2, 6, 13E, and 15.

Figure 17:
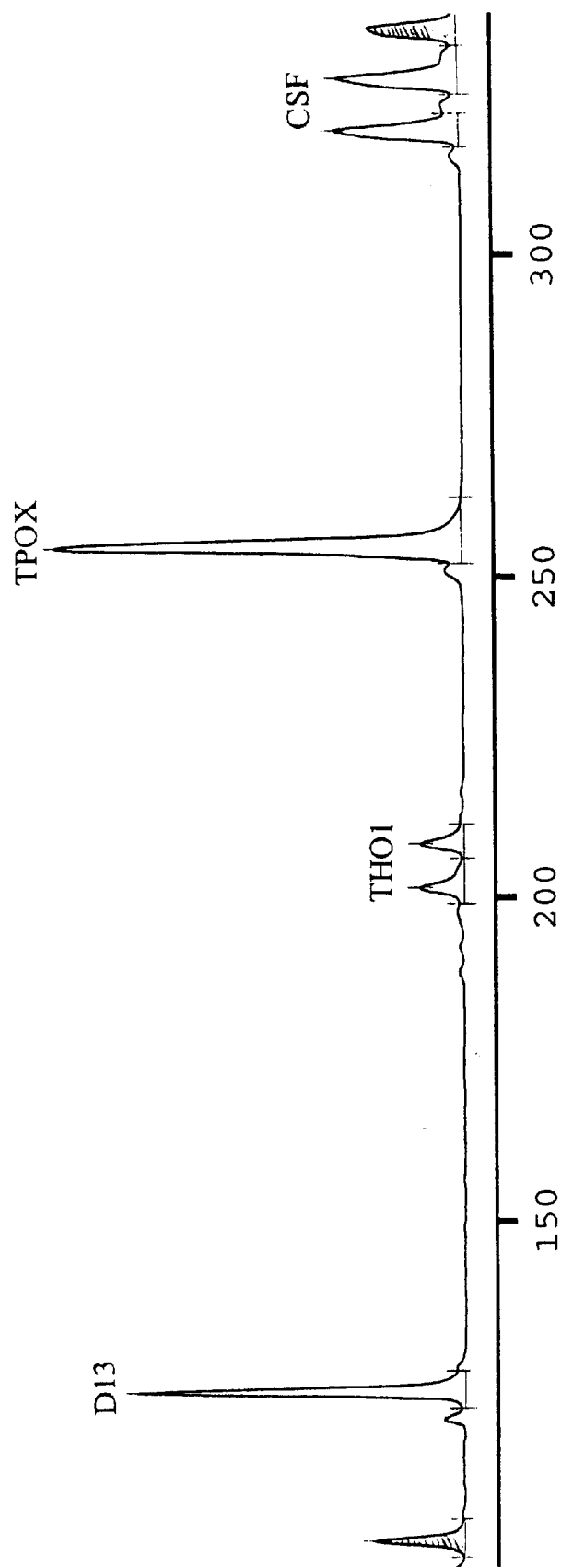
FIG. 17 is a printed image from the ALFexpress automated sequencer (Amersham Pharmacia Biotech) showing the fluorescent detection upon electrophoresis of the PCR product after amplification of the loci from multiplex subset D4: D13S317, TH01, TPOX and CSF1PO. Peak areas correspond to fluorescence intensity and are depicted graphically as a function of fragment length (nt). Fluorescent peaks measured at 101 and 335 nt represent DNA size standards.

Example 17
Amplification and Electrophoresis of Multiplex Subset D4 Loci D13S317, TH01, TPOX, and CSF1PO This example demonstrates that a locus originally amplified in one subset can be successfully amplified in another subset. This is helpful in avoiding sample mix-ups in situations where a DNA sample has to be split and amplified in separate PCR reactions. Locus CSF1PO originally amplified in subset B1 can be co-amplified with triplex D13S317, TH01, and TPOX from genomic DNA by their PCR primers labeled with a common fluorophore (Cy5) to form D4 multiplex subset and co-electrophoresed in a single gel lane without overlap, as judged by their relative position and expected amplicon fragment length ranges (Table 1). In this example, PCR, electrophoretic conditions and data analysis were carried out as described in Methods. The last 25 cycles of PCR were performed at a constant annealing temperature of 61° C. The loci in this example were amplified in a single PCR vessel in total 10 µl reaction volume and their PCR amplicons were analyzed in a single electrophoretic gel lane on ALFexpress. The final primer concentrations in this PCR for each locus were: 0.24 µM each of D13S317 primers 1 [SEQ ID NO: 21] and 2 [SEQ ID NO: 22], 0.6 µM each of TH01 primers 1 [SEQ ID NO: 23] and 2 [SEQ ID NO: 24], 0.21 µM each of TPOX primers 1 [SEQ ID NO: 25] and 2 [SEQ ID NO: 38], and 0.3 µM each of CSF1PO primers 1 [SEQ ID NO: 13] and 2 [SEQ ID NO: 14]. Reference is made to FIG. 17 which displays the amplified DNA fragments from each locus according to their size (nt) dependent migration in a single gel lane. Individual fragments are identified by the length of the expected amplicons from their locus.

Figure 18:
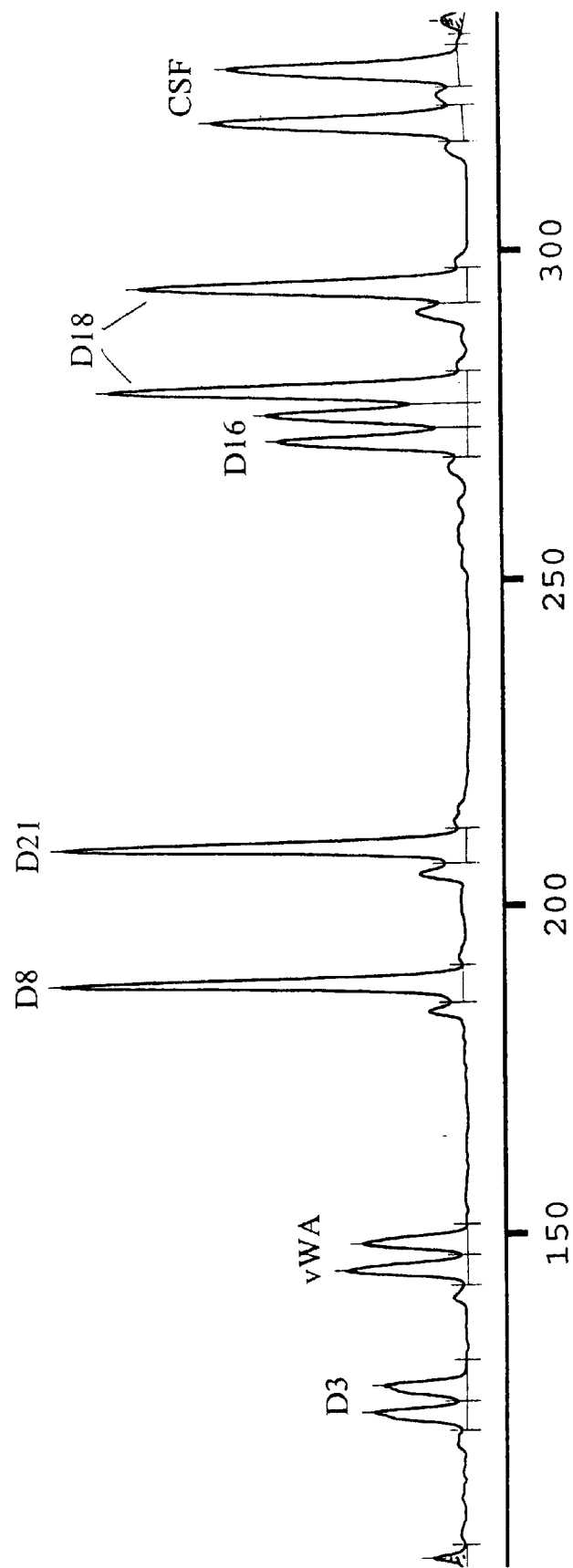
FIG. 18 is a printed image from the ALFexpress automated sequencer (Amersham Pharmacia Biotech) showing the fluorescent detection upon electrophoresis of the PCR product after amplification of the loci from Compound Multiplex VII, subsets A1+B1: vWA, D21S11, D18S51, D3S1358, D8S1179, D16S539, and CSF1PO. Peak areas correspond to fluorescence intensity and are depicted graphically as a function of fragment length (nt). Fluorescent peaks measured at 101 and 335 nt represent DNA size standards.

Example 18
Amplification and Electrophoresis of Compound Multiplex VII: Multiplex Subset A1 Loci vWA, D21S11, and D18S51; and Multiplex Subset B1 Loci D3S1358, D8S1179, D16S539, and CSF1PO This example demonstrates that two subsets can be co-amplified in one PCR for co-electrophoreses in a single lane. This is useful for a two color instrument when the subsets are differentially labeled with fluorophores detectable by that instrument. Subsets A1 and B1 were co-amplified from genomic DNA by their PCR primers labeled with a common fluorophore (Cy5) and co-electrophoresed in a single gel lane. Alleles were judged by their relative position and expected amplicon fragment length ranges (Table 1). In this example, PCR, electrophoretic conditions and data analysis were carried out as described in Methods. Subset A1 and B1 were co-amplified in a single reaction vessel in a total 10 µl reaction volume. The last 25 cycles of PCR were performed at a constant annealing temperature of 61° C. Their PCR amplicons were analyzed in a single electrophoretic gel lane on ALFexpress. The final primer concentrations in this PCR for each locus were: 1.2 µM each of vWA primers 1 [SEQ ID NO: 1] and 2 [SEQ ID NO: 2], 0.3 µM each of D21S11 primers 1 [SEQ ID NO: 3] and 2 [SEQ ID NO: 4], 0.3 µM each of D18S51 primers 1 [SEQ ID NO: 5] and 2 [SEQ ID NO: 6], 0.3 µM each of D3S1358 primers 1 [SEQ ID NO: 7] and 2 [SEQ ID NO: 8], 0.6 µM each of D8S1179 primers 1 [SEQ ID NO: 9] and 2 [SEQ ID NO: 10], 0.6 µM each of D16S539 primers 1 [SEQ ID NO: 11] and 2 [SEQ ID NO: 12], and 0.3 µM each of CSF1PO primers 1 [SEQ ID NO: 13] and 2 [SEQ ID NO: 14]. Reference is made to FIG. 18 which displays the amplified DNA fragments from each locus according to their size (nt) dependent migration in a single gel lane. Individual fragments are identified by the length of the expected amplicons from their locus.

Figure 19:
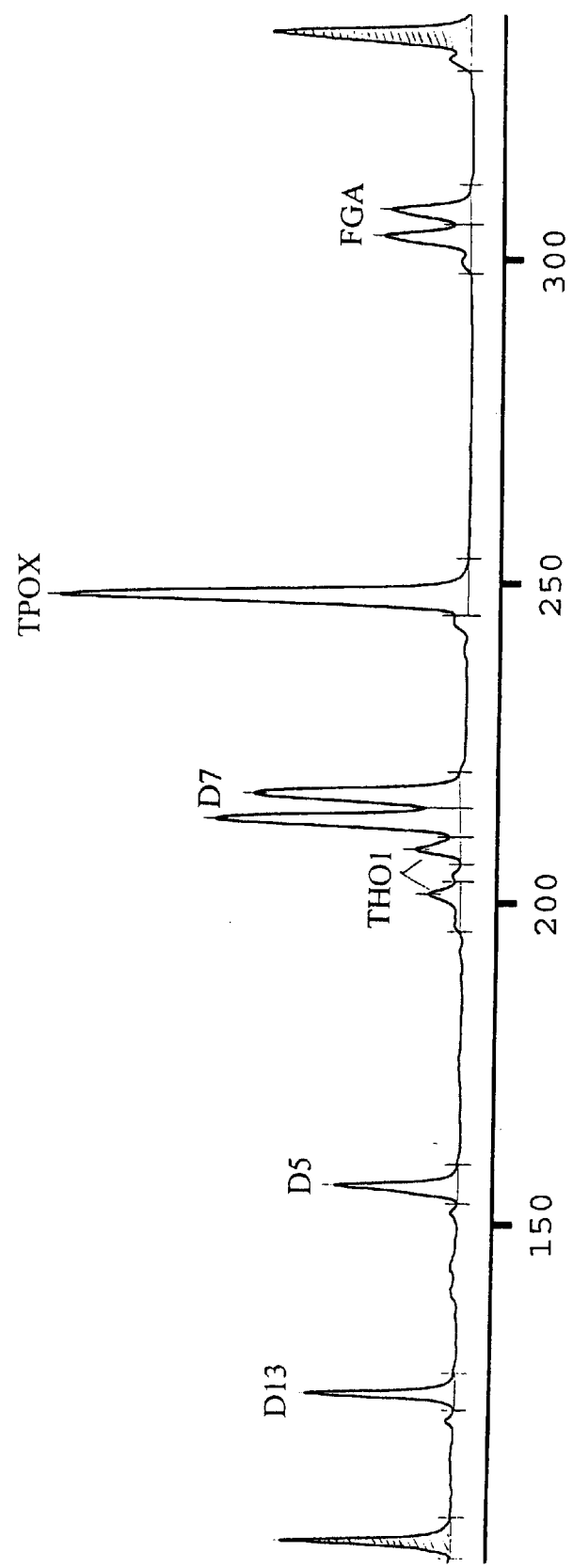
FIG. 19 is a printed image from the ALFexpress automated sequencer (Amersham Pharmacia Biotech) showing the fluorescent detection upon electrophoresis of the PCR product after amplification of the loci from Compound Multiplex VIII, subsets C1+D1: D5S818, D7S820, FGA, D13S317, TH01, and TPOX. Peak areas correspond to fluorescence intensity and are depicted graphically as a function of fragment length (nt). Fluorescent peaks measured at 101 and 335 nt represent DNA size standards.

Example 19
Amplification and Electrophoresis of Compound Multiplex VIII: Multiplex Subset C1 Loci D5S818, D7S820, and FGA; and Multiplex Subset D1 Loci D13S317, TH01, and TPOX This example is also useful for a 2 color instrument. It demonstrates that two subsets, C1 and D1, can be co-amplified from genomic DNA by their PCR primers labeled with a common fluorophore (Cy5) and co-electrophoresed in a single gel lane. Alleles were judged by their relative position and expected amplicon fragment length ranges (Table 1). In this example, PCR, electrophoresis conditions and data analysis were carried out as described in Methods. Subset C1 and D1 were co-amplified in a single reaction vessel in a total 10 µl reaction volume. The last 25 cycles of PCR were performed at a constant annealing temperature of 61° C. Their PCR amplicons were analyzed in a single electrophoretic gel lane on ALFexpress. The final primer concentrations in this PCR for each locus were: 0.3 µM each of D5S818 primers 1 [SEQ ID NO: 15] and 2 [SEQ ID NO: 16], 0.96 µM each of D7S820 primers 1 [SEQ ID NO: 17] and 2 [SEQ ID NO: 18], 0.6 µM each of FGA primers 1 [SEQ ID NO: 19] and 2 [SEQ ID NO: 20], 0.09 µM each of D13S317 primers 1 [SEQ ID NO: 21] and 2 [SEQ ID NO: 22], 0.6 µM each of TH01 primers 1 [SEQ ID NO: 23] and 2 [SEQ ID NO: 24], and 0.05 µM each of TPOX primers 1 [SEQ ID NO: 25] and 2 [SEQ ID NO: 26]. Reference is made to FIG. 19 which displays the amplified DNA fragments from each locus according to their size (nt) dependent migration in a single gel lane. Individual fragments are identified by the length of the expected amplicons from their locus. Together with the A1 and B1 co-amplified loci in Example 17, these loci provide complete CODIS testing for a two color instrument, when each member of a pair is labeled with a fluorophore whose detectable emission can be discriminated from those of the other member of that pair and analyzed in a single electrophoretic channel.

Figure 20:
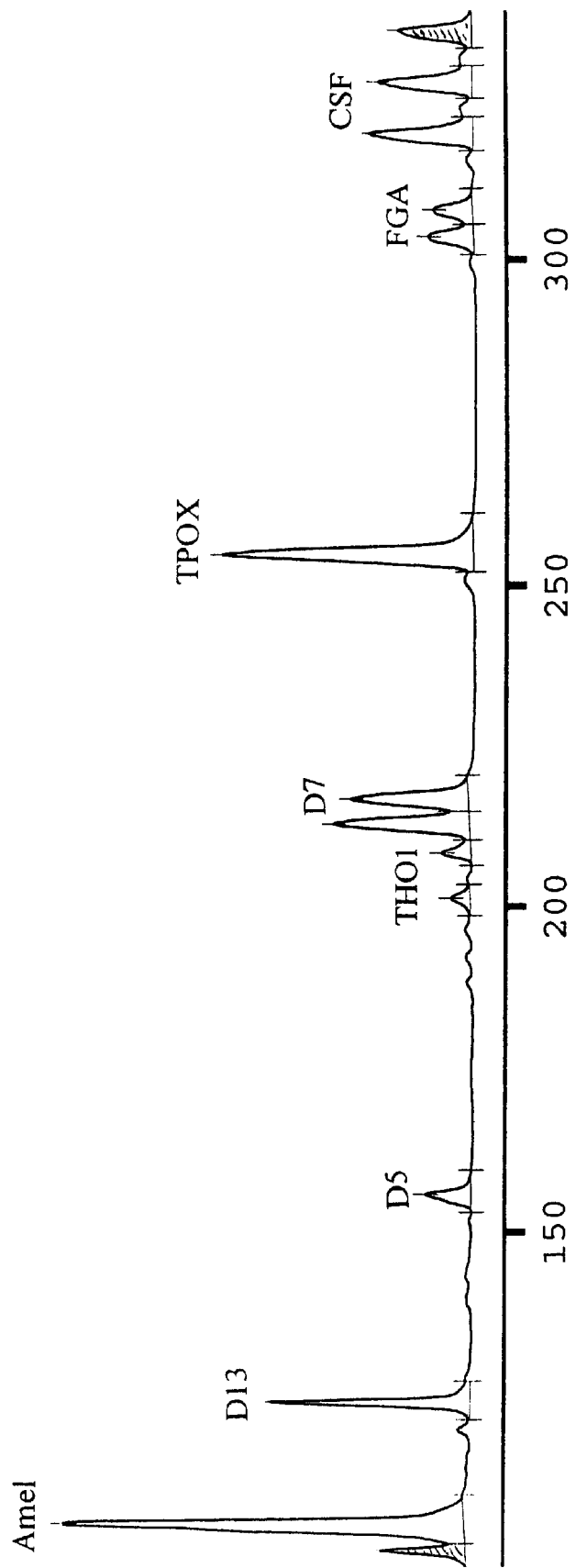
FIG. 20 is a printed image from the ALFexpress automated sequencer (Amersham Pharmacia Biotech) showing the fluorescent detection upon electrophoresis of the PCR product after amplification of the loci from Compound Multiplex IX, subsets C2+D4: amelogenin, D5S818, D7S820, FGA, D13S317, TH01, TPOX and CSF1PO. Peak areas correspond to fluorescence intensity and are depicted graphically as a function of fragment length (nt). Fluorescent peaks measured at 101 and 335 nt represent DNA size standards.

Example 20
Amplification and Electrophoresis of Compound Multiplex IX: Multiplex Subset C2 Loci Amelogenin, D5S818, D7S820, and FGA; and Multiplex Subset D4 Loci D13S317, TH01, TPOX, and CSF1PO This example demonstrates that the loci amelogenin and CSF1PO can be co-amplified within subsets C2 and D4 from genomic DNA by their PCR primers labeled with a common fluorophore (Cy5) and co-electrophoresed in a single gel lane. Alleles were judged by their relative position and expected amplicon fragment length ranges (Table 1). In this example, PCR, electrophoresis conditions and data analysis were carried out as described in Methods. Subset C2 and D4 were co-amplified in a single reaction vessel in total 10 ul reaction volume. The last 25 cycles of PCR were performed at a constant annealing temperature of 61° C. Their PCR amplicons were analyzed in a single electrophoretic gel lane on ALF Express. The final primer concentrations in this PCR for each locus were: 0.15 µM each of Amelogenin primers 1 [SEQ ID NO: 27] and 2 [SEQ ID NO: 28], 0.3 µM each of D5S818 primers 1 [SEQ ID NO: 15] and 2 [SEQ ID NO: 16], 0.96 µM each of D7S820 primers 1 [SEQ ID NO: 17] and 2 [SEQ ID NO: 18], 0.6 µM each of FGA primers 1 [SEQ ID NO: 19] and 2 [SEQ ID NO: 20], 0.24 µM each of D13S317 primers 1 [SEQ ID NO: 21] and 2 [SEQ ID NO: 22], 0.6 µM each of TH01 primers [SEQ ID NO: 23] and 2 [SEQ ID NO: 24], 0.21 µM each of TPOX primers 1 [SEQ ID NO: 25] and 2 [SEQ ID NO: 38], and 0.3 µM each of CSF1PO primers 1 [SEQ ID NO: 13] and 2 [SEQ ID NO: 14]. Reference is made to FIG. 20 which displays the amplified DNA fragments from each locus according to their size (nt) dependent migration in a single gel lane. Individual fragments are identified by the length of the expected amplicons from their locus. Together with the A1 and B1 co-amplified loci in Example 17, these loci when differentially labeled, provide complete CODIS testing plus locus amelogenin and duplicated locus CSF1PO for a two color instrument.

Figure 21:
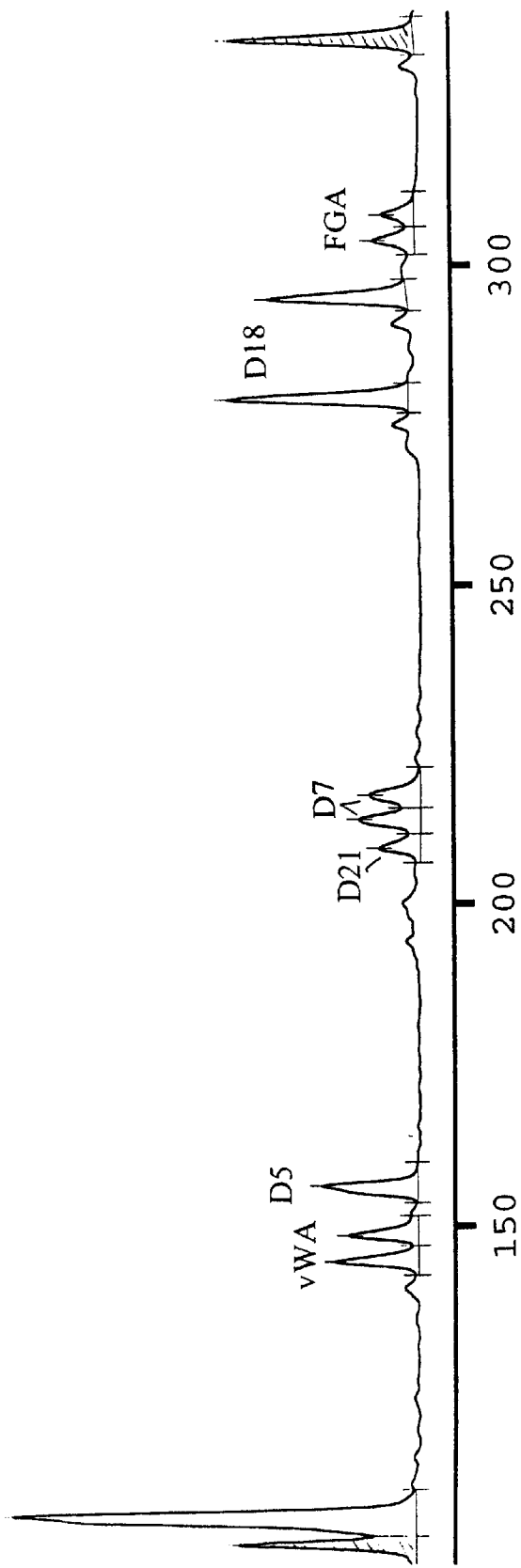
FIG. 21 is a printed image from the ALFexpress automated sequencer (Amersham Pharmacia Biotech) showing the fluorescent detection upon electrophoresis of the PCR product after amplification of the loci from Compound Multiplex X, subsets A1+C2: vWA, D21S11, D18S51, amelogenin, D5S818, D7S820, and FGA. Peak areas correspond to fluorescence intensity and are depicted graphically as a function of fragment length (nt). Fluorescent peaks measured at 101 and 335 nt represent DNA size standards.

Example 21
Amplification and Electrophoresis of Compound Multiplex X: Multiplex Subset A1 Loci vWA, D21S11, and D18S51; and Multiplex Subset C2 Loci Amelogenin, D5S818, D7S820, and FGA This example demonstrates another co-amplification of two subsets. Subset A1 and C2 can be co-amplified from genomic DNA by their PCR primers labeled with a common fluorophore (Cy5) and co-electrophoresed in a single gel lane. Alleles were judged by their relative position and expected amplicon fragment length ranges (Table 1). In this example, PCR, electrophoretic conditions and data analysis were carried out as described in Methods. Subset A1 and C2 were co-amplified in a single reaction vessel in total 10 ul reaction volume. The last 25 cycles of PCR were performed at a constant annealing temperature of 61° C. Their PCR amplicons were analyzed in a single electrophoretic gel lane on ALFexpress. The final primer concentrations in this PCR for each locus were: 1.2 $\mu$M each of vWA primers 1 [SEQ ID NO: 1] and 2 [SEQ ID NO: 2], 0.3 $\mu$M each of D21S11 primers 1 [SEQ ID NO: 3] and 2 [SEQ ID NO: 4], 0.3 $\mu$M each of D18S51 primers 1 [SEQ ID NO: 5] and 2 [SEQ ID NO: 6], 0.23 $\mu$M each of Amelogenin primers 1 [SEQ ID NO: 27] and 2 [SEQ ID NO: 28], 0.3 $\mu$M each of D5S818 primers 1 [SEQ ID NO: 15] and 2 [SEQ ID NO: 16], 0.96 $\mu$M each of D7S820 primers 1 [SEQ ID NO: 17] and 2 [SEQ ID NO: 18], and 0.6 $\mu$M each of FGA primers 1 [SEQ ID NO: 19] and 2 [SEQ ID NO: 20]. Reference is made to FIG. 21 which displays the amplified DNA fragments from each locus according to their size (nt) dependent migration in a single gel lane. Individual fragments are identified by the length of the expected amplicons from their locus.

Figure 22:
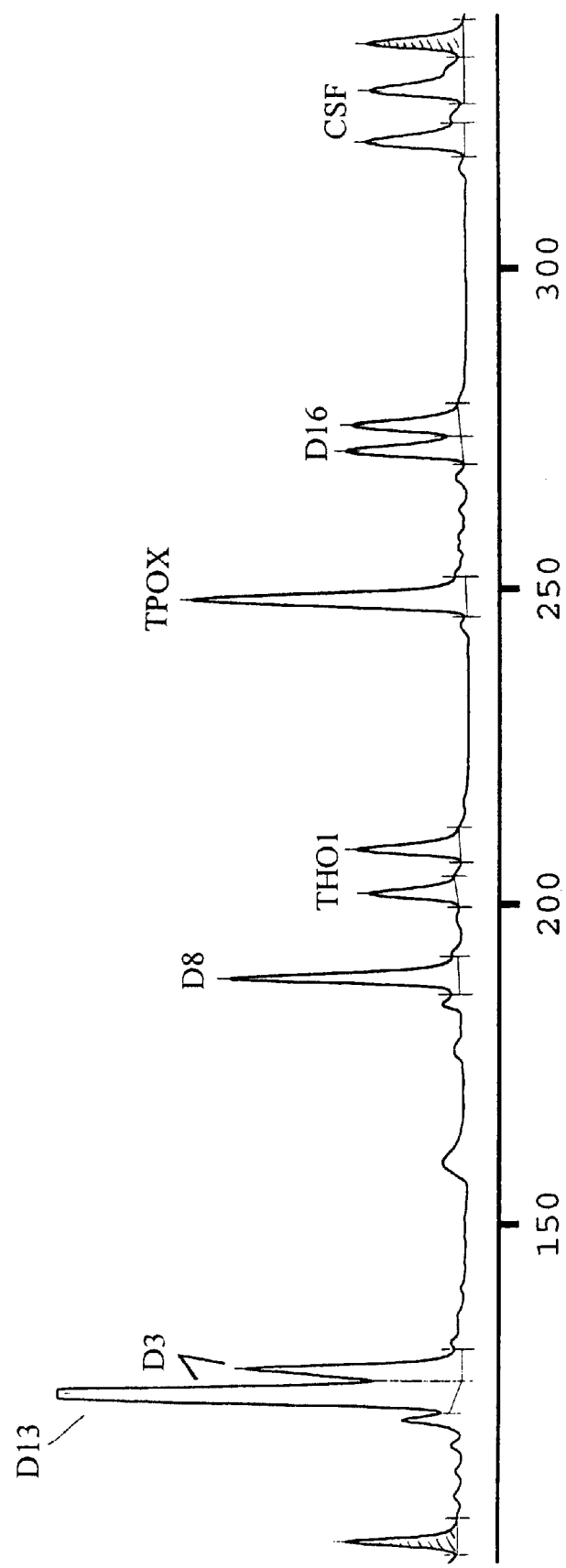
FIG. 22 is a printed image from the ALFexpress: automated sequencer (Amersham Pharmacia Biotech) showing the fluorescent detection upon electrophoresis of the PCR product after amplification of the loci from Compound Multiplex XI, subsets B1+D1: D3S1358, D8S1179, D16S539, CSF1PO, D13S317, TH01, and TPOX. Peak areas correspond to fluorescence intensity and are depicted graphically as a function of fragment length (nt). Fluorescent peaks measured at 101 and 335 nt represent DNA size standards.

Example 22
Amplification and Electrophoresis of Compound Multiplex XI: Multiplex Subset B1 Loci D3S1358, D8S1179, D16S539, and CSF1PO; and Multiplex Subset D1 Loci D13S317, TH01, and TPOX This example demonstrates another co-amplification of two subsets. Subset B1 and D1 can be co-amplified from genomic DNA by their PCR primers labeled with a common fluorophore (Cy5) and co-electrophoresed in a single gel lane. Alleles were judged by their relative position and expected amplicon fragment length ranges (Table 1). In this example, PCR, electrophoresis conditions and data analysis were carried out as described in Methods. Subset B1 and D1 were co-amplified in a single reaction vessel in total 10 $\mu$l reaction volume. The last 25 cycles of PCR were performed at a constant annealing temperature of 61° C. Their PCR amplicons were analyzed in a single electrophoretic gel lane on ALFexpress. The final primer concentrations in this PCR for each locus were: 0.3 $\mu$M each of D3S1358 primers 1 [SEQ ID NO: 7] and 2 [SEQ ID NO: 8], 0.6 $\mu$M each of D8S1179 primers 1 [SEQ ID NO: 9] and 2 [SEQ ID NO: 10], 0.75 $\mu$M each of D16S539 primers 1 [SEQ ID NO: 11] and 2 [SEQ ID NO: 12], and 0.3 $\mu$M each of CSF1PO primers 1 [SEQ ID NO: 13] and 2 [SEQ ID NO: 14], 0.09 $\mu$M each of D13S317 primers 1 [SEQ ID NO: 21] and 2 [SEQ ID NO: 22], 0.6 $\mu$M each of TH01 primers 1 [SEQ ID NO: 23] and 2 [SEQ ID NO: 24], and 0.05 $\mu$M each of TPOX primers 1 [SEQ ID NO: 25] and 2 [SEQ ID NO: 26]. Reference is made to FIG. 22 which displays the amplified DNA fragments from each locus according to their size (nt) dependent migration in a single gel lane. Individual fragments are identified by the length of the expected amplicons from their locus. Together with the A1 and C2 co-amplified loci in Example 21, when differentially labeled these loci provide complete CODIS testing plus amelogenin for a two color instrument.

Figure 23:
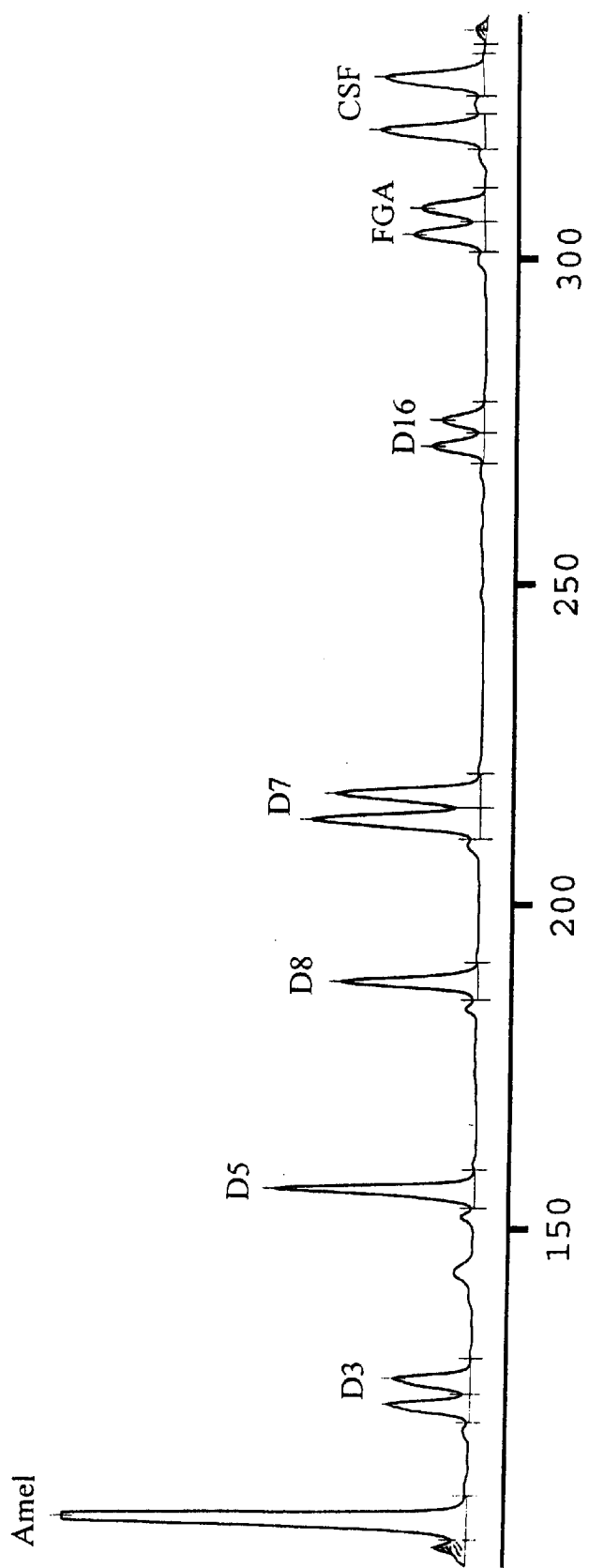
FIG. 23 is a printed image from the ALFexpress: automated sequencer (Amersham Pharmacia Biotech) showing the fluorescent detection upon electrophoresis of the PCR product after amplification of the loci from Compound Multiplex XII, subsets B1+C2: D3S1358, D8S1179, D16S539, CSF1PO, amelogenin, D5S818, D7S820, and FGA. Peak areas correspond to fluorescence intensity and are depicted graphically as a function of fragment length (nt). Fluorescent peaks measured at 101 and 335 nt represent DNA size standards.

Example 23
Amplification and Electrophoresis of Compound Multiplex XII: Multiplex Subset B1 Loci D3S1358, D8S1179, D16S539, land CSF1PO; and Multiplex Subset C2 Loci Amelogenin, D5S818, D7S820, and FGA This example demonstrates another co-amplification of 8 loci in two subsets which can be used in a situation where not all CODIS 13 loci are needed. Subset B1 and C2 can be co-amplified from genomic DNA by their PCR primers labeled with a common fluorophore (Cy5) and co-electrophoresed in a single gel lane. Alleles were judged by their relative position and expected amplicon fragment length ranges (Table 1). In this example, PCR, electrophoretic conditions and data analysis were carried out as described in Methods. Subset B1 and C2 were co-amplified in a single reaction vessel in total 10 $\mu$l reaction volume. The last 25 cycles of PCR were performed at a constant annealing temperature of 61° C. Their PCR amplicons were analyzed in a single electrophoretic gel lane on ALFexpress. The final primer concentrations in this PCR for each locus were: 0.3 $\mu$M each of D3S1358 primers 1 [SEQ ID NO: 7] and 2 [SEQ ID NO: 8], 0.6 $\mu$M each of D8S1179 primers 1 [SEQ ID NO: 9] and 2 [SEQ ID NO: 10], 0.75 $\mu$M each of D16S539 primers 1 [SEQ ID NO: 11] and 2 [SEQ ID NO: 12], and 0.3 $\mu$M each of CSF1PO primers 1 [SEQ ID NO: 13] and 2 [SEQ ID NO: 14], 0.23 $\mu$M each of Amelogenin primers 1 [SEQ ID NO: 27] and 2 [SEQ ID NO: 28], 0.3 $\mu$M each of D5S818 primers 1 [SEQ ID NO: 15] and 2 [SEQ ID NO: 16], 0.96 $\mu$M each of D7S820 primers 1 [SEQ ID NO: 17] and 2 [SEQ ID NO: 18], and 0.6 $\mu$M each of FGA primers 1 [SEQ ID NO: 19] and 2 [SEQ ID NO: 20]. Reference is made to FIG. 23 which displays the amplified DNA fragments from each locus according to their size (nt) dependent migration in a single gel lane. Individual fragments are identified by the length of the expected amplicons from their locus.

Example 24
Electrophoresis of Multiplex Subset A1 Loci vWA, D21S11, and D18S51 and Their Locus Specific Brackets (LSB)

Figure 24:
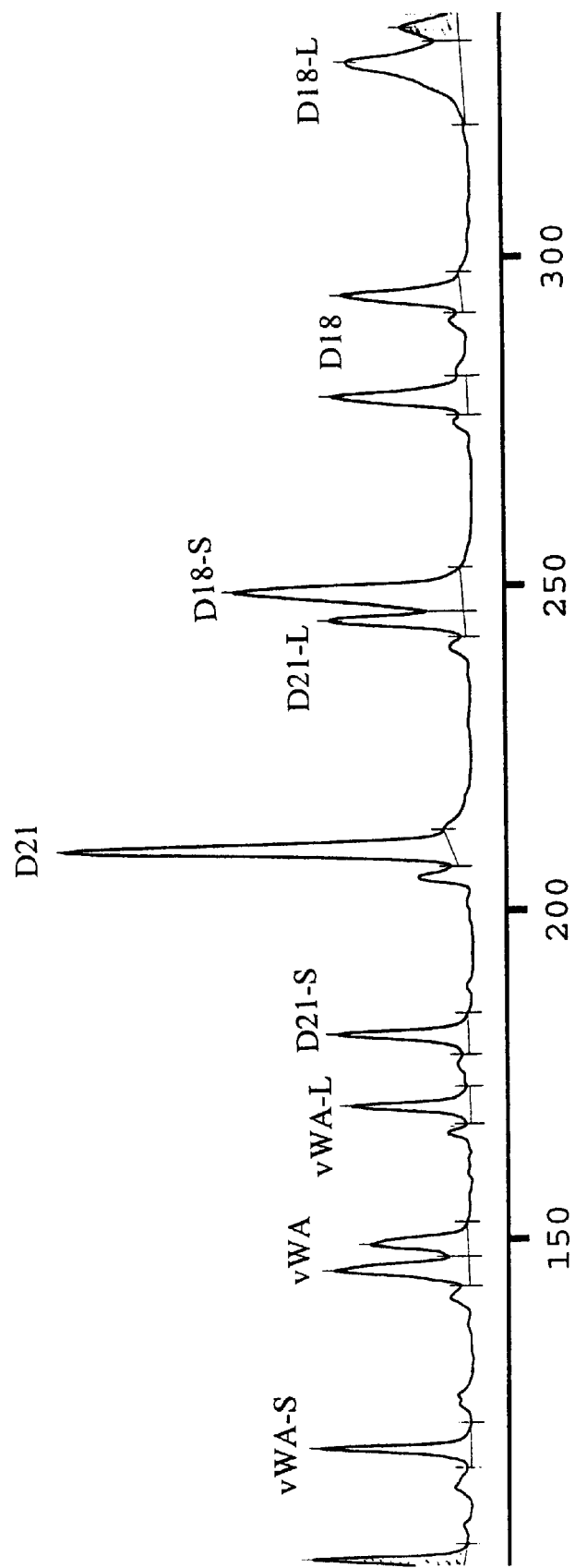
FIG. 24 is a printed image from the ALFexpress. automated sequencer (Amersham Pharmacia Biotech) showing the fluorescent detection upon electrophoresis of the PCR product after amplification of the loci from multiplex subset A1: vWA, D21S11, D18S51, and their Locus Specific Brackets (LSB). vWA-S and vWA-L: short and long LSBs, respectively, for locus vWA; D21-S and D21-L: short and long LSBs, respectively, for locus D21S11; D18-S and D18-L: short and long LSBs, respectively, for locus D18S51. Peak areas correspond to fluorescence intensity and are depicted graphically as a function of fragment length (nt). Fluorescent peaks measured at 101 and 335 nt represent DNA size standards.

Each short and long LSB for A1 loci was amplified from its locus specific LSB template (Dau et al., U.S. Patent) by the same primer pair used in Subset A1 in a single PCR vessel. The number of repeats in each LSB are shown in Table 1. The mixture of each individual LSB PCR amplicon from A1 loci was added into Multiplex Subset A1 PCR amplicons (same as those in FIG. 1) and co-electrophoresed in a single gel lane on ALF Express. PCR and electrophoresis conditions were as described in Methods. Reference is made to FIG. 24 which displays the amplified DNA fragments from each locus and their LSB templates according to their size (nt) dependent migration in a single gel lane. Individual fragments are identified by the length of the expected amplicons from their locus.

Example 25
Electrophoresis of Multiplex Subset B1 Loci D3S1358, D8S1179, D16S539, and CSF1PO and Their Locus Specific Brackets (LSB)

Figure 25:
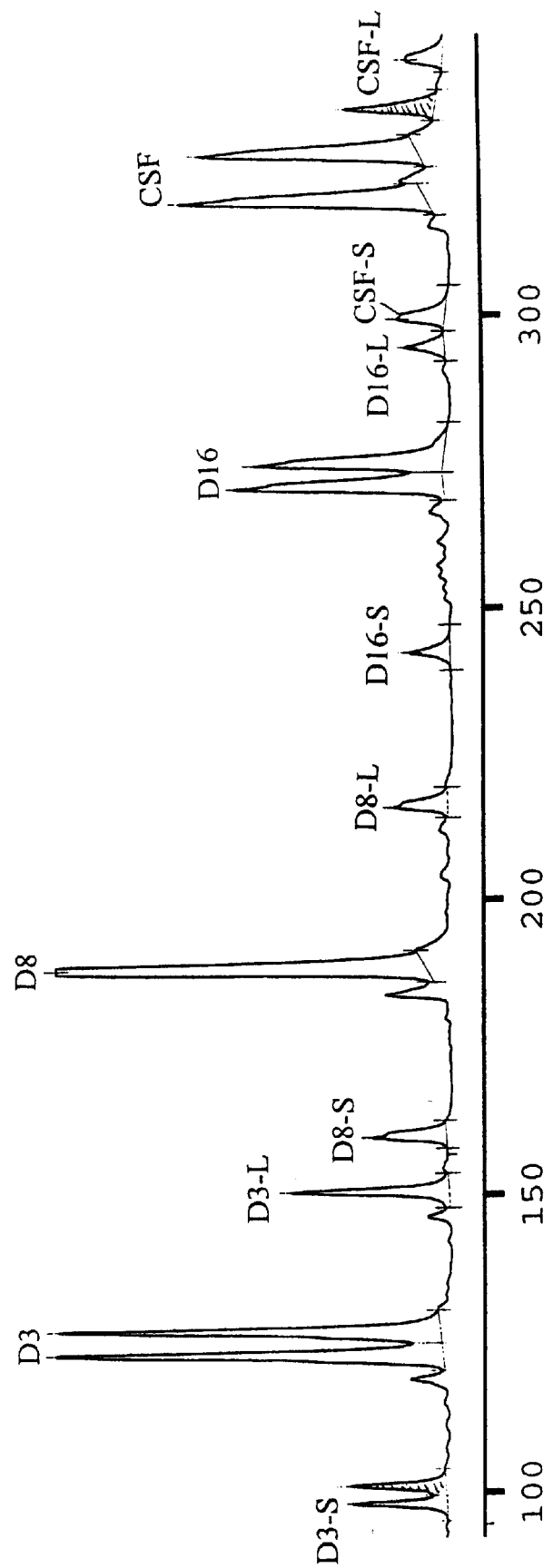
FIG. 25 is a printed image from the ALFexpress automated sequencer (Amersham Pharmacia Biotech) showing the fluorescent detection upon electrophoresis of the PCR product after amplification of the loci from multiplex subset B1: D3S1358, D8S1179, D16S539, and CSF1PO, and their Locus Specific Brackets (LSB). D3-S and D3-L: short and long LSBs, respectively, for locus D3S1358; D8-S and D8-L: short and long LSBs, respectively, for locus D8S1179; D16-S and D16-L: short and long LSBs, respectively, for locus D16S539; and CSF-S and CSF-L: short and long LSBs, respectively, for locus CSF1PO. Peak areas correspond to fluorescence intensity and are depicted graphically as a function of fragment length (nt). Fluorescent peaks measured at 101 and 335 nt represent DNA size standards.

Each short and long LSB for B1 loci was amplified from its locus specific LSB template (Dau et al., U.S. Patent) by the same primer pair used in Subset B1 in a single PCR vessel. The number of repeats in each LSB are shown in Table 1. The mixture of each individual LSB PCR amplicon of B1 loci was added into Multiplex Subset B1 PCR amplicons (same as those in FIG. 2) and co-electrophoresed in a single gel lane on ALF Express. PCR and electrophoresis conditions were as described in Methods. Reference is made to FIG. 25 which displays the amplified DNA fragments from each locus and their LSB templates according to their size (nt) dependent migration in a single gel lane. Individual fragments are identified by the length of the expected amplicons from their locus.

Example 26

Electrophoresis of Multiplex Subset C1 Loci D5S818, D7S820, and FGA and Their Locus Specific Brackets (LSB)

Figure 26:
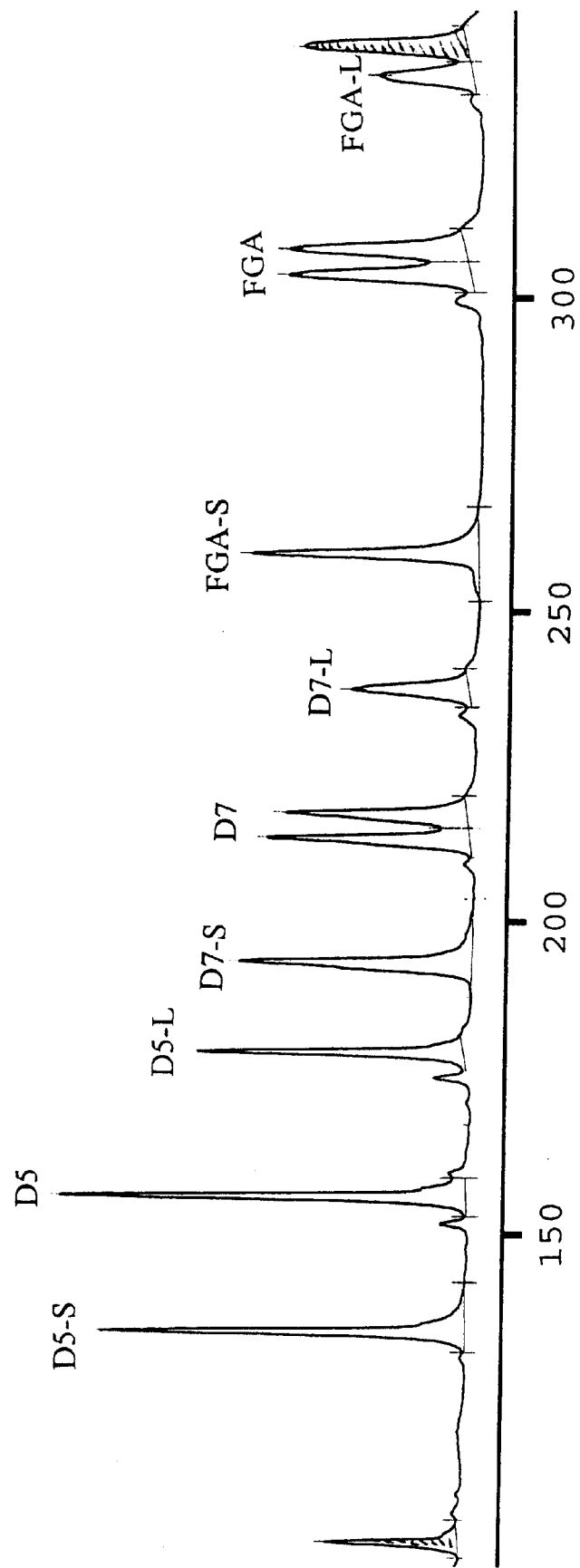
FIG. 26 is a printed image from the ALFexpress automated sequencer (Amersham Pharmacia Biotech) showing the fluorescent detection upon electrophoresis of the PCR product after amplification of the loci from multiplex subset C1: D5S818, D7S820, and FGA, and their Locus Specific Brackets (LSB). D5-S and D5-L: short and long LSBs, respectively, for locus D5S818; D7-S and D7-L: short and long LSBs, respectively, for locus D7S820; FGA-S and FGA-L: short and long LSBs, respectively, for locus FGA. Peak areas correspond to fluorescence intensity and are depicted graphically as a function of fragment length (nt). Fluorescent peaks measured at 101 and 335 nt represent DNA size standards.

Each short and long LSB for C1 loci was amplified from its locus LSB template (Dau et al., U.S. Pat. No. 6,013,444) by the same primer pair used in Subset C1 in a single PCR vessel. The number of repeats in each LSB are shown in Table 1. The mixture of each individual LSB PCR amplicon of C1 loci was added into Multiplex Subset C1 PCR amplicons (same as those in FIG. 3) and co-electrophorsed in a single gel lane on ALF Express. PCR and electrophoresis conditions were as described in Methods. Reference is made to FIG. 26 which displays the amplified DNA fragments from each locus and their LSB templates according to their size (nt) dependent migration in a single gel lane. Individual fragments are identified by the length of the expected amplicons from their locus.

Example 27

Electrophoresis of Multiplex Subset D1 Loci D13S317, TH01, and TPOX and Their Locus Specific Brackets (LSB)

Figure 27:
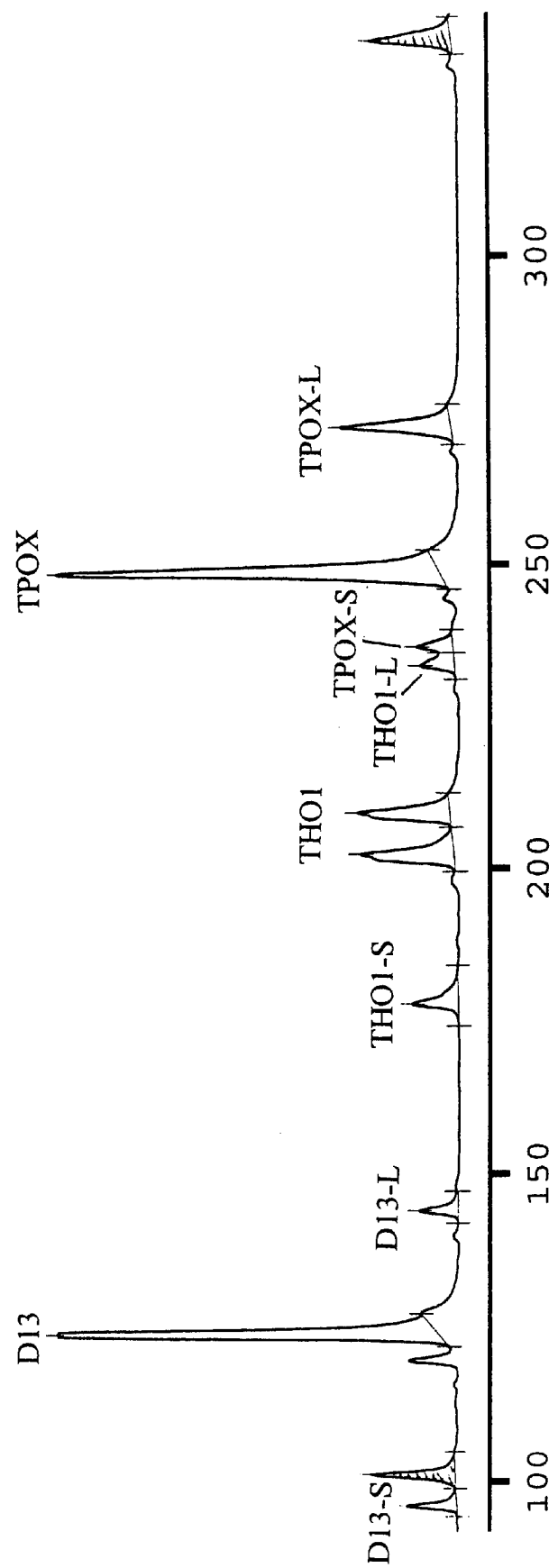
FIG. 27 is a printed image from the ALFexpress automated sequencer (Amersham Pharmacia Biotech) showing the fluorescent detection upon electrophoresis of the PCR product after amplification of the loci from multiplex subset D1: D13S317, TH01, and TPOX, and their Locus Specific Brackets (LSB). D13-S and D-13-L: short and long LSBs, respectively, for locus D13S317; TH01-S and TH01-L: short and long LSBs, respectively, for locus TH01; TPOX-S and TPOX-L: short and long LSBs, respectively, for locus TPOX. Peak areas correspond to fluorescence intensity and are depicted graphically as a function of fragment length (nt). Fluorescent peaks measured at 101 and 335 nt represent DNA size standards.

Each short and long LSB for D1 loci was amplified from its locus LSB template (Dau et al LSB patent) by the same primer pair used in Subset D1 in a single PCR vessel. The number of repeats in each LSB are shown in Table 1. The mixture of each individual LSB PCR amplicon of C1 loci was added into Multiplex Subset D1 PCR amplicons (same as those in FIG. 4) and co-electrophoresed in a single gel lane on ALF Express. PCR and electrophoresis conditions were as described in Methods. Reference is made to FIG. 27 which displays the amplified DNA fragments from each locus and their LSB templates according to their size (nt) dependent migration in a single gel lane. Individual fragments are identified by the length of the expected amplicons from their locus.

Example 28

Electrophoresis of Multiplex Subset D4 Loci D13S317, TH01, TPOX, and CSF1PO and Their Locus Specific Brackets (LSB)

Figure 28:
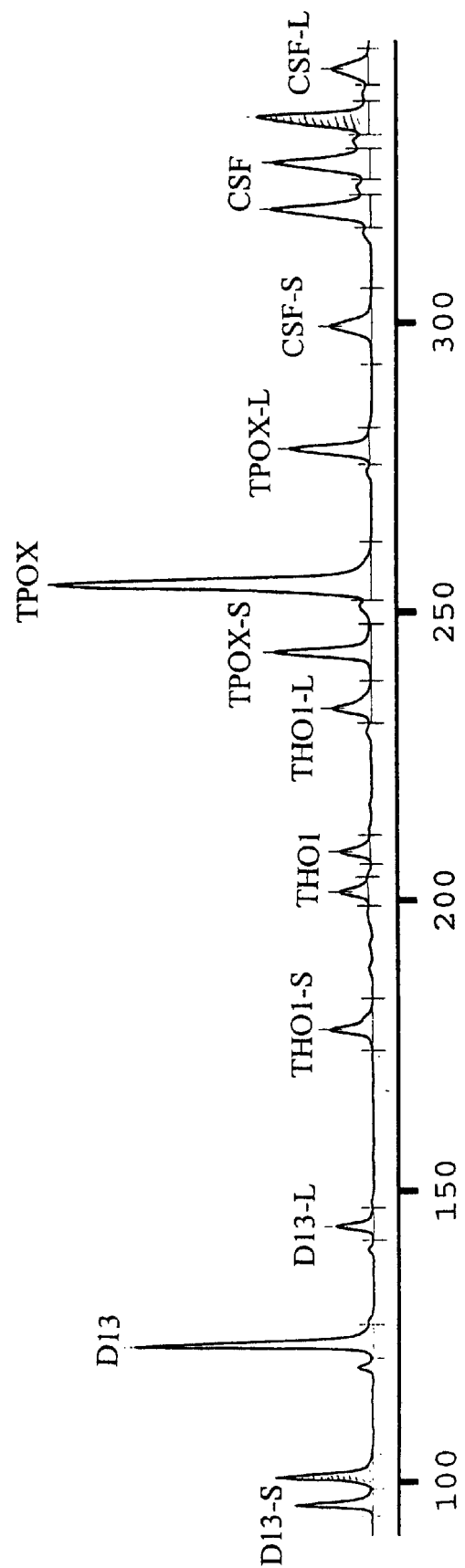
FIG. 28 is a printed image from the ALFexpress automated sequencer (Amersham Pharmacia Biotech) showing the fluorescent detection upon electrophoresis of the PCR product after amplification of the loci from multiplex subset D4: D13S317, TH01, TPOX, and CSF1PO, and their Locus Specific Brackets (LSB). D13-S and D13-L: short and long LSBs, respectively, for locus D13S317; TH01-S and TH01-L: short and long LSBs, respectively, for locus TH01; TPOX-S and TPOX-L: short and long LSBs, respectively, for locus TPOX; CSF-S and CSF-L: short and long LSBs, respectively, for locus CSF1PO. Peak areas correspond to fluorescence intensity and are depicted graphically as a function of fragment length (nt). Fluorescent peaks measured at 101 and 335 nt represent DNA size standards.

Each short and long LSB for D3 loci was amplified from its locus LSB template (Dau et at., U.S. Patent) by the same primer pair used in Subset D1 in a single PCR vessel. The number of repeats in each LSB are shown in Table 1. The mixture of each individual LSB PCR amplicon of C1 loci was added into Multiplex Subset D3 PCR amplicons (same as those in FIG. 15) and co-electrophoresed in a single gel lane on ALF Express. PCR and electrophoresis conditions were as described in Methods. Reference is made to FIG. 28 which displays the amplified DNA fragments from each locus and their LSB templates according to their size (nt) dependent migration in a single gel lane. Individual fragments are identified by the length of the expected amplicons from their locus.

Example 29

Amplification and Electrophoresis of Compound Multiplex IV: A3 Loci: vWA, D21S11, and D18S51; B3 Loci: D3S1358, D8S1179, D16S539, and CSF1PO; C4 Loci: D5S818, D7S820, and FGA; and D3 Loci: D13S317, THO, and TPOX and Their Locus Specific Brackets (LSB)

Figure 29:
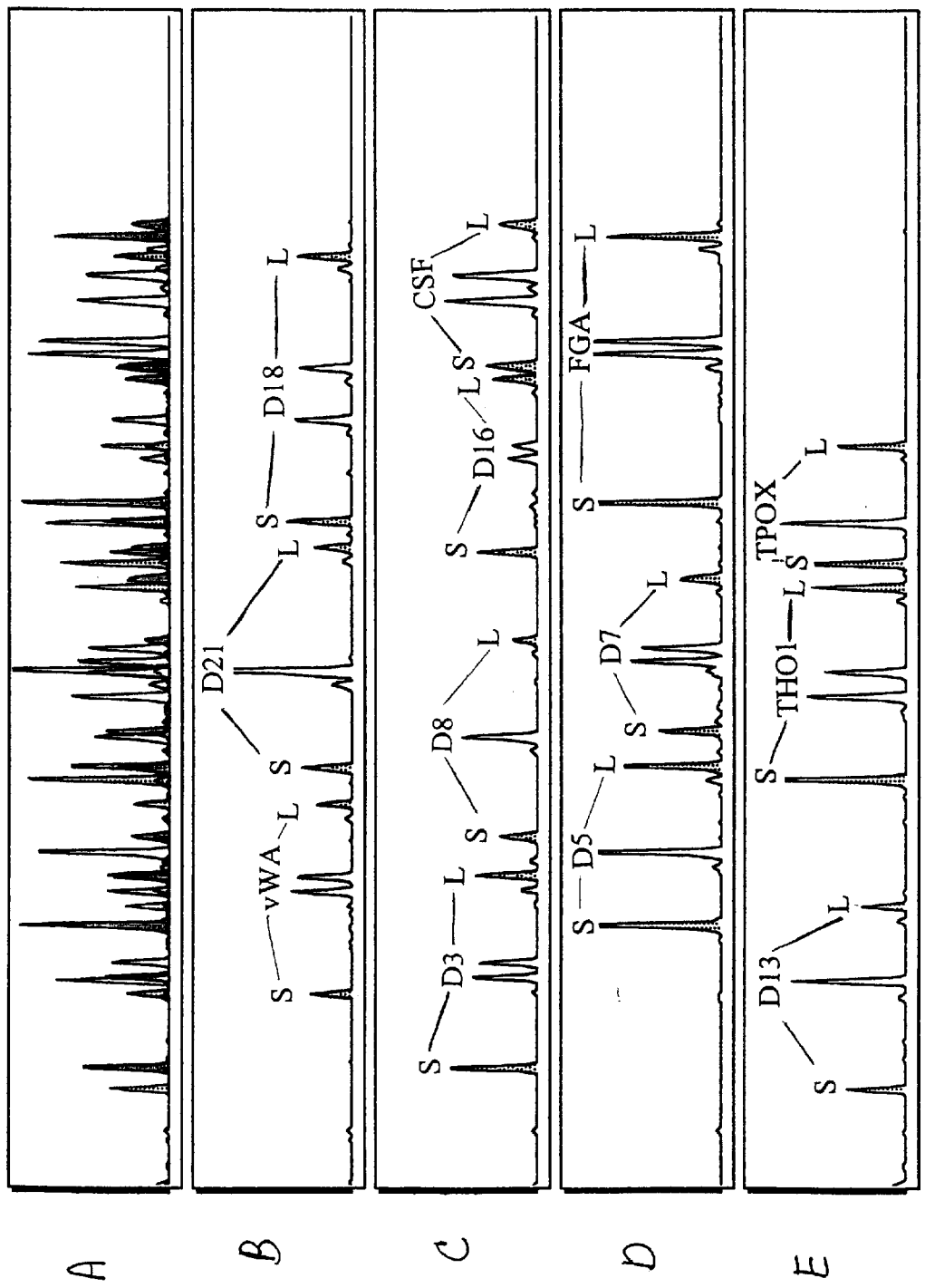
FIGS. 29A, 29B, 29C, 29D, and 29E are printed images from the ABI PRISM 310 Genetic Analyzer (PE Applied Biosystems, Foster City, Calif.) showing the fluorescent detection upon electrophoresis of the PCR product after amplification of the loci from individual subsets A3: vWA, D21S11", and D18S51' (FIG. 29B); B3: D3S1358', D8S1179, D16S539, and CSF1PO (FIG. 29C); C4: D5S818', D7S820, and FGA (FIG. 29D); and D3: D13S317, TH01, and TPOX' (FIG. 29E); and after combined amplification as Compound Multiplex IV (FIG. 29A), together with their Locus Specific Brackets (LSB). S=short LSB of the indicated locus; L=long LSB of the indicated locus. Peak areas correspond to fluorescence intensity and are depicted graphically as a function of fragment length (nt). Fluorescent peaks measured at 101 and 335 nt represent DNA size standards.

Each short and long LSB for all 13 CODIS loci was amplified from its locus LSB template (Dau et al., U.S. Pat. No. 6,013,444) by the same primer pair used in Compound Multiplex IV (Example 13) in a single PCR vessel. The number of repeats in each LSB are shown in Table 1. The mixture of each individual LSB PCR amplicon of Compound Multiplex IV loci was added into Compound Multiplex IV PCR amplicons (same as those in FIG. 13) and co-electrophoresed in a single gel lane on an ABI PRISM 310 Genetic Analyzer. PCR and electrophoresis conditions were as described in Example 13. Reference is made to FIGS. 29A–29E which display the amplified DNA fragments from each locus and their LSB templates according to their size (nt) dependent migration in a single gel lane. FIG. 29A shows combined sample alleles from 13 CODIS, loci and their LSBs labeled with 4 different fluorophores; 29B shows sample alleles from Subset A3 loci and their LSBs labeled with TAMRA; 29C shows sample alleles from Subset B3 loci and their LSBs labeled with ROX; 29D shows sample alleles from Subset C4 and their LSBs labeled with JOE; and 29E shows sample alleles and their LSBs labeled with FAM. Individual fragments are identified by the length of the expected amplicons from their locus and their LSB template.

Example 30

Evaluation of Measurement Accuracy of Alleles from 13 CODIS Loci Using LSB as Standards Three genetic DNA samples, NA09947A and NA09948A (NIGMS Human Genetic Mutant Cell Repository, Coriell Institute for Medical Research, Camden, N.J.), and K562 (LIFE TECHNOLOGIES, Baltimore, Md.), were each PCR amplified using each of the primer mixtures used for Multiplex Subsets A1, B 1, C1 and D1 in single vessels, the primer mixtures used for Multiplex Subsets A1, B 1, C1 and D1 in single vessels, long LSB templates (Dau et al., U.S. Pat. No. 6,013,444) with the primers used for amplifying the four Multiplex Subsets in a single PCR vessel. Pfu DNA polymerase and its 10×buffer (Stratagene, La Jolla, Calif.) were used at a final concentration of 0.075 U/$\mu$l. Each PCR was carried out in a 10 $\mu$l reaction volume. PCR amplicons from each subset and their LSBs were co-electrophoresed in a single gel lane on the ALFexpress. Measurement results are shown in Table 4. A multiple marker (MM) heterologous DNA calibration ladder was purchased from Pharmacia. For each of the three genomic DNA samples LSB as internal standard combined with LSB plus 1 common allele from each locus as an external standard were most accurate, followed by LSB as an internal standard combined with MM as an external standard, and finally LSB as an internal standard alone. The largest error registered for the first combination was 0.2 nt, for the second 0.5 nt and for the third 0.6 nt. The average error and standard deviation based on the absolute error value measured from all 3 DNA samples are 0.06±0.07 nt for the first combination, for the second combination 0.11±0.14 nt, and for the third combination 0.33±0.48 nt. These results show that LSB as internal standards were most accurate when used in concert with LSB as external standards combined with 1 common allele from each locus.

TABLE 4

Measurement of Three Genomic DNA Samples Using LSB and Multiple Markers (MM) as External and/or Internal Lane Standards

Sample NA09947A

| Locus | Alleles | Expected Length (bp) | MM External LSB Internal | LSB + 1 True Allele External LSB Internal | LSB Internal |
|---|---|---|---|---|---|
| *Subset A1* | | | | | |
| vWA | 17 | 144 | 144 | 144 | 143.5 |
| vWA | 18 | 148 | 148 | 148 | 147.6 |
| D21S11 | 30 | 209 | 209 | 209 | 208.6 |
| D21S11 | 30 | 209 | 209 | 209 | 208.6 |
| D18S51 | 15 | 280 | 280 | 280 | 279.9 |
| D18S51 | 19 | 296 | 296 | 296 | 295.9 |
| *Subset B1* | | | | | |
| D3S1358 | 14 | 123 | 122.9 | 123 | 122.4 |
| D3S1358 | 15 | 127 | 126.8 | 126.9 | 126.4 |
| D8S1179 | 13 | 188 | 188.2 | 187.9 | 187.8 |
| D8S1179 | 13 | 188 | 188.2 | 187.9 | 187.8 |
| D16S539 | 11 | 272 | 272 | 272.2 | 271.9 |
| D16S539 | 12 | 276 | 276.1 | 276.2 | 276 |
| CSF1PO | 10 | 319 | 319 | 319 | 319 |
| CSF1PO | 12 | 327 | 327.1 | 327 | 327.1 |
| *Subset C1* | | | | | |
| D5S818 | 11 | 155 | 155 | 155 | 154.7 |
| D5S818 | 11 | 155 | 155 | 155 | 154.7 |
| D7S820 | 10 | 212 | 212 | 212 | 211.8 |
| D7S820 | 11 | 216 | 216 | 216.1 | 215.8 |
| FGA | 23 | 304 | 304 | 304 | 304 |
| FGA | 24 | 308 | 308.1 | 308.1 | 308 |
| *Subset D1* | | | | | |
| D13S317 | 11 | 123 | 122.7 | 123.1 | 122.5 |
| D13S317 | 11 | 123 | 122.7 | 123.1 | 122.5 |
| TH01 | 8 | 201 | 201 | 201.1 | 200.7 |
| TH01 | 9.3 | 208 | 208 | 208.1 | 207.6 |
| TPOX | 8 | 248 | 248.3 | 247.8 | 248.2 |
| TPOX | 8 | 248 | 248.3 | 247.8 | 248.2 |

Sample NA09948A

| Locus | Alleles | Expected Length (bp) | MM External LSB Internal | LSB External LSB Internal | LSB Internal |
|---|---|---|---|---|---|
| *Subset A1* | | | | | |
| vWA | 17 | 144 | 144 | 144 | 143.5 |
| vWA | 17 | 144 | 144 | 144 | 143.5 |
| D21S11 | 29 | 205 | 205.1 | 205 | 204.6 |
| D21S11 | 30 | 209 | 209.1 | 209 | 208.6 |
| D18S51 | 15 | 280 | 280 | 280 | 279.9 |
| D18S51 | 18 | 292 | 291.9 | 291.9 | 291.9 |
| *Subset B1* | | | | | |
| D3S1358 | 15 | 127 | 126.9 | 127.1 | 126.4 |
| D3S1358 | 17 | 135 | 134.8 | 135 | 134.5 |
| D8S1179 | 12 | 184 | 184.2 | 184 | 183.8 |
| D8S1179 | 13 | 188 | 188.3 | 188.1 | 183.8 |
| D16S539 | 11 | 272 | 271.9 | 271.8 | 271.8 |
| D16S539 | 11 | 272 | 271.9 | 271.8 | 271.8 |
| CSF1PO | 10 | 319 | 319 | 319 | 319 |
| CSF1PO | 11 | 323 | 323 | 323 | 323 |
| *Subset C1* | | | | | |
| D5S818 | 11 | 155 | 155.1 | 155 | 154.7 |
| D5S818 | 13 | 163 | 163.1 | 163 | 162.8 |
| D7S820 | 11 | 216 | 216. | 215.9 | 215.8 |
| D7S820 | 11 | 216 | 216 | 215.9 | 215.8 |
| FGA | 24 | 308 | 308 | 308 | 308 |
| FGA | 26 | 316 | 316 | 316 | 316 |
| *Subset D1* | | | | | |
| D13S317 | 11 | 123 | 122.6 | 122.9 | 122.5 |
| D13S317 | 11 | 123 | 122.6 | 122.9 | 122.5 |

TABLE 4-continued

Measurement of Three Genomic DNA Samples Using LSB and Multiple Markers (MM) as External and/or Internal Lane Standards

| Locus | Alleles | Expected Length (bp) | MM External LSB Internal | LSB External LSB Internal | LSB Internal |
|---|---|---|---|---|---|
| TH01 | 6 | 193 | 192.9 | 192.9 | 192.6 |
| TH01 | 9.3 | 208 | 207.9 | 207.9 | 207.5 |
| TPOX | 8 | 248 | 248.3 | 248.1 | 248.3 |
| TPOX | 9 | 252 | 252.5 | 252.2 | 252.5 |
| Sample K562 | | | | | |
| Subset A1 | | | | | |
| vWA | 16 | 140 | 140 | 140 | 139.5 |
| vWA | 16 | 140 | 140 | 140 | 139.5 |
| D21S11 | 29 | 205 | 205 | 205 | 204.6 |
| D21S11 | 30 | 209 | 209.1 | 209.1 | 208.7 |
| D21S11 | 31 | 213 | 213 | 213 | 212.6 |
| D18S51 | 15 | 280 | 280.1 | 280 | 280 |
| D18S51 | 16 | 284 | 284 | 284 | 283.9 |
| Subset B1 | | | | | |
| D3S1358 | 16 | 131 | 130.9 | 131 | 130.5 |
| D3S1358 | 16 | 131 | 130.9 | 131 | 130.5 |
| D8S1179 | 12 | 184 | 184.2 | 184 | 183.7 |
| D8S1179 | 12 | 184 | 184.2 | 184 | 183.7 |
| D16S539 | 11 | 272 | 271.8 | 271.8 | 271.7 |
| D16S539 | 12 | 276 | 275.8 | 275.8 | 275.7 |
| CSF1PO | 9 | 315 | 315 | 315 | 315 |
| CSF1PO | 10 | 319 | 319 | 319 | 319 |
| Subset C1 | | | | | |
| D5S818 | 11 | 155 | 155.1 | 155.1 | 154.8 |
| D5S818 | 12 | 159 | 159 | 159 | 158.7 |
| D7S820 | 9 | 208 | 208 | 208 | 207.8 |
| D7S820 | 11 | 216 | 216 | 215.9 | 216.1 |
| FGA | 21 | 296 | 296 | 296 | 296 |
| FGA | 1 | 308 | 308.1 | 308.1 | 308.1 |
| Subset D1 | | | | | |
| D13S317 | 8 | 111 | 110.5 | 111 | 110.5 |
| D13S317 | 8 | 111 | 110.5 | 111 | 110.5 |
| TH01 | 9.3 | 208 | 207.9 | 207.9 | 207.6 |
| TH01 | 9.3 | 208 | 207.9 | 207.9 | 207.6 |
| TPOX | 8 | 248 | 248.3 | 248.1 | 248.3 |
| TPOX | 9 | 252 | 252.4 | 252.0 | 252.4 |

Figure 30:
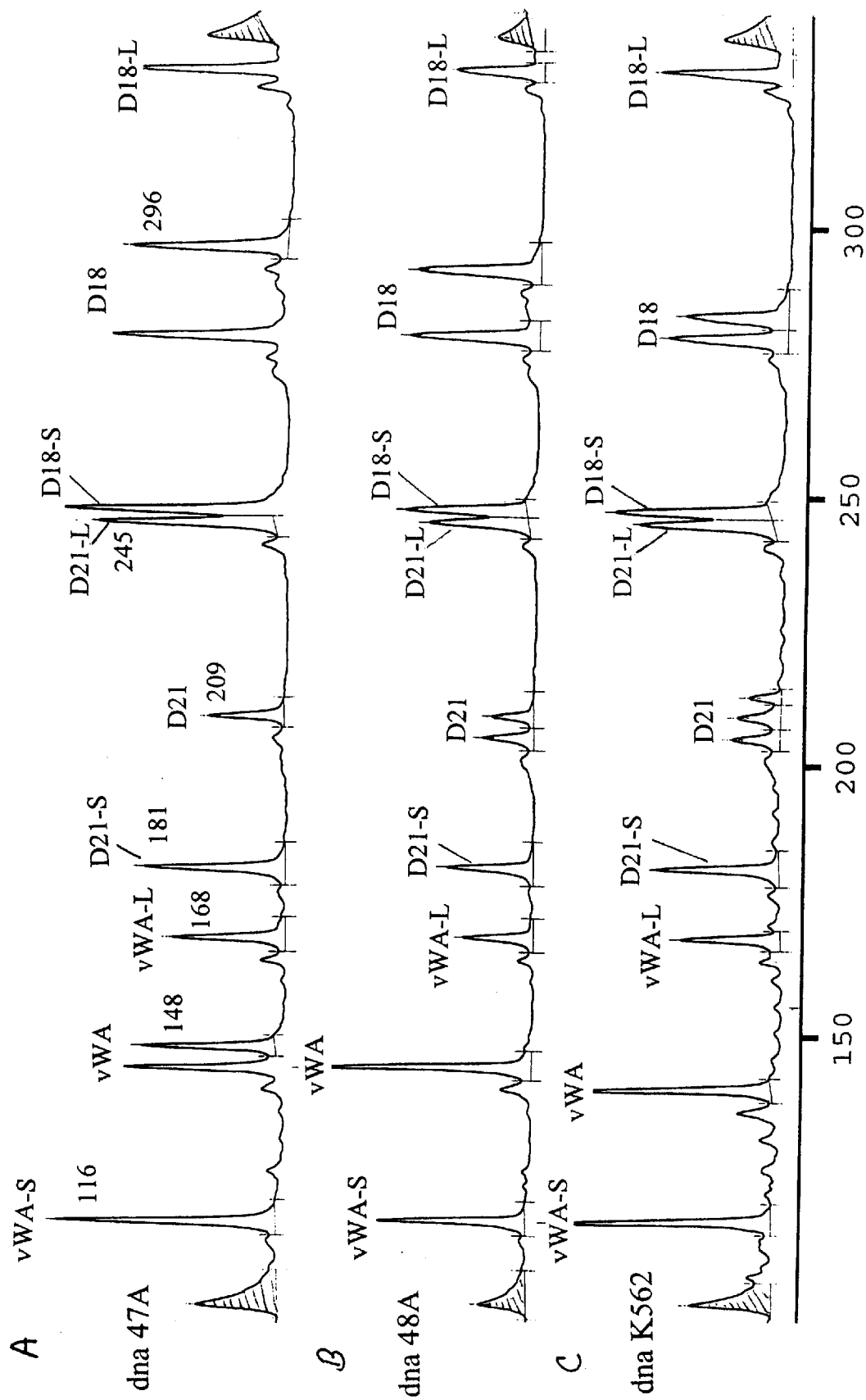
FIGS. 30A, 30B and 30C are printed images from the ALFexpress automated sequencer (Amersham Pharmacia Biotech) showing the fluorescent detection upon electrophoresis of the PCR product after amplification of the subset A1 loci from genomic DNAs NA09947A (30A), NA09948A (30B) and K562 (30C): vWA, D21S11, D18S51, and their Locus Specific Brackets (LSB). vWA-S and vWA-L: short and long LSBs, respectively, for locus vWA; D21-S and D21-L: short and long LSBs, respectively, for locus D21S11; D18-S and D18-L: short and long LSBs, respectively, for locus D18S51. Peak areas correspond to fluorescence intensity and are depicted graphically as a function of fragment length (nt). Fluorescent peaks measured at 101 and 335 nt represent DNA size standards.

Example 31
Multiple Markers (MM) Employed as Internal Lane Standards in Combination with MM or LSB and Their Alleles as External Lane Standards Example 31 describes the usefulness of MM in the calibration of target alleles labeled with the same fluorophore. In order to calibrate the electrophoretic fragment lengths of alleles from subset A1 (vWA, D21S11, and D18S51) MM of 101 and 335 bp were arbitrarily selected from the genetically unrelated LPL and F13A01 loci because these fragment lengths served to bracket the target alleles. Additional MM could be designed to migrate between their target alleles as needed to improve calibration (Table 5, column 10) without overlapping them. All target loci and MM were labeled with the Cy5 fluorophore and co-electrophoresed on the ALFexpress instrument as described in Example 26. FIGS. 30A–30C show their co-electrophoresis after PCR amplification of A1 loci from genomic DNA samples NA09947A (FIG. 30A), NA09948A (FIG. 30B), and K562 (FIG. 30C). The measurement of their A1 alleles employing the MM as internal and external lane calibration together with various locus specific external lane calibration markers is given in Table 5 columns 4–6. With MM and LSB plus one allele from each locus (column 4) as external lane standards and MM as internal standards the measurement errors were 0.0 nt for vWA, less than or equal to 0.1 for D21S11, and 0.1 to 1.4 nt for D18S51. With the LSB plus 2 alleles from each locus as the additional external standard (column 5) there was no error greater than 0.1 nt.

The necessity for an external lane calibration system with LSB or locus specific alleles to bracket the fragment lengths of target loci is shown in column 6, where the long LSB was removed from each locus. A large measurement error of 1.2 nt appeared for allele 19 of D18S51 from sample 47A, because the two alleles, 16 and 19, applied as external standards for its locus did not bracket its allele 19. D18S51 alleles from samples 48A and K562 were measured by alleles 15 and 19, so its alleles, 15 and 18, remained bracketed and were still measured within 0.1 nt. When the short LSB rather than the long LSB was removed (column 7), the calibration error increased slightly because the shortest marker allele (15) was equal to but did not bracket the shortest target allele in length. Therefore, preferred external calibration standards are bracketing rather than equal in length to their target alleles. In conclusion, calibration of STR alleles can be effected with 2 or more unrelated MM as internal lane standards when 1) they at least bracket the alleles of their target loci and may be interspersed between them upon co-electrophoresis in the same channel and are labeled with the same fluorophore, and 2) they are also deployed in external channel calibration in combination with at least three locus specific markers (LSB or alleles) bracketing the length of the target alleles of each locus, all of which are labeled with the same fluorophore.

MM differing in length or sequence may vary in their calibration when used as internal and external standards combined with LSB and/or true alleles. Two MM, of 91 and 386 nt, derived from the T cell receptor alpha locus, were used as external and internal standards to replace the MM of 101 and 335 nt in column 8 in bracketing A1 alleles for measurement. As shown in Column 8 of Table 5, the measurement error varied from 0 to 0.2 nt for vWA, 0 to 0.3 nt for D21S11, and 0 to 0.4 nt for D18S51. The reduced but variable measurement error compared to those recorded with MM 101/335 indicates that the mobility of MM 91/386 is generally more comparable to A1 alleles, especially D18S51, than is the mobility of MM 101/335.

In order to test if additional D18S51 locus specific alleles employed as external standards would increase measurement accuracy, they were used to measure all alleles of D18S51, namely 8 through 27 including alleles 10.2 and 13.2 [obtained from a commercial (Promega) allelic ladder (FIG. 31)]. As shown in Table 6 columns 5–6 and 8–9, one or two alleles were used as external standards combined with their LSBs (D18-S and D18-L) and MM 91/386. MM 91/386 was employed as the internal standard in columns 4–5, and LSB were employed in columns 8–9. Short and long LSBs of D18S51, one D18S51 true allele and 91/386 MM (column 5) employed as the external standard gave a mean measurement error of 0.53±0.13 nt, but the same configuration with 2 alleles instead of 1 reduced the mean error to 0.13 nt (column 6). Use of LSB externally with the entire allelic ladder in place of 1 or 2 alleles gave an intermediate mean error of 0.22 nt (column 4). Without external LSB and with internal LSB in place of MM, this error increased to 0.28 nt (column 7). Therefore, no improvement in measurement accuracy of the allelic ladder alleles was found when all alleles in the allelic ladder plus 2 bracketing MM were used as external standards compared to LSB plus two true alleles and MM when both were combined with the bracketing MM as the internal standard. Additionally, alleles as external lane standards could not be replaced by a MM ladder: the measurement of D18S51 in its allelic ladder by 91/386 plus Pharmacia MM in the external lane showed a large mean error of 1.77 nt (column 3). The use of 91/386 as additional external lane standards did not enhance the excellent calibration registered by LSB in the external and internal lanes combined with one or two alleles in the external lane (columns 8–11).

TABLE 5

Measurement of Three Genomic DNA Samples Using Multiple Markers As External and Internal Lane Standards

| 1 Locus/ Allele | 2 Expected Length (bp) | 3 Run Time (min) | 4 101/335 LSBs + 1 allele as External Internal 101/335 | 5 101/335 LSBs + 2 alleles as External Internal 101/335 | 6 101/335 LSB short 1 or 2 alleles as External Internal 101/335 | 7 101/335 LSB long 1 or 2 alleles as External Internal 191/386 | 8 91/386 LSBs + 1 allele as External Internal 91/386 | 9 91/386 Allelic ladder as External Internal 91/386 | 10 91/386 Allelic ladder as External Internal 245/335 |
|---|---|---|---|---|---|---|---|---|---|
| NA09947A | | | | | | | | | |
| vWA/17 | 144 | 132.6 | 144 | | 143.7 | 144 | 144 | | |
| vWA/18 | 148 | 135.2 | 148 | | 147.5 | 148 | 148 | | |
| D21S11/30 | 209 | 175.13 | 208.9 | 209 | 209 | 209 | 208.9 | | |
| D21S11/30 | 209 | 175.13 | 208.9 | 209 | 209 | 209 | 208.9 | | |
| D18S51/15 | 280 | 223.3 | 279.4 | 279.9 | 279.9 | 279.8 | 280 | 279.9 | 270.9 |
| D18S51/19 | 296 | 234.2 | 295.9 | 295.9 | 294.8 | 295.9 | 296.2 | 295.9 A/16 | 295.9 |
| NA09948A | | | | | | | | | |
| VWA/17 | 144 | 133.1 | 144 | 144 | 144 | 144 | 143.8 | | |
| VWA/17 | 144 | 133.1 | 144 | 144 | 144 | 144 | 143.8 | | |
| D21S11/29 | 205 | 156.77 | 205 | 205.1 | 205 | 205.1 | 204.7 | | |
| D21S11/30 | 209 | 175.67 | 209 | 209.1 | 209 | 209.1 | 208.7 | | |
| D18S51/15 | 280 | 223.9 | 278.6 | 280.1 | 280.1 | 280.1 | 279.7 | 279.6 | 279.9 |
| D18S51/18 | 292 | 232.03 | 291.5 | 292 | 292 | 291.7 | 291.6 | 291.5 | 291.9 |
| K562 | | | | | | | | | |
| VWA/16 | 140 | 130.23 | 140 | 140.1 | 140 | 140.1 | 140 | | |
| VWA/16 | 140 | 130.23 | 140 | 140.1 | 140 | 140.1 | 140 | | |
| D21S11/29 | 205 | 172.6 | 205 | 204.9 | 204.9 | 204.9 | 205.1 | | |
| D21S11/30 | 209 | 175.4 | 209.1 | 209 | 209.1 | 204.9 | 209 | | |
| D21S11/31 | 213 | 178.07 | 213 | 212.9 | 213 | 212.9 | 213.1 | | |
| D18S51/15 | 280 | 223.67 | 278.7 | 280.1 | 280.1 | 280.1 | 280 | 279.8 | 279.8 |
| D18S51/16 | 284 | 226.37 | 282.8 | 284.1 | 284.1 | 283.8 | 284 | 283.9 | 279.8 |
| Mean | | | 0.28 | 0.06 | | | 0.12 | | |
| SD* | | | 0.48 | 0.05 | | | 0.13 | | |

*SD = standard deviation

TABLE 6

Measurement of the D18S51 Allelic Ladder Using Multiple Markers, LSB, and D18S51 Alleles as Calibration Standards

| 1 Allele No. | 2 Expected Length | 3 External: 91/386 MM Internal: 91/386 (nt) | 4 External: 91/386 Ladder LSB Internal: 91/386 (nt) | 5 External: 91/386 one allele LSB Internal: 91/386 (nt) | 6 External: 91/386 two alleles LSB Internal: 91/386 (nt) | 7 External: 91/386 Ladder LSB (nt) | 8 External: 91/386 one allele LSB Internal: LSB (nt) | 9 External: 91/386 two alleles LSB Internal: LSB (nt) | 10 External: one allele LSB Internal: LSB (nt) | 11 External: two alleles LSB Internal: LSB (nt) |
|---|---|---|---|---|---|---|---|---|---|---|
| LSB-S | 248 | | | | | | | | | |
| 8 | 252 | 251.3 | 252.2 | 252.3 | 252.1 | 252.2 | 252.0 | 252.1 | 252.0 | 252.1 |
| 9 | 258 | 255.2 | 258.2 | 256.3 | 256.1 | 256.2 | 256.0 | 256.1 | 256.1 | 256.2 |
| 10 | 260 | 259.0 | 260.3 | 260.4 | 260.3 | 260.1 | 260.0 | 260.1 | 260.0 | 260.1 |
| 10.2 | 282 | 261.2 | 262.4 | 262.7 | 262.6 | 262.1 | 262.2 | 262.4 | 262.3 | 262.4 |
| 11 | 264 | 262.7 | 264.3 | 264.2 | 264.1 | 264.2 | 263.8 | 264.0 | 263.9 | 264.0 |
| 12 | 268 | 266.7 | 268.3 | 268.4 | 268.2 | 268.1 | 267.9 | 268.1 | 267.9 | 268.1 |
| 13 | 272 | 270.7 | 272.3 | 272.5 | 272.3 | 272.2 | 272.0 | 272.1 | 272.0 | 272.1 |
| 14 | 276 | 274.3 | 276.4 | 276.3 | 276.1 | 276.1 | 275.7 | 275.8 | 275.7 | 275.8 |
| 15 | 280 | 278.4 | 280.3 | 280.4 | 280.1 | 280.2 | 279.9 | 280.0 | 280.0 | 280.0 |
| 16 | 284 | 282.2 | 284.3 | 284.5 | 284.1 | 284.2 | 283.9 | 284.0 | 283.9 | 284.0 |
| 17 | 288 | 286.2 | 288.2 | 288.5 | 288.1 | 288.2 | 288.0 | 288.0 | 288.0 | 288.0 |
| 18 | 292 | 290.1 | 292.2 | 292.5 | 292.0 | 292.3 | 292.0 | 292.0 | 292.0 | 292.0 |
| 19 | 296 | 294.0 | 296.2 | 296.6 | 296.1 | 296.3 | 296.0 | 296.0 | 296.0 | 296.0 |
| 20 | 300 | 298.0 | 300.1 | 300.6 | 300.0 | 300.4 | 300.1 | 300.0 | 300.1 | 300.0 |
| 21 | 304 | 301.9 | 304.2 | 304.7 | 304.1 | 304.3 | 304.1 | 304.0 | 304.1 | 304.0 |
| 22 | 308 | 305.8 | 308.1 | 306.6 | 306.0 | 308.4 | 308.1 | 308.1 | 308.1 | 308.0 |
| 23 | 312 | 309.6 | 312.2 | 312.7 | 312.1 | 312.4 | 312.1 | 312.1 | 312.1 | 312.0 |
| 24 | 316 | 313.5 | 316.1 | 316.7 | 316.1 | 316.4 | 316.1 | 316.1 | 316.1 | 316.0 |
| 25 | 320 | 317.5 | 320.1 | 320.7 | 320.1 | 320.5 | 320.1 | 320.1 | 320.2 | 320.0 |
| 26 | 324 | 321.3 | 324.1 | 324.8 | 324.1 | 324.5 | 324.1 | 324.1 | 324.2 | 324.1 |
| 27 | 328 | 325.2 | 328.1 | 328.8 | 328.1 | 328.5 | 328.1 | 328.1 | 328.2 | 328.1 |
| LSB-L | 332 | | | | | | | | | |
| Mean** | | 1.77 | 0.22 | 0.53 | 0.13 | 0.28 | 0.09 | 0.08 | 0.10 | 0.07 |
| SD** | | 0.64 | 0.10 | 0.18 | 0.13 | 0.14 | 0.08 | 0.09 | 0.09 | 0.10 |

Figure 31:
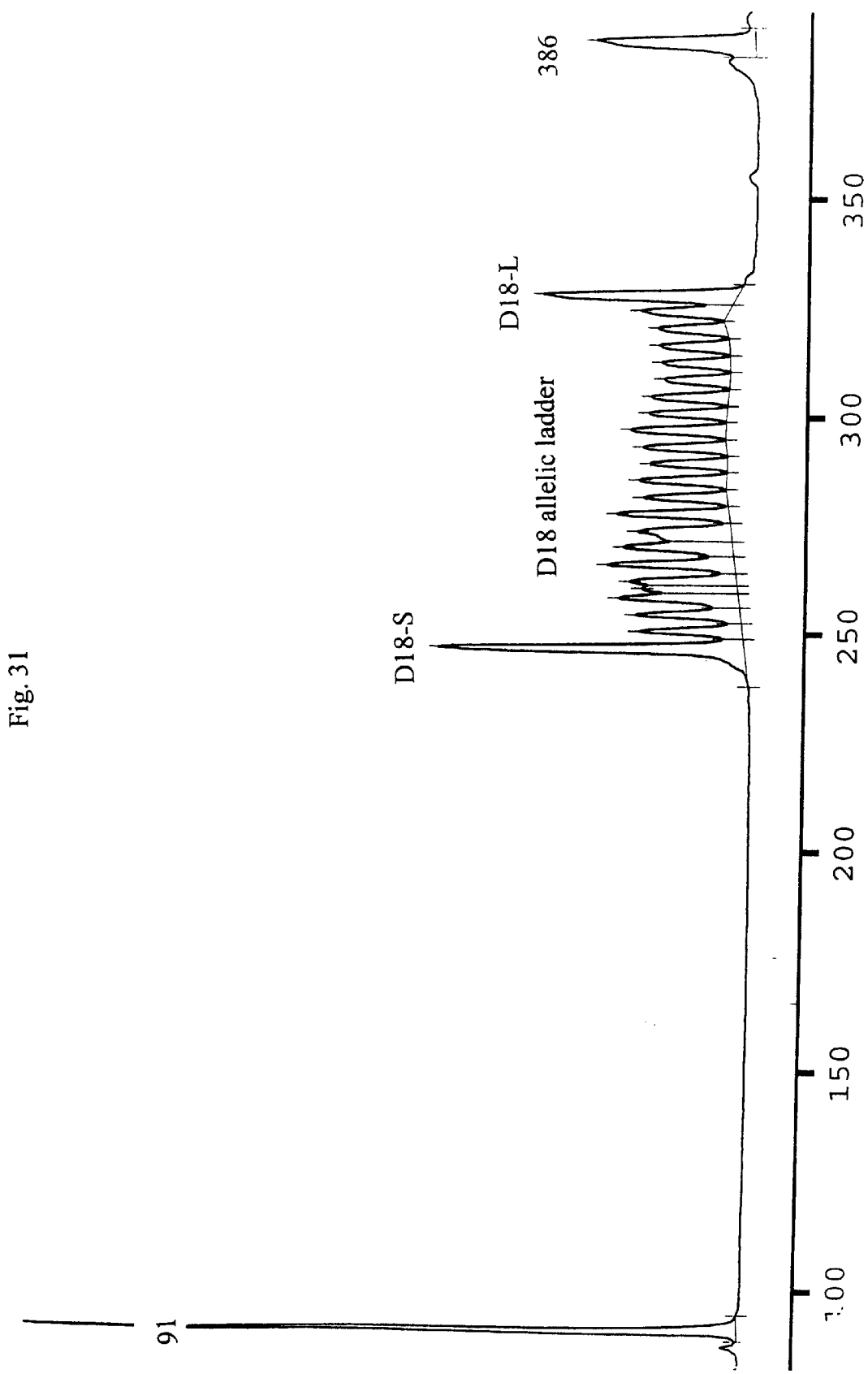
FIG. 31 is a printed image from the ALFexpress automated sequencer (Amersham Pharmacia Biotech) showing the fluorescent detection upon electrophoresis of the PCR products from the D18S51 allelic ladder (Promega), locus specific brackets (LSB) from the D18S51 locus: D18-S and D18-L and multiple markers (MM) of 91 and 386 bp. Peak areas correspond to fluorescence intensity and are depicted graphically as a function of fragment length (nt).

*Allele 13.2 in the D18S51 allelic ladder was not resolved under this electrophoresis as shown in FIG. 31.
**Variance of measured lengths from expected lengths
***Multiple markers from 100 to 450 bp with 50 bp interval (Amersham Pharmacia Biotech)

Example 32
Amplification and Electrophoresis of Multiplex Subset C6 Loci D13S317 and FGA In order to obtain accurately measured PCR amplicons of <350 bp in length from rare (Griffiths, 1998) as well as all common alleles from the FGA locus, additional room needed to be created within its subset to allow a detection range adequate to encompass the entire polymorphism. A new reverse primer [SEQ ID NO: 40] was designed so that the FGA PCR amplicons amplified by the new reverse primer paired with the FGA forward primer used in subset C2 had a lowest possible size of 218 bp, 66 bp shorter than those obtained in subset C2. To free up space for these shorter FGA products, the amelogenin, D5S818 and D7S820 loci in subset C2 were exchanged for locus D13S317 in subset D3 creating the new subsets C6 and D5. Due to the shorter amplicons all known rare FGA alleles could now be amplified for analysis with a upper length of 348 bp.

Figure 32:
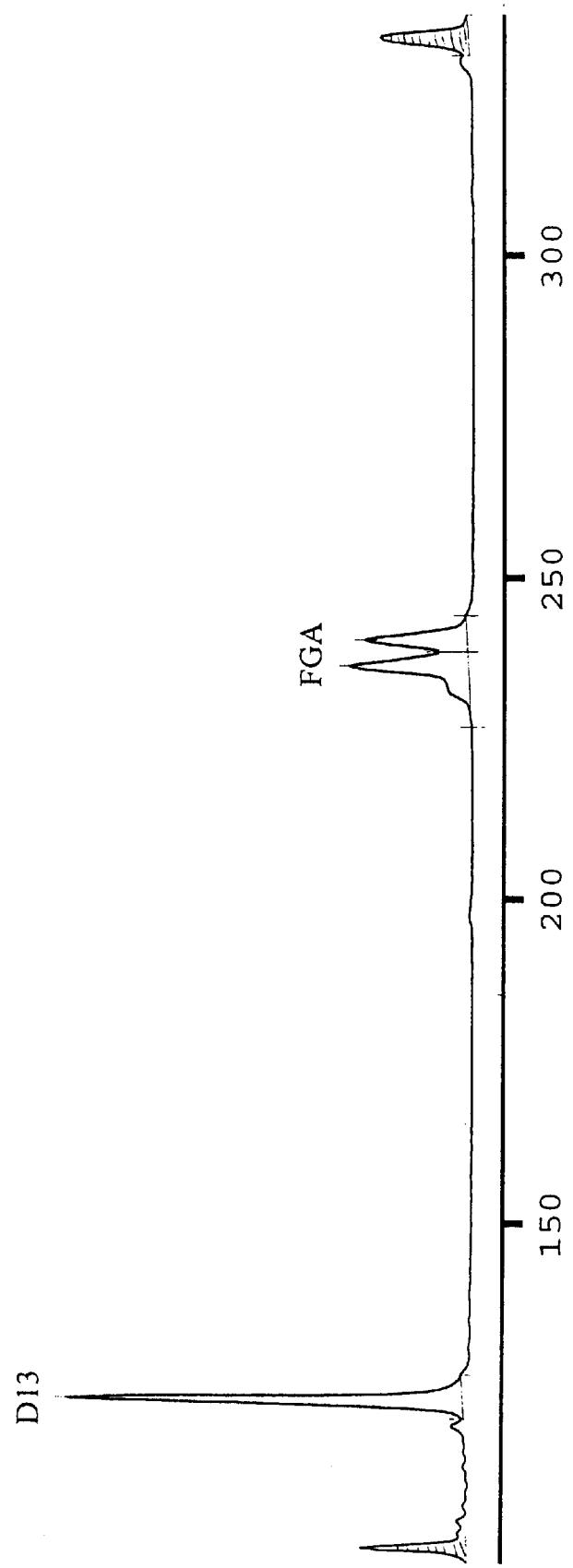
FIG. 32 is a printed image from the ALFexpress automated sequencer (Amersham Pharmacia Biotech) showing the fluorescent detection upon electrophoresis of the PCR product after amplification of the loci from multiplex subset C6: D13S317 and FGA". Peak areas correspond to fluorescence intensity and are depicted graphically as a function of fragment length (nt). Fluorescent peaks (shaded) measured at 101 and 335 nt represent DNA size standards.

In this example, PCR, electrophoresis conditions and data analysis for subset C6 were carried out as described in methods. The last 25 cycles of PCR were performed at a constant annealing temperature of 59° C. The loci in this example were amplified in a single PCR vessel in a 10 μl reaction volume; their PCR amplicons were analyzed in a single electrophoretic gel lane on ALFexpress. The final primer concentrations for each locus were: 0.24 μM each of D13S317 primers 1 [SEQ ID NO: 21] and 2 [SEQ ID NO: 22] and 1.5 μM each of FGA primers 1 [SEQ ID NO: 19] and 2 [SEQ ID NO: 40]. Reference is made to FIG. 32 which displays the amplified DNA fragments from each locus according to their size dependent migration in a single gel lane. Individual fragments are identified by the length (nt) of the expected amplicons from their locus.

Example 33
Amplification and Electrophoresis of Multiplex Subset D5 Loci Amelogenin, D5S818, D7S820, TPOX, and TH01

Figure 33:
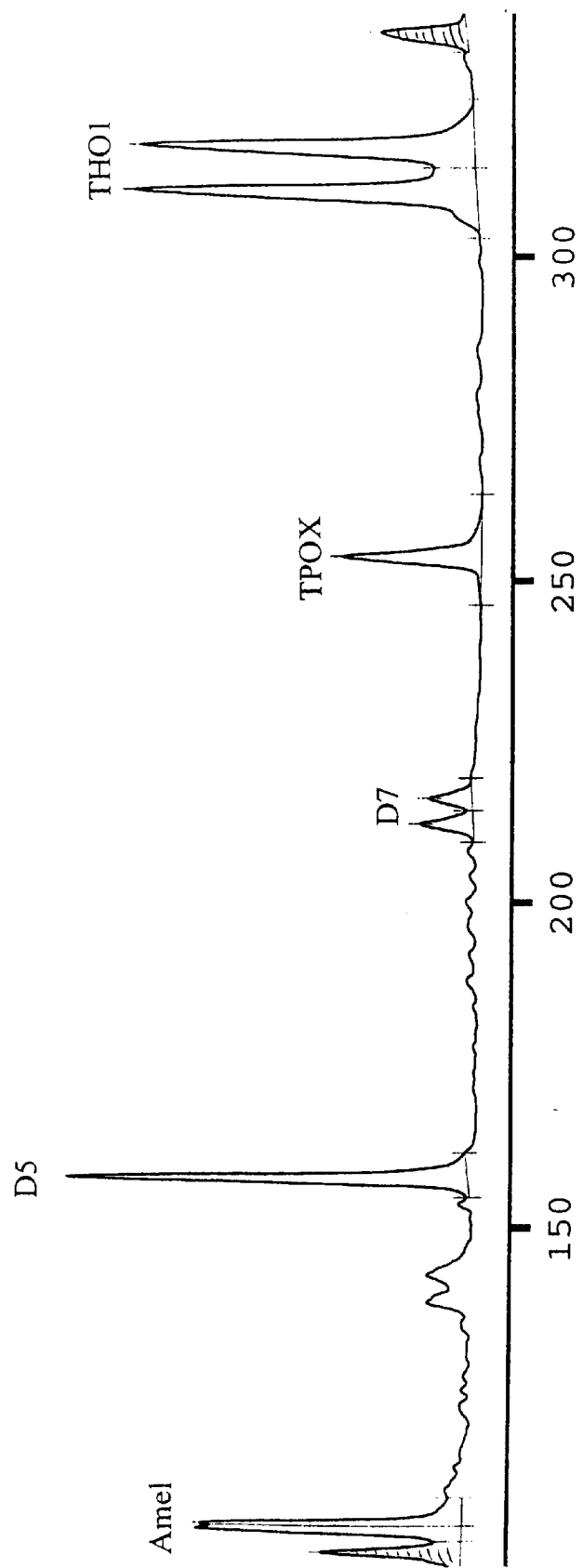
FIG. 33 is a printed image from the ALFexpress automated sequencer (Amersham Pharmacia Biotech) showing the fluorescent detection upon electrophoresis of the PCR product after amplification of the loci from multiplex subset D5: amelogenin, D5S818', D7S820, TPOX', and TH01". Peak areas correspond to fluorescence intensity and are depicted graphically as a function of fragment length (nt). Fluorescent peaks (shaded) measured at 101 and 335 nt represent DNA size standards.

Since the size range of the PCR amplicons of locus D7S820 overlapped with those of locus TH01 in the new subset D5, a new reverse primer for locus TH01 [SEQ ID NO: 41] was designed so that the length of its PCR amplicon became the longest in subset D5 (Table 1). In this example, PCR, electrophoretic conditions and data analysis were carried out as described in methods. The last 25 cycles of PCR were performed at a constant annealing temperature of 57° C. The loci in this example were amplified in a single PCR vessel in total 10 μl reaction volume and their PCR amplicons were analyzed in a single electrophoretic gel lane on the ALFexpress. The final primer concentrations in this PCR for each locus were: 0.18 μM each of amelogenin primers 1 [SEQ ID NO: 27] and 2 [SEQ ID NO: 28], 0.21 μM each of D5S818 primers 1 [SEQ ID NO: 15] and 2 [SEQ ID NO: 16], 1.2 μM each of D7S820 primers 1 [SEQ ID NO: 17] and 2 [SEQ ID NO: 18], and 0.15 μM each of TPOX primers 1 [SEQ ID NO: 25] and 2 [SEQ ID NO: 26], and 0.9 μM each of TH01 primers 1 [SEQ ID NO: 23] and 2 [SEQ ID NO: 41]. Reference is made to FIG. 33 which displays the amplified DNA fragments from each locus according to their size dependent migration in a single gel lane. Individual fragments are identified by the length (nt) of the expected amplicons from their locus.

Example 34
Electrophoresis of Multiplex Subset C6 Loci D13S317 and FGA, and Their Locus Specific Brackets (LSB)

Figure 34:
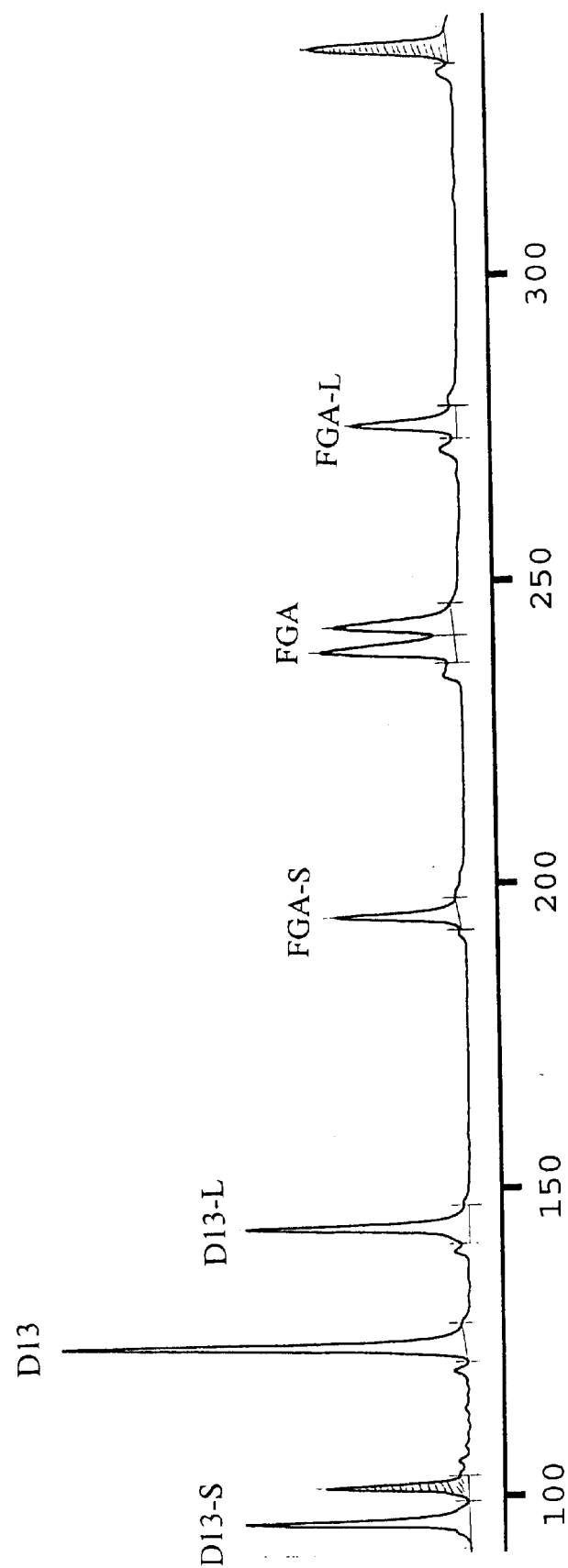
FIG. 34 is a printed image from the ALFexpress automated sequencer (Amersham Pharmacia Biotech) showing the fluorescent detection upon electrophoresis of the PCR product after amplification of the loci from multiplex subset C6: D13S317 and FGA", and their Locus Specific Brackets (LSBs). D13-S and D13-L: short and long LSBs, respectively, for locus D13S317; FGA"-S and FGA"-L: short and long LSBs, respectively, for locus FGA". Peak areas correspond to fluorescence intensity and are depicted graphically as a function of fragment length (nt). Fluorescent peaks (shaded) measured at 101 and 335 nt represent DNA size standards.

Each short and long LSB for C6 loci was amplified from its locus specific LSB template (Dau et al., U.S. Pat. No. 6,013,444) by the same primer pair used in subset C6 in a single PCR vessel. The number of repeat units contained in each LSB are shown in Table 1. A mixture of individual LSB PCR amplicons from C6 loci was added into multiplex subset C6 PCR amplicons (same as those in FIG. 32) and co-electrophoresed in a single gel lane on ALFexpress. PCR and electrophoresis conditions were as described in methods. Reference is made to FIG. 34 which displays the amplified DNA fragments from each locus and their LSB templates according to their size dependent migration in a single gel lane. Individual fragments are identified by the length (nt) of the expected amplicons from their locus.

Example 35

Electrophoresis of Multiplex Subset D5 Loci Amelogenin, D5S818, D7S820, TPOX, and TH01, and Their Locus Specific Brackets (LSB)

Figure 35:
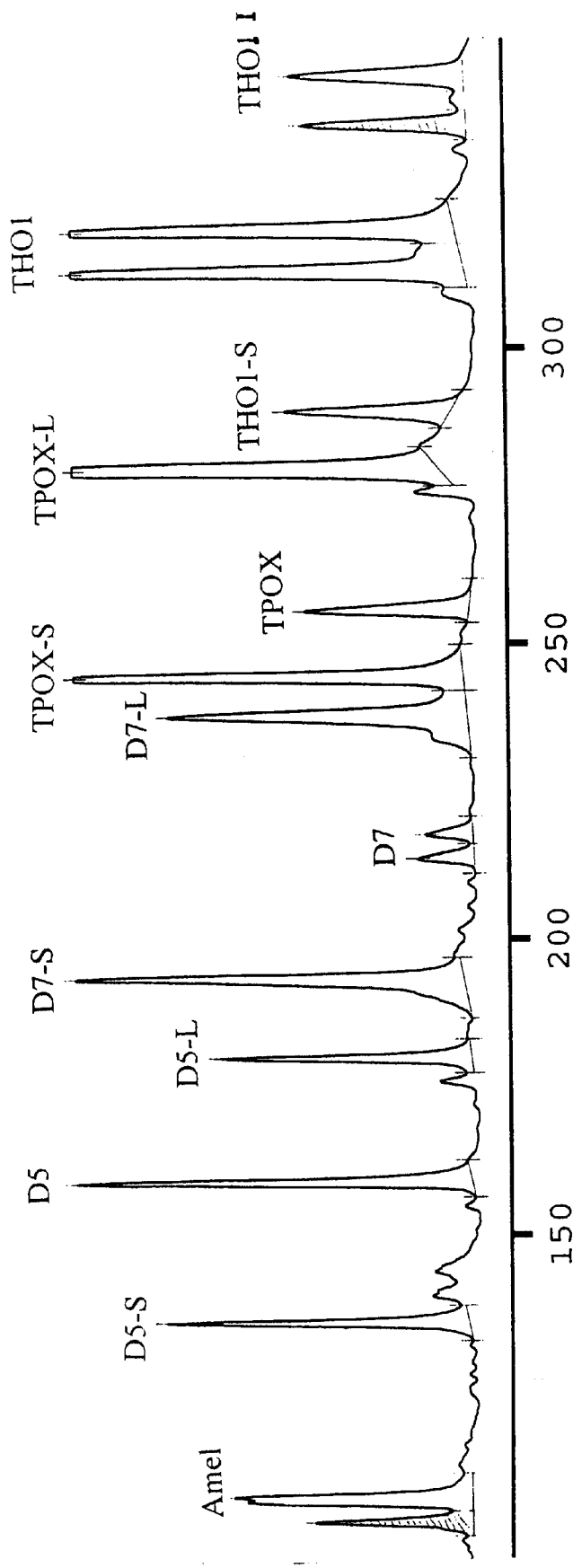
FIG. 35 is a printed image from the ALFexpress automated sequencer (Amersham Pharmacia Biotech) showing the fluorescent detection upon electrophoresis of the PCR product after amplification of the loci from multiplex subset D5: amelogenin, D5S818', D7S820, TPOX', and TH01", and their Locus Specific Brackets (LSBs). D5-S and D5-L: short and long LSBs, respectively, for locus D5S818; D7-S and D7-L: short and long LSBs, respectively, for locus D7S820; TPOX-S and TPOX-L: short and long LSBs, respectively, for locus TPOX'; TH01-S and TH01-L: short and long LSBs, respectively, for locus TH01". Peak areas correspond to fluorescence intensity and are depicted graphically as a function of fragment length (nt). Fluorescent peaks (shaded) measured at 101 and 335 nt represent DNA size standards.

LSB for D5 loci were amplified from their locus specific LSB templates (Dau et al., U.S. Pat. No. 6,013,444) by the same primer pair used in subset D5 in a single PCR vessel. The number of repeats in each LSB are shown in Table 1. The mixture of individual LSB PCR amplicons from D5 loci was added into subset D5 PCR amplicons (same as those in FIG. 33) and co-electrophoresed in a single gel lane on ALFexpress. PCR and electrophoresis conditions were as described in methods. Reference is made to FIG. 35 which displays the amplified DNA fragments from each locus and their LSB templates according to their size dependent migration in a single gel lane. Individual fragments are identified by the length (nt) of the expected amplicons from their locus.

Example 36

Amplification and Electrophoresis of Compound Multiplex XIII: Multiplex Subset C6 Loci D13S317 and FGA; and Multiplex Subset D5 Loci Amelogenin, D5S818, D7S820, TPOX and TH01.

Figure 36:
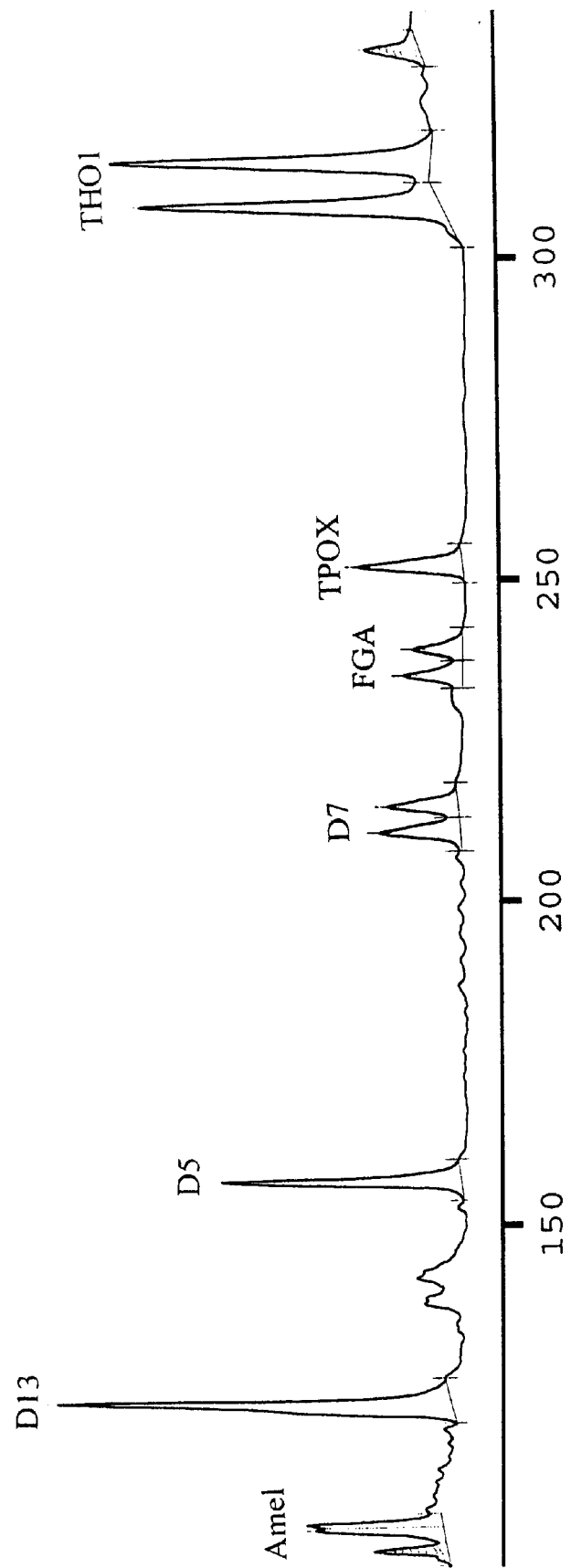
FIG. 36 is a printed image from the ALFexpress automated sequencer (Amersham Pharmacia Biotech) showing the fluorescent detection upon electrophoresis of the PCR product after amplification of the loci from Compound Multiplex XIII, subsets C6+D5: D13S317, FGA", amelogenin, D5S818', D7S820, TPOX', and TH01". Peak areas correspond to fluorescence intensity and are depicted graphically as a function of fragment length (nt). Fluorescent peaks (shaded) measured at 101 and 335 nt represent DNA size standards.

This example demonstrates that subsets C6 and D5 can be co-amplified from genomic DNA by their PCR primers labeled with a common fluorophore (Cy5) and co-electrophoresed in a single gel lane. Alleles were discerned by their relative position and expected amplicon fragment length (Table 1). In this example PCR, electrophoresis conditions and data analysis were carried out as described in methods. Subsets C6 and D5 were co-amplified in a single reaction vessel in total 10 μl reaction volume. The last 25 cycles of PCR were performed at a constant annealing temperature of 57° C. Their PCR amplicons were analyzed in a single electrophoretic gel lane on ALFexpress. The final primer concentrations in this PCR for each locus were: 0.24 μM each of D13S317 [primers 1 [SEQ ID NO: 21] and 2 [SEQ ID NO: 22], 1.5 μM each of FGA primers 1 [SEQ ID NO: 19] and 2 [SEQ ID NO: 40], 0.18 μM each of amelogenin primers 1 [SEQ ID NO: 27] and 2 [SEQ ID NO: 28], 0.21 μM each of D5S818 primers 1 [SEQ ID NO: 15] and 2 [SEQ ID NO: 16], 1.2 μM each of D7S820 primers 1 [SEQ ID NO: 17] and 2 [SEQ ID NO: 18], 0.15 μM each of TPOX primers 1 [SEQ ID NO: 25] and 2 [SEQ ID NO: 26], and 0.9 μM each of TH01 primers 1 [SEQ ID NO: 23] and 2 [SEQ ID NO: 41]. Reference is made to FIG. 36 which displays the amplified DNA fragments from each locus according to their size dependent migration in a single gel lane. Individual fragments are identified by the length (nt) of the expected amplicons from their locus. Together with the A1 and B1 co-amplified loci in Example 17, these loci provide complete CODIS testing for a two color instrument.

Example 37

Figure 37:
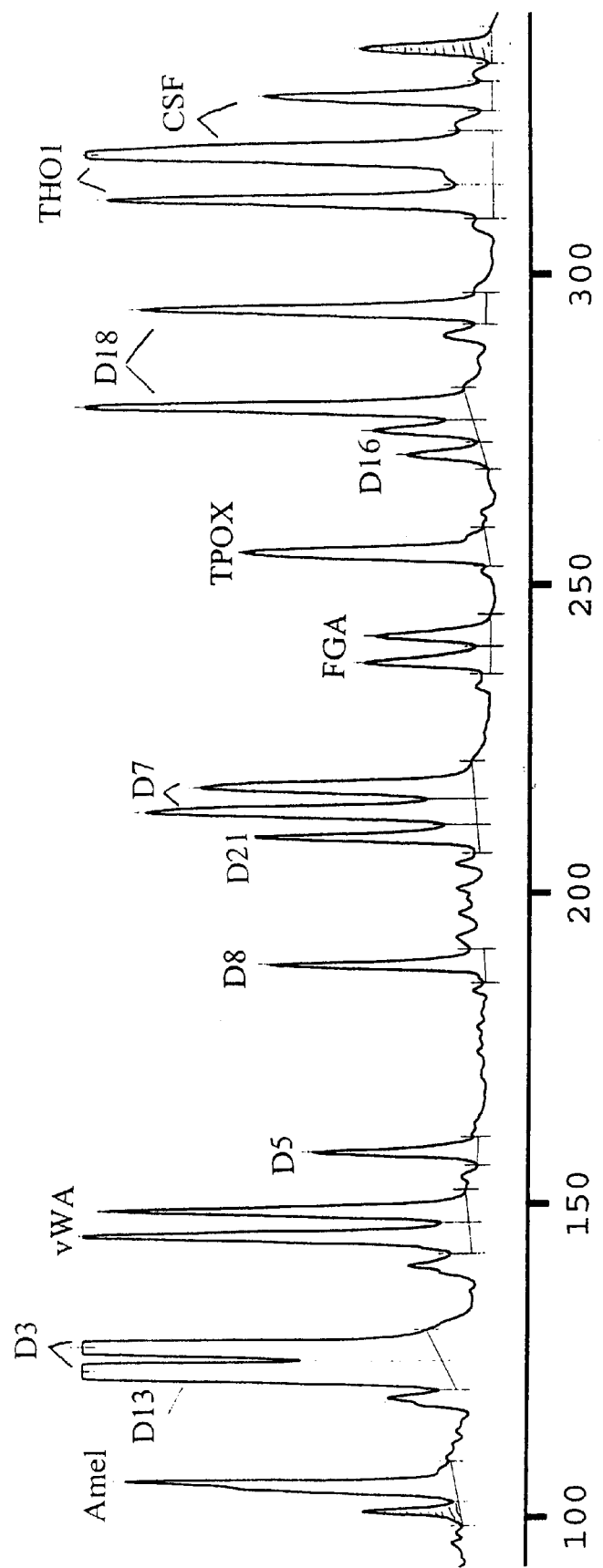
FIG. 37 is a printed image from the ALFexpress automated sequencer (Amersham Pharmacia Biotech) showing the fluorescent detection upon electrophoresis of the PCR product after amplification of the loci from Compound Multiplex XIV, subsets A1+B1+C6+D5: vWA, D21S11, D18S51, D3S1358, D8S1179, D16S539, CSF1PO, D13S317, FGA", D5S818', D7S820, TPOX', TH01" and amelogenin. Peak areas correspond to fluorescence intensity and are depicted graphically as a function of fragment length (nt). Fluorescent peaks (shaded) measured at 101 and 335 nt represent DNA size standards.

Compound Multiplex XIV: Amplification and Electrophoresis of the Amelogenin Locus with the Thirteen CODIS Loci In compound multiplex XIV, amelogenin and CODIS 13 loci were co-amplified including use of the changed FGA reverse primer (in subset C6) and changed TH01 reverse primer (in subset D5). In this example PCR, electrophoretic conditions and data analysis were carried out as described in methods. The last 25 cycles of PCR were performed at a constant annealing temperature of 57° C. The loci from subsets A1, B1, C6, and D5 were constant annealing temperature of 57° C. The loci from subsets A1, B1, C6, and D5 were were analyzed in a single electrophoretic gel lane on ALFexpress. The final primer concentrations in this PCR for each locus were: 0.6 μM each of vWA primers 1 [SEQ ID NO: 1] and 2 [SEQ ID NO: 2], 0.3 μM each of D21S11 primers 1 [SEQ ID NO: 3] and 2 [SEQ ID NO: 4], and 0.12 μM each of D18S51 primers 1 [SEQ ID NO: 5] and 2 [SEQ ID NO: 6], 0.3 μM each of D3S1358 primers 1 [SEQ ID NO: 7] and 2 [SEQ ID NO: 8], 0.45 μM each of D8S1179 primers 1 [SEQ ID NO: 9] and 2 [SEQ ID NO: 10], 0.45 μM each of D16S539 primers 1 [SEQ ID NO: 11] and 2 [SED ID NO: 12], and 0.15 μM each of CSF1PO primers 1 [SEQ ID NO: 13] and 2 [SEQ ID NO: 14], 0.1 μM each of amelogenin primers 1 [SEQ ID NO: 27] and 2 [SEQ ID NO: 28], 0.12 μM each of D5S818 primers 1 [SEQ ID NO: 15] and 2 [SEQ ID NO: 16], 0.75 μM each of FGA primers 1 [SEQ ID NO: 19] and 2 [SEQ ID NO: 40], 0.15 μM each of D13S317 primers 1 [SEQ ID NO: 21] and 2 [SEQ ID NO: 22], 0.75 μM each of D7S820 primers 1 [SEQ ID NO: 17] and 2 [SEQ ID NO: 18], 0.09 μM each of TPOX primers 1 [SEQ ID NO: 25] and 2 [SEQ ID NO: 26], and 0.375 μM each of TH01 primers 1 [SEQ ID NO: 23] and 2 [SEQ ID NO: 41]. The results are shown in FIG. 37. All alleles of the 13 CODIS loci and amelogenin are readily identifiable as peaks of the expected amplicon fragment length corresponding to those found in their multiplex subsets as shown in FIGS. 1, 2, 32, and 33. Peaks representing locus D13S317 and the shorter allele of locus D3S1358 overlapped.

Example 38

Figure 38:
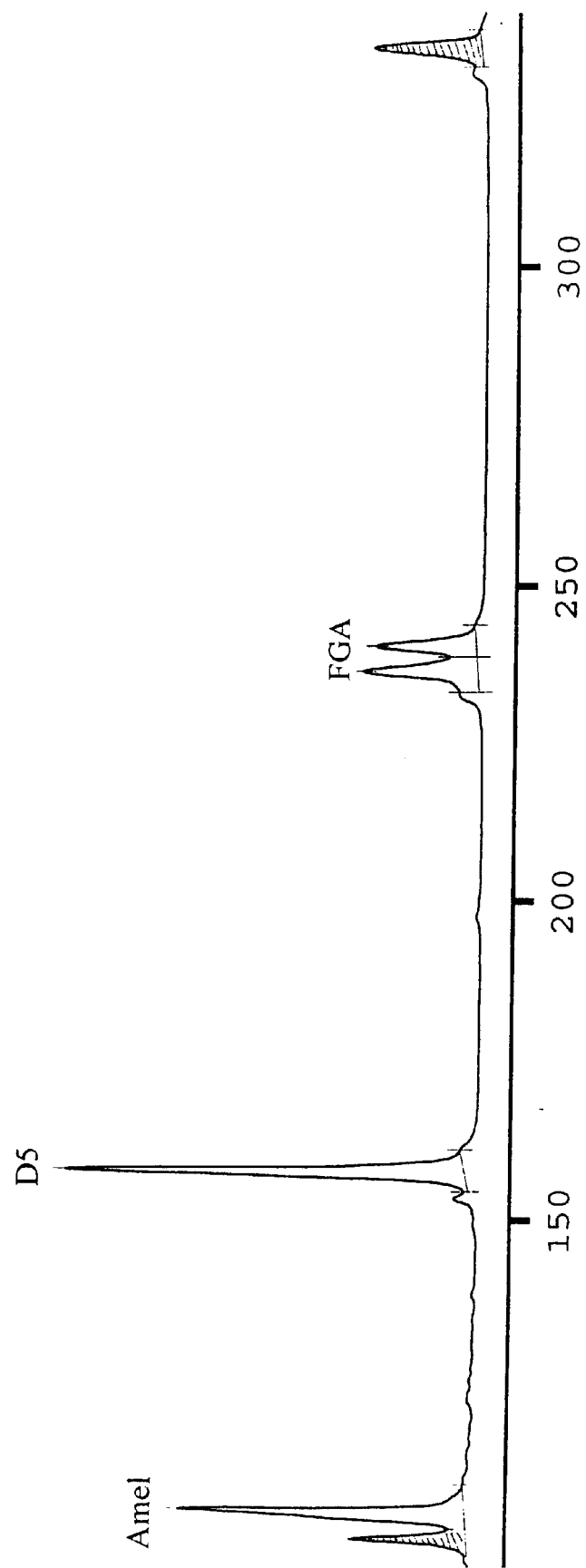
FIG. 38 is a printed image from the ALFexpress automated sequencer (Amersham Pharmacia Biotech) showing the fluorescent detection upon electrophoresis of the PCR product after amplification of the loci from multiplex subset C7: amelogenin, D5S818', and FGA". Peak areas correspond to fluorescence intensity and are depicted graphically as a function of fragment length (nt). Fluorescent peaks (shaded) measured at 101 and 335 nt represent DNA size standards.

Amplification and Electrophoresis of Multiplex Subset C7 Loci Amelogenin, D5S818, and FGA Subset C7 was modified from original subset C2 by removing locus D7S820 to subset D3. In this example, PCR, electrophoresis conditions and data analysis were carried out as described in methods. The last 25 cycles of PCR were performed at a constant annealing temperature of 59° C. The loci in this example were amplified in a single PCR vessel in total 10 μl reaction volume and their PCR amplicons were analyzed in a single electrophoretic gel lane on ALFexpress. The final primer concentrations in this PCR for each locus were: 0.18 μM each of amelogenin primers 1 [SEQ ID NO: 27] and 2 [SEQ ID NO: 28], 0.21 μM each of D5S818 primers 1 [SEQ ID NO: 15] and 2 [SEQ ID NO: 16], and 1.5 μM each of FGA primers 1 [SEQ ID NO: 19] and 2 [SEQ ID NO: 40]. Reference is made to FIG. 38 which displays the amplified DNA fragments from each locus according to their size dependent migration in a single gel lane. Individual fragments are identified by the length (nt) of the expected amplicons from their locus.

Example 39

Amplification and Electrophoresis of Multiplex Subset D6 Loci D13S317, D7S820, TPOX, and TH01

Figure 39:
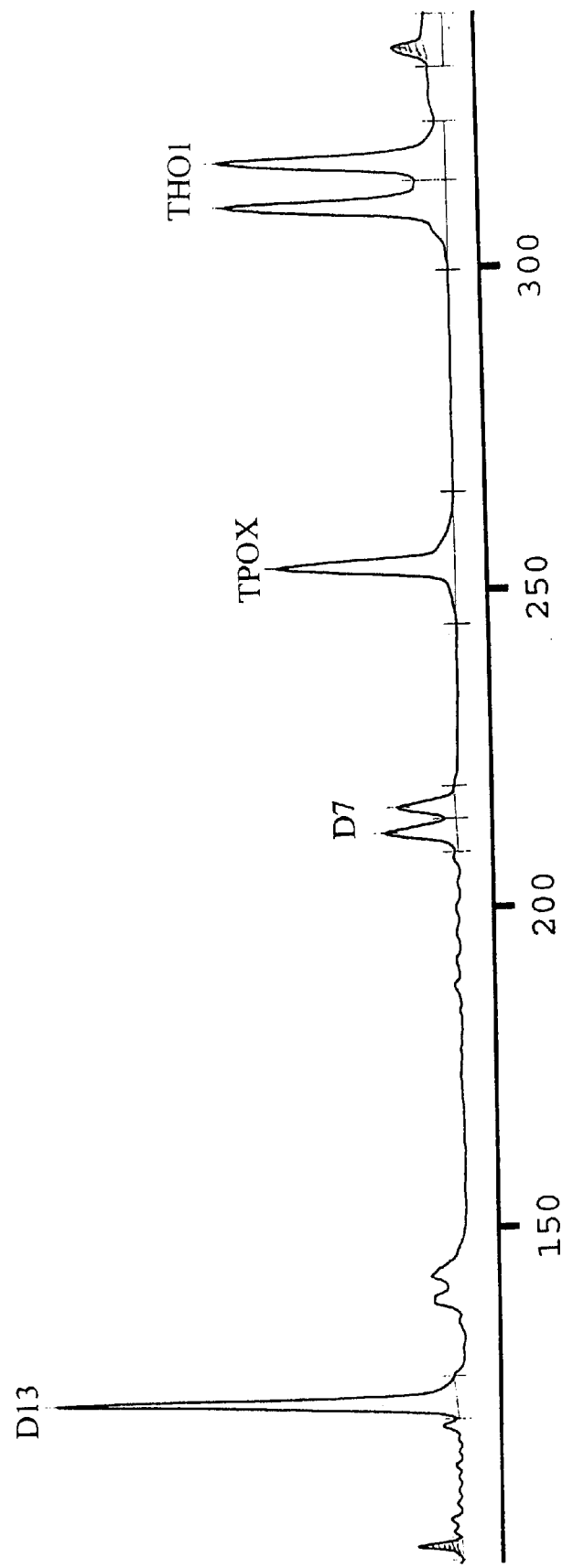
FIG. 39 is a printed image from the ALFexpress automated sequencer (Amersham Pharmacia Biotech) showing the fluorescent detection upon electrophoresis of the PCR product after amplification of the loci from multiplex subset D6: D13S317, D7S820, TPOX', and TH01". Peak areas correspond to fluorescence intensity and are depicted graphically as a function of fragment length (nt). Fluorescent peaks (shaded) measured at 101 and 335 nt represent DNA size standards.

This example is similar to subset D3 except locus D7S820 was inserted into the position of locus TH01 and amplicons of locus TH01 were lengthened to migrate on the right side of locus TPOX by using a new TH01 reverse primer [SEQ ID NO: 41]. In this way, this subset combined with subset C7 allows the use of shorter PCR amplicon from the FGA locus to be employed as in Example 31. In this example, PCR, electrophoretic conditions and data analysis were carried out as described in methods. The last 25 cycles of PCR were performed at a constant annealing temperature of 57° C. The loci in this example were amplified in a single PCR vessel in total 10 ul reaction volume and their PCR amplicons were analyzed in a single electrophoretic gel lane on ALFexpress. The final primer concentrations in this PCR for each locus were: 0.3 µM each of D13S317 primers 1 [SEQ ID NO: 21] and 2 [SEQ ID NO: 22], 1.2 µM each of D7S820 primers 1 [SEQ ID NO: 17] and 2 [SEQ ID NO: 18], and 0.15 µM each of TPOX primers 1 [SEQ ID NO: 25] and 2 [SEQ ID NO: 26], and 0.9 µM each of TH01 primers 1 [SEQ ID NO: 23] and 2 [SEQ ID NO: 41]. Reference is made to FIG. 39 which displays the amplified DNA fragments from each locus according to their size dependent migration in a single gel lane. Individual fragments are identified by the length (nt) of the expected amplicons from their locus.

Example 40
Electrophoresis of Multiplex Subset C7 Loci Amelogenin, D5S818, and FGA, and Their Locus Specific Brackets (LSB)

Figure 40:
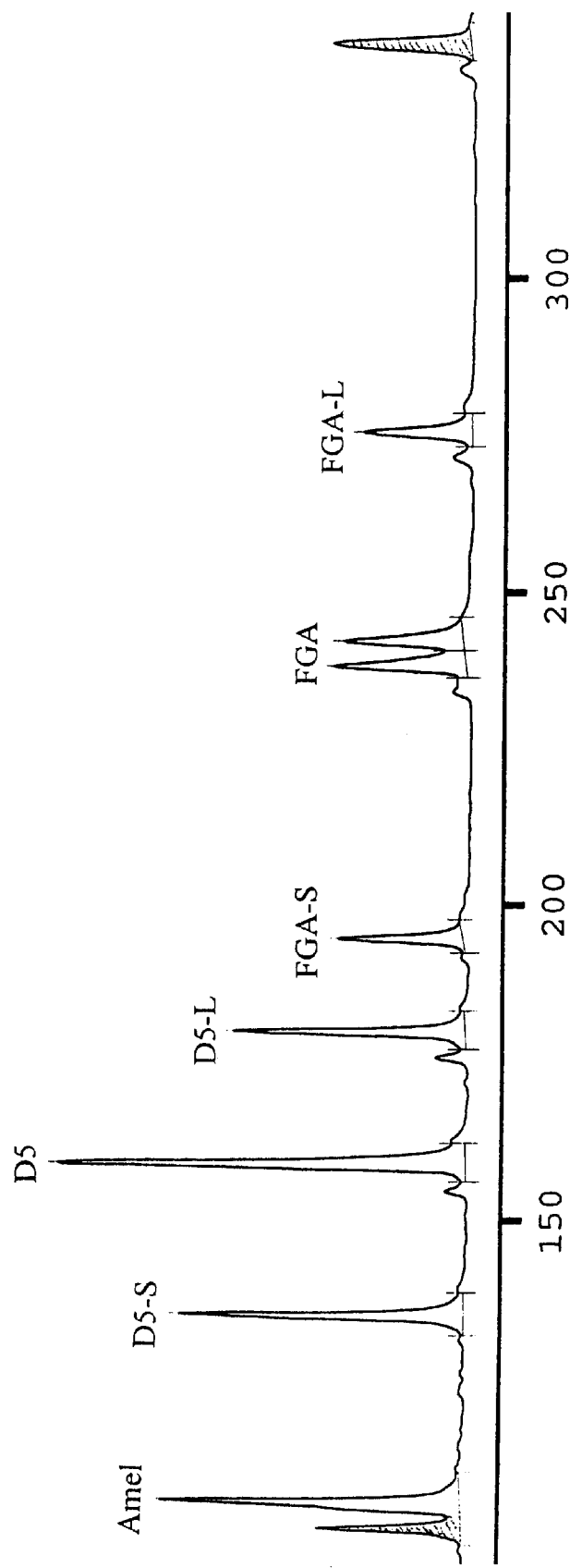
FIG. 40 is a printed image from the ALFexpress automated sequencer (Amersham Pharmacia Biotech) showing the fluorescent detection upon electrophoresis of the PCR product after amplification of the loci from multiplex subset C7: amelogenin, D5S818, FGA", and their Locus Specific Brackets (LSB). D5-S and D5-L: short and long LSBs, respectively, for locus D5S818'; FGA-S and FGA-L: short and long LSBs, respectively, for locus FGA". Peak areas correspond to fluorescence intensity and are depicted graphically as a function of fragment length (nt). Fluorescent peaks (shaded) measured at 101 and 335 nt represent DNA size standards.

Each short and long LSB for the C7 loci was amplified from its locus specific LSB template (Dau et al., U.S. Pat. No. 6,013,444.) in a single PCR vessel by the same primer pair used in subset C7. The number of repeat units contained in each LSB are shown in Table 1. The mixture of individual LSB PCR amplicons from the C7 loci was added into multiplex subset C7 PCR amplicons (same as those in FIG. 38) and co-electrophoresed in a single gel lane on ALFexpress. PCR and electrophoresis conditions were as described in methods. Reference is made to FIG. 40 which displays the amplified DNA fragments from each locus and their LSB templates according to their size dependent migration in a single gel lane. Individual fragments are identified by the length (nt) of the expected amplicons from their locus.

Example 41
Electrophoresis of Multiplex Subset D6 Loci D13S317, D7S820, TPOX, and TH01, and Their Locus Specific Brackets (LSB)

Figure 41:
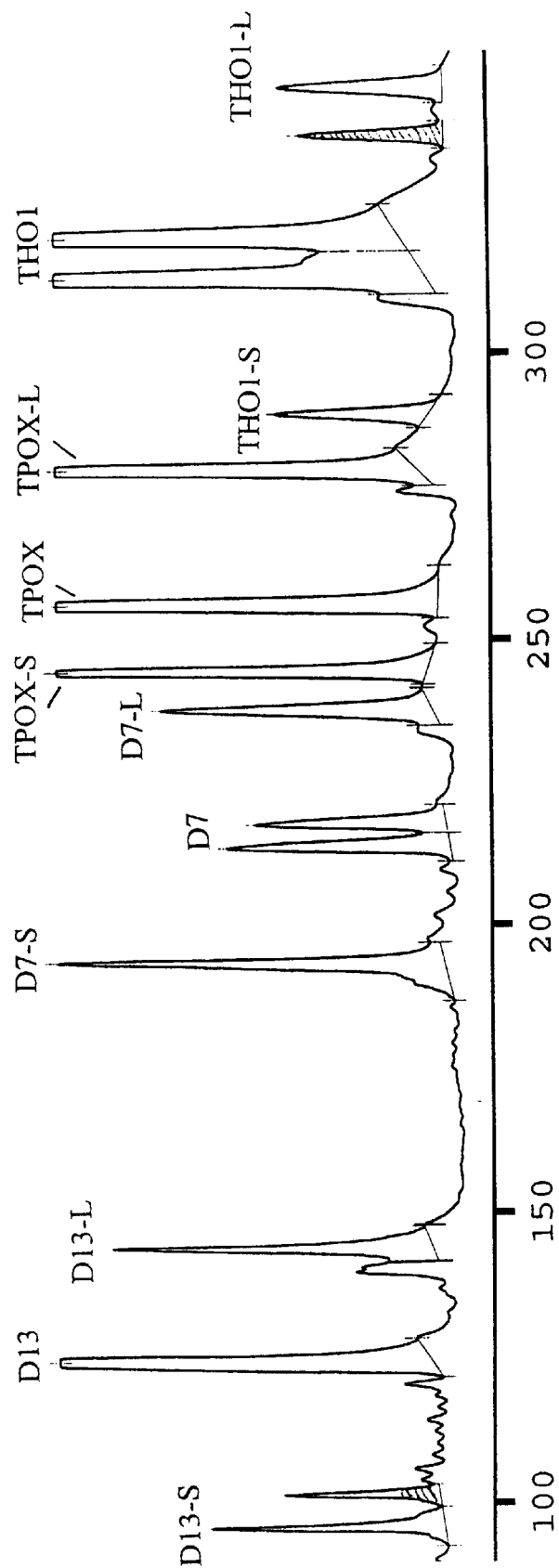
FIG. 41 is a printed image from the ALFexpress automated sequencer (Amersham Pharmacia Biotech) showing the fluorescent detection upon electrophoresis of the PCR product after amplification of the loci from multiplex subset D6: D13S317, D7S820, TPOX, TH01", and their Locus Specific Brackets (LSB). D13-S and D13-L, short and long LSBs, respectively, for locus D13S317; D7-S and D7-L, short and long LSBs, respectively, for locus D7S820; TPOX-S and TPOX-L, short and long LSBs, respectively, for locus TPOX'; TH01-S and TH01-L, short and long LSBs, respectively, for locus TH01". Peak areas correspond to fluorescence intensity and are depicted graphically as a function of fragment length (nt). Fluorescent peaks (shaded) measured at 101 and 335 nt represent DNA size standards.

Each short and long LSB for D6 loci was amplified from its locus specific LSB template (Dau et al., U.S. Pat. No. 6,013,444) by the same primer pair used in subset D6 in a single PCR vessel. The number of repeat units contained in each LSB are shown in Table 1. The mixture of each individual LSB PCR amplicon from D6 loci was added into multiplex subset D6 PCR amplicons (same as those in FIG. 39) and co-electrophoresed in a single gel lane on ALFexpress. PCR and electrophoresis conditions were as described in methods. Reference is made to FIG. 41 which displays the amplified DNA fragments from each locus and their LSB templates according to their size dependent migration in a single gel lane. Individual fragments are identified by the length (nt) of the expected amplicons from their locus.

Example 42
Amplification and Electrophoresis of Compound Multiplex XV: Multiplex Subset C7 Loci Amelogenin, D5S818, and FGA; and Multiplex Subset D6 Loci D13S317, D7S820, TPOX, and TH01

Figure 42:
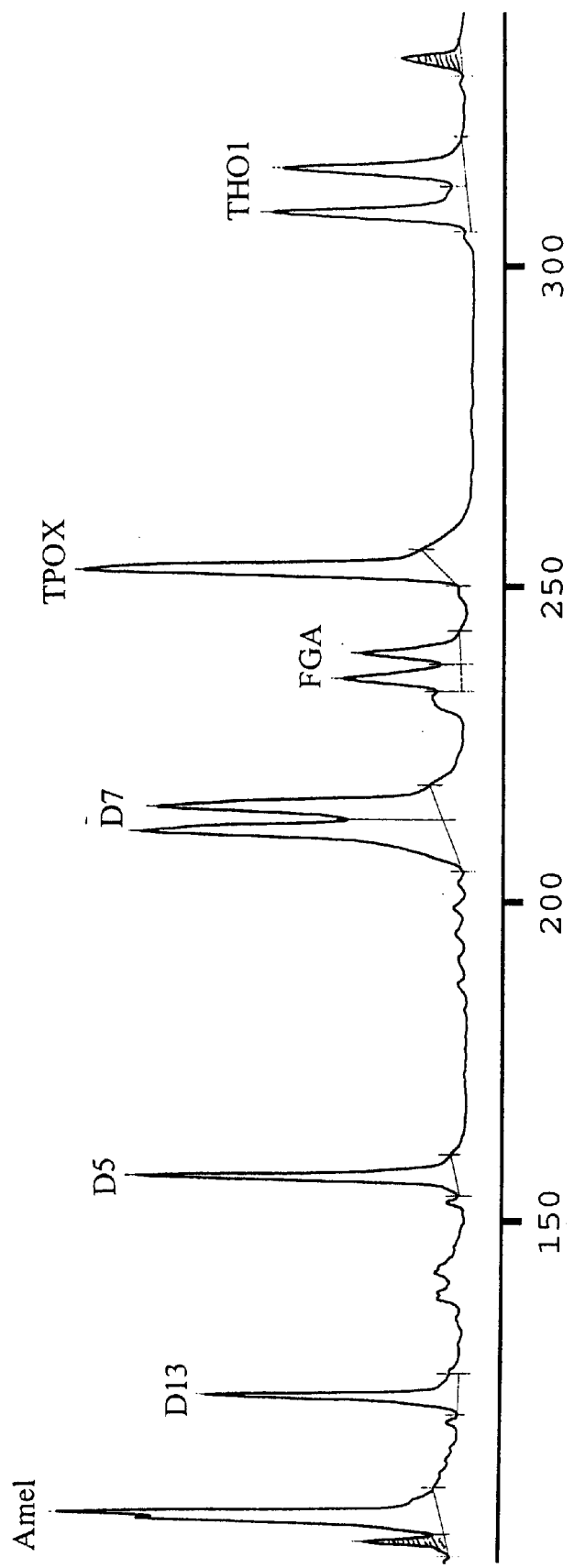
FIG. 42 is a printed image from the ALFexpress automated sequencer (Amersham Pharmacia Biotech) showing the fluorescent detection upon electrophoresis of the PCR product after amplification of the loci from Compound Multiplex XV, subsets C7+D6: amelogenin, D5S818', FGA", D13S317, D7S820, TPOX', and TH01". Peak areas correspond to fluorescence intensity and are depicted graphically as a function of fragment length (nt). Fluorescent peaks (shaded) measured at 101 and 335 nt represent DNA size standards.

This example demonstrates that two subsets C7 and D6 can be co-amplified from genomic DNA by their PCR primers labeled with a common fluorophore (Cy5) and co-electrophoresed in a single gel lane. Alleles were judged by their relative position and expected amplicon fragment length ranges (Table 1). In this example PCR, electrophoresis conditions and data analysis were carried out as described in methods. Subset C7 and D6 were co-amplified in a single reaction vessel in total 10 µl reaction volume. The last 25 cycles of PCR were performed at a constant annealing temperature of 57° C. Their PCR amplicons were analyzed in a single electrophoretic gel lane on ALFexpress. The final primer concentrations in this PCR for each locus were: 0.15 µM each of amelogenin primers 1 [SEQ ID NO: 27] and 2 [SEQ ID NO: 28], 0.15 µM each of D5S818 primers 1 [SEQ ID NO: 15] and 2 [SEQ ID NO: 16], and 2.1 µM each of FGA primers 1 [SEQ ID NO: 19] and 2 [SEQ ID NO: 40], 0.15 µM each of D13S317 primers 1 [SEQ ID NO: 21] and 2 [SEQ ID NO: 22], 2.1 µM each of D7S820 primers 1 [SEQ ID NO: 17] and 2 [SEQ ID NO: 18], and 0.15 µM each of TPOX primers 1 [SEQ ID NO: 25] and 2 [SEQ ID NO: 26], and 1.725 µM each of TH01 primers 1 [SEQ ID NO: 23] and 2 [SEQ ID NO: 41]. Reference is made to FIG. 42 which displays the amplified DNA fragments from each locus according to their size dependent migration in a single gel lane. Individual fragments are identified by the length (nt) of the expected amplicons from their locus. Together with the A1 and B1 co-amplified loci in Example 17, these loci provide complete CODIS testing for a two color instrument.

Figure 43:
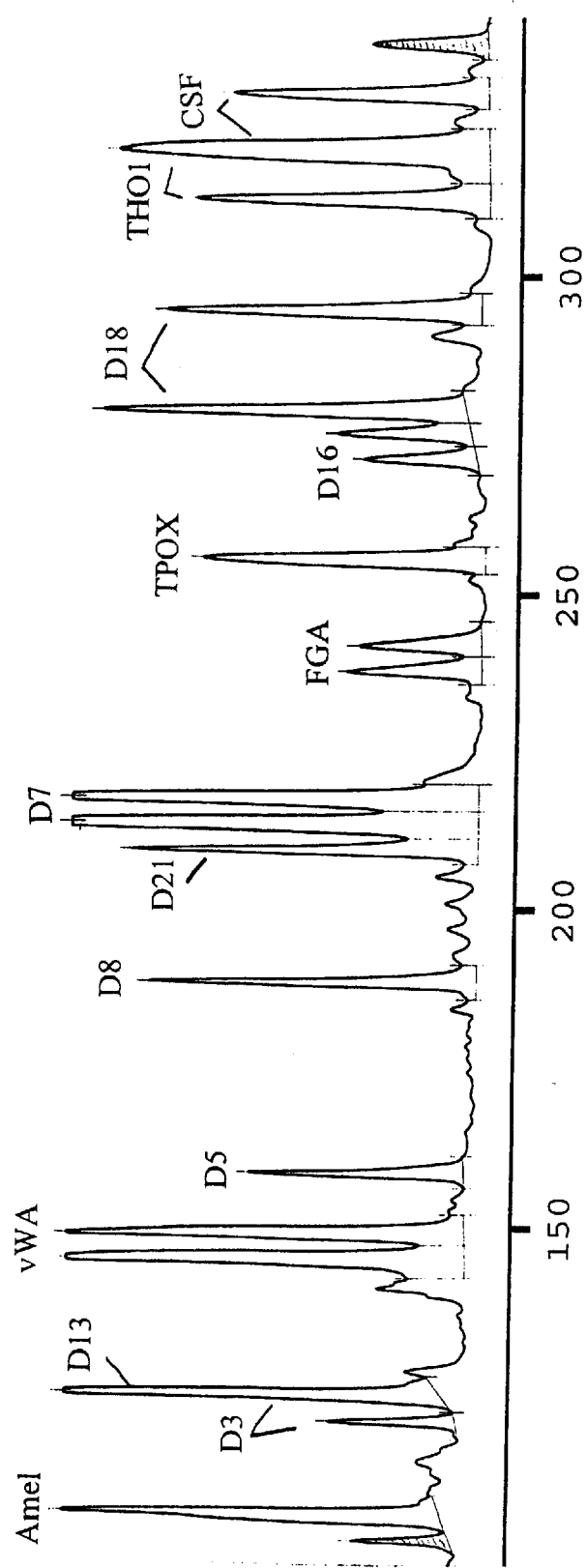
FIG. 43 is a printed image from the ALFexpress automated sequencer (Amersham Pharmacia Biotech) showing the fluorescent detection upon electrophoresis of the PCR product after amplification of the loci from Compound Multiplex XVI, subsets A1+B1+C7+D6: vWA, D21S11, D18S51, D3S1358', D8S1179, D16S539, CSF1PO, D13S317, FGA", amelogenin, D5S818', D7S820, TPOX', and TH01". Peak areas correspond to fluorescence intensity and are depicted graphically as a function of fragment length (nt). Fluorescent peaks (shaded) measured at 101 and 335 nt represent DNA size standards.

Example 43
Compound Multiplex XVI: Amplification and Electrophoresis of Amelogenin Locus with the Thirteen CODIS Loci This example is similar to Example 37 except that different primer pair, primer 1 [SEQ ID NO: 30] and 2 [SEQ ID NO: 31] (Table 3) for locus D3S1358 was used, which produced PCR amplicons from locus D3S1358 3 bp shorter than those shown in FIG. 37. In this example PCR, electrophoretic conditions and data analysis were carried out as described in methods. The last 25 cycles of PCR were performed at a constant annealing temperature of 57° C. Subset loci A1, B1 (3 bp shorter for locus D3S1358), C7, and D6 were amplified in a 57° C. Subset loci A1, B1 (3 bp shorter for locus D3S1358), C7, and D6 were amplified in a single electrophoretic gel lane on ALFexpress. The final primer concentrations in this PCR for each locus were: 0.6 µM each of vWA primers 1 [SEQ ID NO: 1] and 2 [SEQ ID NO: 2], 0.3 µM each of D21S11 primers 1 [SEQ ID NO: 3] and 2 [SEQ ID NO: 4], and 0.12 µM each of D18S51 primers 1 [SEQ ID NO: 5] and 2 [SEQ ID NO: 6], 0.3 µM each of D3S1358 primers 1 [SEQ ID NO: 30] and 2 [SEQ ID NO: 31], 0.45 µM each of D8S1179 primers 1 [SEQ ID NO: 9] and 2 [SEQ ID NO: 10], 0.45 µM each of D16S539 primers 1 [SEQ ID NO: 11] and 2 [SEQ ID NO: 12], and 0.15 µM each of CSF1PO primers 1 [SEQ ID NO: 13] and 2 [SEQ ID NO: 14], 0.1 µM each of amelogenin primers 1 [SEQ ID NO: 27] and 2 [SEQ ID NO: 28], 0.12 µM each of D5S818 primers 1 [SEQ ID NO: 15] and 2 [SEQ ID NO: 16], 0.75 µM each of FGA primers 1 [SEQ ID NO: 19] and 2 [SEQ ID NO: 40], 0.15 µM each of D13S317 primers 1 [SEQ ID NO: 21] and 2 [SEQ ID NO: 22], 0.75 µM each of D7S820 primers 1 [SEQ ID NO: 17] and 2 [SEQ ID NO: 18], 0.09 µM each of TPOX primers 1 [SEQ ID NO: 25] and 2 [SEQ ID NO: 26], and 0.375 µM each of TH01 primers 1 [SEQ ID NO: 23] and 2 [SEQ ID NO: 41]. The results are shown in FIG. 43. All alleles of the 13 CODIS loci and amelogenin are readily identifiable as peaks of the expected amplicon fragment length corresponding to those found in their multiple subsets as shown in FIGS. 1, 2, 38, and 39.

Example 44
DNA Fragment Length Calculation Employing LSB

Fragment sizes can be determined by reference to external and internal calibration standards. In a preferred embodiment, the external standards consist of LSB and two true alleles from each locus. Preferably, the two true alleles from each locus are evenly distributed (equidistant) between their LSB. The internal standards are LSB.

The external standard curves are defined by piece-wise third order polynomials:

$$P(x)=P_0+(P_1 \cdot x)+(P_2 \cdot x^2)+(P_3 \cdot x^3)$$

where x is the run time in minutes.

Alleles of locus D18S51 were amplified in PCR from three genomic DNA samples, NA09947A, NA09948A, and K562, and co-electrophoresed with their LSB brackets on the ABI Prizm 310 as described in Example 29. The external standard curve was generated from the run times and known lengths of two alleles, 15 and 19 from sample NA09947A, and their LSB using Gunplot 3.7© software. Their run times and fragment lengths were:

|           | Time  | Length |
|-----------|-------|--------|
| D18-LSB-S | 19.06 | 252    |
| Allele 15 | 20.02 | 280    |
| Allele 19 | 20.50 | 296    |
| D18-LSB-L | 21.55 | 336    |

The run times of alleles from sample NA09948A and K562 were adjusted by adding an offset value calculated from their LSB run in the same electrophoretic channel to match the external standard curve. For example, the run times of the LSBs and sample alleles in NA0948A in the standard channel were 19.06 (short LSB) and 21.55 (long LSB). The run times of the LSBs in the sample channel were 18.76 (short LSB) and 21.20 (long LSB), and the run times of the sample alleles in the NA0948A sample channel were 19.69 (allele 1) and 20.05 (allele 2). Thus, the run time of the short LSB in the sample channel was 0.3 minutes less that the run time in the standard channel (19.06−18.76=0.3). The run time of the long LSB in the sample channel was 0.35 minutes less than the run time in the standard channel (21.55−21.20=0.35). Therefore, the average run time difference [(0.3+0.35)/2] was 0.325 minutes for the short and long LSB. Therefore, an offset value of 0.325 minutes was added to each sample allele run time. The adjusted run time for allele 1 was then 20.015 (19.69+0.325) and for allele 2 was 20.375 (20.05=0.325).

The adjusted run time for each sample allele was then plotted against the external standard curve to calculate the allele length. The measurement errors were 0.16 and 0.30 nt for allele 15 and 18 of sample NA09948A and 0.32 and 0.28 nt for allele 15 and 16 of sample K562.

Example 45
Sequencing Results from Genomic DNA for Loci D3S1358 and D13S317

In this example, PCR, cloning, sequencing, electrophoresis, and sequence analysis were carried out as described in Methods. This example shows:

1) the unpublished repeat and flanking sequences of locus D3 S1358 (see *1 footnote of Table 1 and SEQ ID #44), and
2) the first correct sequence of locus D 13S317 (see *2 footnote of Table 1 and SEQ ID #45).

Locus D3S1358 was amplified from genomic DNA sample K562 in PCR using a D3S1358 primer pair (SEQ ID NOS. 7 and 8) from Li et al., 1993. A total of 131 nucleotides were sequenced from the D3S1358 amplicon of sample K562, including 16.TAGA repeats as shown on the sequence data sheet. The correct sequence is given in SEQ ID #44.

The sequence given for locus D13S317 in the Gene Bank database is incorrect: only one "AATC" sequence is listed after the repeats, however two AATC sequences are actually present. They are indicated in bold in footnote *2 of Table 1. Locus D13S317 was amplified from genomic DNA samples K562 and NA09947A with PCR using a primer pair (SEQ ID NOS.42 and 43) whose binding sites were designed to lie outside of those hybridized by the primer pair for D13S317 used in STR analysis. A total of 249 nucleotides were sequenced from the D13S317PCRampliconofsample K562, including 8 TATC repeats. Atotal of261 nucleotides were sequenced from the D13S317 PCR amplicon of sample; NA09947A, including 11 TATC repeats. The correct sequence is given in SEQ ID #45.

While the invention has been described in terms of its preferred embodiments, those skilled in the art will recognize that the invention can be practiced with-modification within the spirit and scope of the appended claims. Accordingly, the present invention should not be limited to the embodiments as described above, but should further include all modifications and equivalents thereof within the spirit and scope of the description provided herein.

REFERENCES

Brunmk, C. F. et al. "Assay for Nanogram Quantities of DNA in Cellular Homogenates," *Anal. Biochem.* 92:497–500 (1979).

Carrano, A. V. et al. "A High-Resolution, Fluorescence-Based, Semiautomated Method for DNA Fingerprinting," *Genomics* 4:129–136 (1989).

Connell, C. et al. "Automated DNA Sequence Analysis," *BioTechniques* 5:342–348 (1987).

Dau, P. C. et al. "DNA Bracketing Locus Compatible Standards for Electrophoresis," U.S. Pat. No. 6,013,444.

Demers, D. B. et al. "Multiplex STR Analysis by Capillary Electrophoresis," *Profiles in DNA* 3:3–5 (1998).

Edwards, A. et al. "DNA Typing and Genetic Mapping with Trimeric and Tetrameric Tandem Repeats," *Am. J. Hum. Genet.* 49:746–756 (1991).

Edwards, M. C. et al. "Multiplex PCR: Advantages, Development, and Applications," *PCR Methods and Applications* 3:565–575 (1994).

Frank, R. et al. "DNA chain length markers and the influence of base composition on electrophoretic mobility of oligodeoxyribonucleotides in polyacrylamide gels," *Nucleic Acids Research* 6:2069–2087 (1979).

Fregeau, C. J. et al. "DNA Typing with Fluorescently Tagged Short Tandem Repeats: A Sensitive and Accurate Approach to Human Identification," *BioTechniques* 15:100–119 (1997).

Gill, P. et al. "Forensic Application of DNA 'Fingerprints'," *Nature* 318:577–579 (1985).

Gill, P. et al. "A New Method of STR Interpretation Using Inferential Logic-Development of a Criminal Intelligence Database," *Int. J. Legal Med.* 109:14–22 (1996).

Griffiths, R. A. et al. "New Reference Allelic Ladders to Improve Allelic Designations in a Multiplex STR System," *Int. J. Legal Med* 111:267–272 (1998).

Klimpton, C. P. et al. "Automated DNA Profiling Employing Multiplex Amplification of Short Tandem Repeat Loci," *PCR Methods and Applications* 3:13–22 (1993).

Koreth, J. et al. "Microsatellites and PCR Genomic Analysis," *Journal of Pathology* 178:239–248 (1996).

Lazaruk, K. et al. "Genotyping of Forensic Short Tandem Repeat (STR) Systems Based on Sizing Precision in a Capillary Electrophoresis Instrument," *Electrophoresis* 19:86–93 (1998).

Li, H. etal. "Three Tetranucleotide Polymorphisms for Loci: D3S1352; D3S1358; D3S1359." *Human Molecular Genetics,* 2:1327 (1993)

Miscicka-Sliwka, D. et al. "Optimization of a Hexaplex DNA Amplification from Short Tandem Repeat and Amelogenin Loci," *Electrophoresis* 18:1627–1632 (1997).

Oldroyd, N. J. et al. "A Highly Discriminating Octoplex Short Tandem Repeat Polymerase Chain Reaction System Suitable for Human Individual Identification," *Electrophoresis* 16:334–337 (1995).

Orti, G. et al. "Phylogenetic Assessment of Length Variation at a Microsatellite Locus," *Proc. Nat. Acad. Sci. USA* 94:10745–10749 (1997).

Patel, P. I., et al. "Organization of the HPRT Gene and Related Sequences in the Human Genome," *Somat. Cell Mol. Genet* 10:483–493 (1984).

Perez-Lezaun, A. et al. "Allele Frequencies for 20 Microsatellites in a Worldwide Population Survey," *Human Heredity* 47:189–296 (1997).

Powell, W., et al. "Polymorphism Revealed by Single Repeat Sequences, *Trends Plant Sci.* 1:215–222 (1996).

Puers, C. et al. *Science* 272:1755–1762 (1993).

Robertson, J. M. et al. "Forensic Applications of a Rapid, Sensitive, and Precise Multiplex Analysis of the Four Short Tandem Repeat Loci HUMVWF3 I/A, HUMTH01, HUMF 13A1, and HUMFES/FPS," *Electrophoresis* 16:1568–1576 (1995).

Saiki, R. K., et al. "Enzymatic Amplification of beta-Globin Genomic Sequences and Restriction Site Analysis for Diagnosis of Sickle Cell Anemia," *Science* 230:1350–1354 (1985).

Schumm, J. W. et al. "Why Use a Size Marker and Allelic Ladders in STR Analysis?," *Profiles in DNA* 1:11–13 (1997).

Schumm, J. W. et al. "The GenePrint® PowerPlex™ 2.1 System for the FBI Selection of Thirteen CODIS Core STR Loci and the Seven Standard STR Loci for ENFSI," *Profiles in DNA* 3:3–7 (1999).

Simons, et al. U.S. Pat. No. 5,192,659.

Sullivan, K. et al. "Automated DNA Profiling by Fluorescent Labeling of PCR Products," *PCR Methods and Applications* 2:34–40 (1992).

Sullivan, K. et al. "A Rapid and Quantitative DNA Sex Test: Fluorescence-Based PCR Analysis of X-Y Homologous Gene Amelogenin," *Biotechniques* 15:636–638 (1993).

Walsh, P. S. et al. "Preferential PCR Amplification of Alleles: Mechanisms and Solutions," *PCR Methods and Applications* 1:241–250 (1992).

Waye, J. S., et al. "Sensitive and Specific Quantitation of Human Genomic Deoxyribounucleic Acid (DNA) in Forensic Science Specimens: Casework Examples," *J. Forensic Sci.* 36:1198–1203 (1991).

Ziegle, J. S. et al. "Application of Automated DNA Sizing Technology for Genotyping Microsatellite Loci," *Genomics* 14:1026–1031 (1992).

We claim:

1. A method of determining fragment lengths of alleles present at a plurality of loci in a DNA-containing sample, comprising the steps of:
   a) obtaining a DNA-containing sample to be analyzed;
   b) amplifying by compound multiplex PCR a plurality of loci comprising FGA, vWA, TH01, TPOX, CSF1PO, D3S1358, D5S818, D7S820, D8S1179, D13S317, D16S539, D18S51, and D21S11, wherein said compound multiplex PCR is carried out using a plurality of primer pairs each of which is specific for one of said loci and wherein said step of amplifying produces a mixture of labeled amplicons, and
   c) analyzing by electrophoresis said mixture of labeled amplicons, wherein said step of analyzing allows the determination of said fragment lengths of alleles present at said plurality of loci in said DNA-containing sample, and wherein said plurality of primer pairs comprises at least 13 primer pairs, and said plurality of primer pairs and the locus each primer pair amplifies are selected from the group consisting of:
   a) SEQ ID 1 and SEQ ID 2 for locus vWA;
   b) SEQ ID 3 and SEQ ID 4 for locus D21S11;
   c) SEQ ID 5 and SEQ ID 6 for locus D18S51;
   d) SEQ ID 7 and SEQ ID 8 for locus D31358;
   e) SEQ ID 9 and SEQ ID 10 for locus D8S1179;
   f) SEQ ID 11 and SEQ ID 12 for locus D16S539;
   g) SEQ ID 13 and SEQ ID 14 for locus CSF1PO;
   h) SEQ ID 15 and SEQ ID 16 for locus D5S818;
   i) SEQ ID 17 and SEQ ID 18 for locus D7S820;
   j) SEQ ID 19 and SEQ ID 20 for locus FGA;
   k) SEQ ID 21 and SEQ ID 22 for locus D13S317;
   l) SEQ ID 23 and SEQ ID 24 for locus TH01;
   m) SEQ ID 25 and SEQ ID 26 for locus TPOX;
   n) SEQ ID 27 and SEQ ID 28 for Amelogenin;
   o) SEQ ID 3 and SEQ ID 29 for locus D212S11;
   p) SEQ ID 32 and SEQ ID 33 for locus FGA;
   q) SEQ ID 15 and SEQ ID 34 for locus D5S818;
   r) SEQ ID 23 and SEQ ID 35 for locus TH01;
   s) SEQ ID 36 and SEQ ID 4 for locus D21S11;
   t) SEQ ID 5 and SEQ ID 37 for locus D18S51;
   u) SEQ ID 30 and SEQ ID 8 for locus D3S1358;
   v) SEQ ID 25 and SEQ ID 38 for locus TPOX;
   w) SEQ ID 5 and SEQ ID 39 for locus D18S51;
   x) SEQ ID 19 and SEQ ID 40 for locus FGA;
   y) SEQ ID 23 and SEQ ID 41 for locus TH01; and
   z) SEQ ID 42 and SEQ ID 43 for locus D13S31.

2. A method of determining fragment lengths of alleles present at a plurality of loci in a DNA-containing sample, comprising the steps of:
   a) obtaining a DNA-containing sample to be analyzed;
   b) amplifying by compound multiplex PCR a plurality of loci comprising FGA, vWA, TH01, TPOX, CSF1PO, D3S1358, D5S818, D7S820, D8S1179, D13S317, D16S539, D18S51, and D21S11, wherein said compound multiplex PCR is carried out using a plurality of primer pairs each of which is specific for one of said loci and wherein said step of amplifying produces a mixture of labeled amplicons, and
   c) analyzing by electrophoresis said mixture of labeled amplicons, wherein said step of analyzing allows the determination of said fragment lengths of alleles present at said plurality of loci in said DNA-containing sample, and wherein said plurality of primer pairs is
   SEQ ID #1 and SEQ ID #2;
   SEQ ID #3 and SEQ ID #4;
   SEQ ID #5 and SEQ ID #6;
   SEQ ID #7 and SEQ ID #8;
   SEQ ID #9 and SEQ ID #10;
   SEQ ID #11 and SEQ ID #12;
   SEQ ID #13 and SEQ ID #14;
   SEQ ID #15 and SEQ ID #16;
   SEQ ID #17 and SEQ ID #18;
   SEQ ID #19 and SEQ ID #20;
   SEQ ID #21 and SEQ ID #22;
   SEQ ID #23 and SEQ ID #24; and
   SEQ ID #25 and SEQ ID #26.

3. A method of determining fragment lengths of alleles present at a plurality of loci in a DNA-containing sample, comprising the steps of:
   a) obtaining a DNA-containing sample to be analyzed;
   b) amplifying by compound multiplex PCR a plurality of loci comprising FGA, vWA, TH01, TPOX, CSF1PO, D3S1358, D5S818, D7S820,D8S1179, D13S317, D16S539, D18S51, and D21S11, wherein said compound multiplex PCR is carried out using a plurality of primer pairs each of which is specific for one of said loci and wherein said step of amplifying produces a mixture of labeled amplicons, and
   c) analyzing by electrophoresis said mixture of labeled amplicons, wherein said step of analyzing allows the determination of said fragment lengths of alleles present at said plurality of loci in said DNA-containing sample, and wherein said plurality of primer pairs is
   SEQ ID #1 and SEQ ID #2;
   SEQ ID #3 and SEQ ID #4;
   SEQ ID #5 and SEQ ID #6;
   SEQ ID #7 and SEQ ID #8;
   SEQ ID #9 and SEQ ID #10;
   SEQ ID #11 and SEQ ID #12;
   SEQ ID #13 and SEQ ID #14;
   SEQ ID #27 and SEQ ID #28;
   SEQ ID #15 and SEQ ID #16;
   SEQ ID #17 and SEQ ID #18;
   SEQ ID #19 and SEQ ID #20;
   SEQ ID #21 and SEQ ID #22;
   SEQ ID #23 and SEQ ID #24; and
   SEQ ID #25 and SEQ ID #26.

4. A method of determining fragment lengths of alleles present at a plurality of loci in a DNA-containing sample, comprising the steps of:
   a) obtaining a DNA-containing sample to be analyzed;
   b) amplifying by compound multiplex PCR a plurality of loci comprising FGA, vWA, TH01, TPOX, CSF1PO, D3S1358, D5S818, D7S820, D8S1179, D13S317, D16S539, D18S51, and D21S11, wherein said compound multiplex PCR is carried out using a plurality of primer pairs each of which is specific for one of said loci and wherein said step of amplifying produces a mixture of labeled amplicons, and
   c) analyzing by electrophoresis said mixture of labeled amplicons, wherein said step of analyzing allows the determination of said fragment lengths of alleles present at said plurality of loci in said DNA-containing sample, and wherein said plurality of primer pairs is
   SEQ ID #1 and SEQ ID #2;
   SEQ ID #3 and SEQ ID #29;
   SEQ ID #5 and SEQ ID #6;
   SEQ ID #30 and SEQ ID #31;
   SEQ ID #9 and SEQ ID #10;
   SEQ ID #32 and SEQ ID #33;
   SEQ ID #21 and SEQ ID #22;
   SEQ ID #15 and SEQ ID #34;
   SEQ ID #17 and SEQ ID #18;
   SEQ ID #11 and SEQ ID #12;
   SEQ ID #1 and SEQ ID #2;
   SEQ ID #23 and SEQ ID #35;
   SEQ ID #25 and SEQ ID #26; and
   SEQ ID #13 and SEQ ID #14.

5. A method of determining fragment lengths of alleles present at a plurality of loci in a DNA-containing sample, comprising the steps of:
   a) obtaining a DNA-containing sample to be analyzed;
   b) amplifying by compound multiplex PCR a plurality of loci comprising FGA, vWA, TH01, TPOX, CSF1PO, D3S1358, D5S818, D7S820, D8S1179, D13S317, D16S539, D18S551, and D21S11, wherein said compound multiplex PCR is carried out using a plurality of primer pairs each of which is specific for one of said loci and wherein said step of amplifying produces a mixture of labeled amplicons, and
   c) analyzing by electrophoresis said mixture of labeled, amplicons, wherein said step of analyzing allows the determination of said fragment lengths of alleles present at said plurality of loci in said DNA-containing sample, and wherein said plurality of primer pairs is
   SEQ ID #1 and SEQ ID #2;
   SEQ ID #36 and SEQ ID #4;
   SEQ ID #5 and SEQ ID #37;
   SEQ ID #30 and SEQ ID #8;
   SEQ ID #9 and SEQ ID #10;
   SEQ ID #15 and SEQ ID #16;
   SEQ ID #13 and SEQ ID #14;
   SEQ ID #15 and SEQ ID #34;
   SEQ ID #17 and SEQ ID #18;
   SEQ ID #19 and SEQ ID #20;
   SEQ ID #21 and SEQ ID #22;
   SEQ ID #23 and SEQ ID #24; and
   SEQ ID #25 and SEQ ID #38.

6. A method of determining fragment lengths of alleles present at a plurality of loci in a DNA-containing sample, comprising the steps of:
   a) obtaining a DNA-containing sample to be analyzed;
   b) amplifying by compound multiplex PCR a plurality of loci comprising FGA, vWA, TH01, TPOX, CSF1PO, D3S1358, D5S818, D7S820, D8S1179, D13S317, D16S539, D18S51, and D21S11, wherein said compound multiplex PCR is carried out using a plurality of primer pairs each of which is specific for one of said loci and wherein said step of amplifying produces a mixture of labeled amplicons, and
   c) analyzing by electrophoresis said mixture of labeled amplicons, wherein said step of analyzing allows the determination of said fragment lengths of alleles present at said plurality of loci in said DNA-containing sample, and wherein said plurality of primer pairs is
   SEQ ID #1 and SEQ ID #2;
   SEQ ID #36 and SEQ ID #4;
   SEQ ID #5 and SEQ ID #37;
   SEQ ID #30 and SEQ ID #8;
   SEQ ID #9 and SEQ ID #10;
   SEQ ID #15 and SEQ ID #16;
   SEQ ID #13 and SEQ ID #14;
   SEQ ID #27 and SEQ ID #28;
   SEQ ID #15 and SEQ ID #34;
   SEQ ID #17 and SEQ ID #18;
   SEQ ID #19 and SEQ ID #20;
   SEQ ID #21 and SEQ ID #22;
   SEQ ID #23 and SEQ ID #24; and
   SEQ ID #25 and SEQ ID #38.

7. A method of determining fragment lengths of alleles present at a plurality of loci in a DNA-containing sample, comprising the steps of:
   a) obtaining a DNA-containing sample to be analyzed;
   b) amplifying by compound multiplex PCR a plurality of loci comprising FGA, vWA, TH01, TPOX, CSF1PO, D3S1358, D5S818, D7S820, D8S1179, D13S317, D16S539, D18S51, and D21 S11, wherein said compound multiplex PCR is carried out using a plurality of primer pairs each of which is specific for one of said loci and wherein said step of amplifying produces a mixture of labeled amplicons, and
   c) analyzing by electrophoresis said mixture of labeled amplicons, wherein said step of analyzing allows the determination of said fragment lengths of alleles present at said plurality of loci in said DNA-containing sample, and wherein said plurality of primer pairs is
   SEQ ID #1 and SEQ ID #2;
   SEQ ID #3 and SEQ ID #4;
   SEQ ID #5 and SEQ ID #39;
   SEQ ID #7 and SEQ ID #8;
   SEQ ID #9 and SEQ ID #10;
   SEQ ID #11 and SEQ ID #12;
   SEQ ID #13 and SEQ ID #14;
   SEQ ID #27 and SEQ ID #28;
   SEQ ID #15 and SEQ ID #16;
   SEQ ID #17 and SEQ ID #18;
   SEQ ID #19 and SEQ ID #20;
   SEQ ID #21 and SEQ ID #22;
   SEQ ID #23 and SEQ ID #24; and
   SEQ ID #25 and SEQ ID #38.

8. A method of determining fragment lengths of alleles present at a plurality of loci in a DNA-containing sample, comprising the steps of:
   a) obtaining a DNA-containing sample to be analyzed;
   b) amplifying by compound multiplex PCR a plurality of loci comprising FGA, vWA, TH01, TPOX, CSF1PO, D3S1358, D5S818, D7S820, D8S1179, D13S317, D16S539, D18S51, and D21S11, wherein said compound multiplex PCR is carried out using a plurality of primer pairs each of which is specific for one of said loci and wherein said step of amplifying produces a mixture of labeled amplicons, and c) analyzing by electrophoresis said mixture of labeled amplicons, wherein said step of analyzing allows the determination of said fragment lengths of alleles present at said plurality of loci in said DNA-containing sample, and wherein said plurality of primer pairs is
SEQ ID #1 and SEQ ID #2;
SEQ ID #3 and SEQ ID #4;
SEQ ID #5 and SEQ ID #6;
SEQ ID #7 and SEQ ID #8;
SEQ ID #9 and SEQ ID #10;
SEQ ID #11 and SEQ ID #12; and
SEQ ID #13 and SEQ ID #14.

9. A method of determining fragment lengths of alleles present at a plurality of loci in a DNA-containing sample, comprising the steps of:

a) obtaining a DNA-containing sample to be analyzed;

b) amplifying by compound multiplex PCR a plurality of loci comprising FGA, vWA, TH01, TPOX, CSF1PO, D3S1358, D5S818, D7S820, D8S1179, D13S317, D16S539, D18S51, and D21S11, wherein said compound multiplex PCR is carried out using a plurality of primer pairs each of which is specific for one of said loci and wherein said step of amplifying produces a mixture of labeled amplicons, and c) analyzing by electrophoresis said mixture of labeled amplicons, wherein said step of analyzing allows the determination of said fragment lengths of alleles present at said plurality of loci in said DNA-containing sample, and wherein said plurality of primer pairs is
SEQ ID #15 and SEQ ID #16;
SEQ ID #17 and SEQ ID #18;
SEQ ID #19 and SEQ ID #20;
SEQ ID #21 and SEQ ID #22;
SEQ ID #23 and SEQ ID #24; and
SEQ ID #25 and SEQ ID #26.

10. A method of determining fragment lengths of alleles present at a plurality of loci in a DNA-containing sample, comprising the steps of:

a) obtaining a DNA-containing sample to be analyzed;

b) amplifying by compound multiplex PCR a plurality of loci comprising FGA, vWA, TH01, TPOX, CSF1PO, D3S1358, D5S818, D7S820, D8S1179, D13S317, D16S539, D18S51, and D21S11, wherein said compound multiplex PCR is carried out using a plurality of primer pairs each of which is specific for one of said loci and wherein said step of amplifying produces a mixture of labeled amplicons, and c) analyzing by electrophoresis said mixture of labeled amplicons, wherein said step of analyzing allows the determination of said fragment lengths of alleles present at said plurality of loci in said DNA-containing sample, and wherein said plurality of primer pairs is
SEQ ID #27 and SEQ ID #28;
SEQ ID #15 and SEQ ID #16;
SEQ ID #17 and SEQ ID #18;
SEQ ID #19 and SEQ ID #20;
SEQ ID #21 and SEQ ID #22;
SEQ ID #23 and SEQ ID #24;
SEQ ID #25 and SEQ ID #38; and
SEQ ID #13 and SEQ ID #14.

11. A method of determining fragment lengths of alleles present at a plurality of loci in a DNA-containing sample, comprising the steps of:

a) obtaining a DNA-containing sample to be analyzed;

b) amplifying by compound multiplex PCR a plurality of loci comprising FGA, vWA, TH01, TPOX, CSF1PO, D3S1358, D5S818, D7S820, D8S1179, D13S317, D16S539, D18S51, and D21S11, wherein said compound multiplex PCR is carried out using a plurality of primer pairs each of which is specific for one of said loci and wherein said step of amplifying produces a mixture of labeled amplicons, and c) analyzing by electrophoresis said mixture of labeled amplicons, wherein said step of analyzing allows the determination of said fragment lengths of alleles present at said plurality of loci in said DNA-containing sample, and wherein said plurality of primer pairs is
SEQ ID #1 and SEQ ID #2;
SEQ ID #3 and SEQ ID #4;
SEQ ID #5 and SEQ ID #6;
SEQ ID #27 and SEQ ID #28;
SEQ ID #15 and SEQ ID #16;
SEQ ID #17 and SEQ ID #18; and
SEQ ID #19 and SEQ ID #20.

12. A method of determining fragment lengths of alleles present at a plurality of loci in a DNA-containing sample, comprising the steps of:

a) obtaining a DNA-containing sample to be analyzed;

b) amplifying by compound multiplex PCR a plurality of loci comprising FGA, vWA, TH01, TPOX, CSF1PO, D3S1358, D5S818, D7S820, D8S1179, D13S317, D16S539, D18S51, and D21S11, wherein said compound multiplex PCR is carried out using a plurality of primer pairs each of which is specific for one of said loci and wherein said step of amplifying produces a mixture of labeled amplicons, and c) analyzing by electrophoresis said mixture of labeled amplicons, wherein said step of analyzing allows the determination of said fragment lengths of alleles present at said plurality of loci in said DNA-containing sample, and wherein said plurality of primer pairs is
SEQ ID #7 and SEQ ID #8;
SEQ ID #9 and SEQ ID #10;
SEQ ID #11 and SEQ ID #12;
SEQ ID #13 and SEQ ID #14;
SEQ ID #21 and SEQ ID #22;
SEQ ID #23 and SEQ ID #24;
SEQ ID #25 and SEQ ID #26.

13. A method of determining fragment lengths of alleles present at a plurality of loci in a DNA-containing sample, comprising the steps of:

a) obtaining a DNA-containing sample to be analyzed;

b) amplifying by compound multiplex PCR a plurality of loci comprising FGA, vWA, TH01, TPOX, CSF1PO, D3S1358, D5S818, D7S820, D8S1179, D13S317, D16S539, D18S51, and D21S11, wherein said compound multiplex PCR is carried out using a plurality of primer pairs each of which is specific for one of said loci and wherein said step of amplifying produces a mixture of labeled amplicons, and c) analyzing by electrophoresis said mixture of labeled amplicons, wherein said step of analyzing allows the determination of said fragment lengths of alleles present at said plurality of loci in said DNA-containing sample, and wherein said plurality of primer pairs is
SEQ ID #7 and SEQ ID #8;
SEQ ID #9 and SEQ ID #10;
SEQ ID #11 and SEQ ID #12;
SEQ ID #13 and SEQ ID #14
SEQ ID #27 and SEQ ID #28;

SEQ ID #15 and SEQ ID #16;
SEQ ID #17 and SEQ ID #18; and
SEQ ID #19 and SEQ ID #20.

14. A method of determining fragment lengths of alleles present at a plurality of loci in a DNA-containing sample, comprising the steps of:
   a) obtaining a DNA-containing sample to be analyzed;
   b) amplifying by compound multiplex PCR a plurality of loci comprising FGA, vWA, TH01, TPOX, CSF1PO, D3S1358, D5S818, D7S820, D8S1179, D13S317, D16S539, D18S51, and D21S11, wherein said compound multiplex PCR is carried out using a plurality of primer pairs each of which is specific for one of said loci and wherein said step of amplifying produces a mixture of labeled amplicons, and
   c) analyzing by electrophoresis said mixture of labeled amplicons, wherein said step of analyzing allows the determination of said fragment lengths of alleles present at said plurality of loci in said DNA-containing sample, and wherein said plurality of primer pairs is
   SEQ ID #21 and SEQ ID #22;
   SEQ ID #19 and SEQ ID #40;
   SEQ ID #27 and SEQ ID #28;
   SEQ ID #15 and SEQ ID #34;
   SEQ ID #17 and SEQ ID #18;
   SEQ ID #25 and SEQ ID #38; and
   SEQ ID #23 and SEQ ID #41.

15. A method of determining fragment lengths of alleles present at a plurality of loci in a DNA-containing sample, comprising the steps of:
   a) obtaining a DNA-containing sample to be analyzed;
   b) amplifying by compound multiplex PCR a plurality of loci comprising FGA, vWA, TH01, TPOX, CSF1PO, D3S1358, D5S818, D7S820, D8S1179, D13S317, D16S539, D18S51, and D21S11, wherein said compound multiplex PCR is carried out using a plurality of primer pairs each of which is specific for one of said loci and wherein said step of amplifying produces a mixture of labeled amplicons, and
   c) analyzing by electrophoresis said mixture of labeled amplicons, wherein said step of analyzing allows the determination of said fragment lengths of alleles present at said plurality of loci in said DNA-containing sample, and wherein said plurality of primer pairs is
   SEQ ID #1 and SEQ ID #2;
   SEQ ID #3 and SEQ ID #4;
   SEQ ID #5 and SEQ ID #6;
   SEQ ID #7 and SEQ ID #8;
   SEQ ID #9 and SEQ ID #10;
   SEQ ID #11 and SEQ ID #12;
   SEQ ID #13 and SEQ ID #14;
   SEQ ID #21 and SEQ ID #22;
   SEQ ID #19 and SEQ ID #40;
   SEQ ID #27 and SEQ ID #28;
   SEQ ID #15 and SEQ ID #34;
   SEQ ID #17 and SEQ ID #18;
   SEQ ID #25 and SEQ ID #38; and
   SEQ ID #23 and SEQ ID #41.

16. A method of determining fragment lengths of alleles present at a plurality of loci in a DNA-containing sample, comprising the steps of:
   a) obtaining a DNA-containing sample to be analyzed;
   b) amplifying by compound multiplex PCR a plurality of loci comprising FGA, vWA, TH01, TPOX, CSF1PO, D3S1358, D5S818, D7S820, D8S1179, D13S317, D16S539, D18S51, and D21S11, wherein said compound multiplex PCR is carried out using a plurality of primer pairs each of which is specific for one of said loci and wherein said step of amplifying produces a mixture of labeled amplicons, and
   c) analyzing by electrophoresis said mixture of labeled amplicons, wherein said step of analyzing allows the determination of said fragment lengths of alleles present at said plurality of loci in said DNA-containing sample, and wherein said plurality of primer pairs is
   SEQ ID #27 and SEQ ID #28;
   SEQ ID #15 and SEQ ID #34;
   SEQ ID #19 and SEQ ID #40;
   SEQ ID #21 and SEQ ID #22;
   SEQ ID #17 and SEQ ID #18;
   SEQ ID #25 and SEQ ID #38; and
   SEQ ID #23 and SEQ ID #41.

17. A method of determining fragment lengths of alleles present at a plurality of loci in a DNA-containing sample, comprising the steps of:
   a) obtaining a DNA-containing sample to be analyzed;
   b) amplifying by compound multiplex PCR a plurality of loci comprising FGA, vWA, TH01, TPOX, CSF1PO, D3S1358, D5S818, D7S820, D8S1179, D13S317, D16S539, D18S51, and D21S11, wherein said compound multiplex PCR is carried out using a plurality of primer pairs each of which is specific for one of said loci and wherein said step of amplifying produces a mixture of labeled amplicons, and
   c) analyzing by electrophoresis said mixture of labeled amplicons, wherein said step of analyzing allows the determination of said fragment lengths of alleles present at said plurality of loci in said DNA-containing sample, and wherein said plurality of primer pairs is
   SEQ ID #1 and SEQ ID #2;
   SEQ ID #3 and SEQ ID #4;
   SEQ ID #5 and SEQ ID #6;
   SEQ ID #30 and SEQ ID #31;
   SEQ ID #9 and SEQ ID #10;
   SEQ ID #11 and SEQ ID #12;
   SEQ ID #13 and SEQ ID #14;
   SEQ ID #27 and SEQ ID #28;
   SEQ ID #15 and SEQ ID #34;
   SEQ ID #19 and SEQ ID #40;
   SEQ ID #21 and SEQ ID #22;
   SEQ ID #17 and SEQ ID #18;
   SEQ ID #25 and SEQ ID #38; and
   SEQ ID #23 and SEQ ID #41.

18. The DNA sequence represented by SEQ ID #44.

19. A method for determining the lengths of amplicons produced by PCR amplification of locus D3S1358, comprising the steps of:
   a) obtaining a DNA-containing sample to be analyzed,
   b) amplifying by PCR the DNA sequence represented by SEQ ID #44 or a portion thereof, wherein said PCR is carried out using a primer pair which is specific for said DNA sequence represented by SEQ ID #44, at least one primer of each of said primer pairs being labeled with a detectable label, and wherein said step of amplifying produces a mixture of labeled amplicons, and
   c) analyzing said mixture of labeled amplicons, wherein said step of analyzing comprises a determination of the lengths of said amplicons.

20. The method of claim 19 wherein said step of analyzing is carried out in order to determine the lengths of the STR polymorphisms at locus D3S1358.

21. The DNA sequence represented by SEQ ID # 45.

22. A method for determining the lengths of amplicons produced by PCR amplification of locus D13S317, comprising the steps of:
  a) obtaining a DNA-containing sample to be analyzed,
  b) amplifying by PCR the DNA sequence represented by SEQ ID #45 or a portion thereof, wherein said PCR is carried out using a primer pair which is specific for said DNA sequence represented by SEQ ID #45, at least one primer of each of said primer pairs being labeled with a detectable label, and wherein said step of amplifying produces a mixture of labeled amplicons, and p1 c) analyzing said mixture of labeled amplicons, wherein said step of analyzing comprises a determination of the lengths of said amplicons.

23. The method of claim 22 wherein said step of analyzing is carried out in order to determine the lengths of the STR polymorphisms at locus D13S317.

24. An oligonucleotide having a nucleotide sequence selected from the group consisting of SEQ ID NO. 1, SEQ ID NO. 2, SEQ ID NO.3, SEQ ID NO.4, SEQ ID NO.5, SEQ ID NO.6, SEQ ID NO.7, SEQ ID NO.8, SEQ ID NO.9, SEQ ID NO.10, SEQ ID NO.11, SEQ ID NO.12, SEQ ID NO.13, SEQ ID NO.14, SEQ ID NO.15, SEQ ID NO.16, SEQ ID NO.17, SEQ ID NO.18, SEQ ID NO.19, SEQ ID NO.20, SEQ ID NO.21, SEQ ID NO.22, SEQ ID NO.23, SEQ ID NO.24, SEQ ID NO.25, SEQ ID NO.26, SEQ ID NO.27, SEQ ID NO.28, SEQ ID NO.29, SEQ ID NO.30, SEQ ID NO.31, SEQ ID NO.32, SEQ ID NO.33, SEQ ID NO.34, SEQ ID NO.35, SEQ ID NO.36, SEQ ID NO.37, SEQ ID NO.38, SEQ ID NO.39, SEQ ID NO.40, SEQ ID NO.41. SEQ ID NO.42, and SEQ ID NO.43, and variants of said sequences wherein the variants possess about 65% or greater homology to said sequences, and wherein said variants have sufficient complementarity to a complement sequence of said nucleotide sequence so as to be able to specifically hybridize with said complement sequence sufficiently well to permit primer extension by a polymerase enzyme.

* * * * *

SEQUENCE LISTING

```
<160> NUMBER OF SEQ ID NOS: 45

<210> SEQ ID NO 1
<211> LENGTH: 20
<212> TYPE: DNA
<213> ORGANISM: artificial sequence
<220> FEATURE:
<222> LOCATION: (1)..(20)
<223> OTHER INFORMATION: primer

<400> SEQUENCE: 1
gatgtgaaag ccctagtgga                                          20

<210> SEQ ID NO 2
<211> LENGTH: 23
<212> TYPE: DNA
<213> ORGANISM: artificial sequence
<220> FEATURE:
<222> LOCATION: (1)..(23)
<223> OTHER INFORMATION: primer

<400> SEQUENCE: 2
cataggatgg atggatagat gga                                      23

<210> SEQ ID NO 3
<211> LENGTH: 25
<212> TYPE: DNA
<213> ORGANISM: artificial sequence
<220> FEATURE:
<222> LOCATION: (1)..(25)
<223> OTHER INFORMATION: primer
```

```
<400> SEQUENCE: 3
aattccccaa gtgaattgcc ttcta                                              25

<210> SEQ ID NO 4
<211> LENGTH: 22
<212> TYPE: DNA
<213> ORGANISM: artificial sequence
<220> FEATURE:
<222> LOCATION: (1)..(22)
<223> OTHER INFORMATION: primer

<400> SEQUENCE: 4
tcaatgttct ccagagacag ac                                                 22

<210> SEQ ID NO 5
<211> LENGTH: 23
<212> TYPE: DNA
<213> ORGANISM: artificial sequence
<220> FEATURE:
<222> LOCATION: (1)..(23)
<223> OTHER INFORMATION: primer

<400> SEQUENCE: 5
ttcatgccac tgcacttcac tct                                                23

<210> SEQ ID NO 6
<211> LENGTH: 20
<212> TYPE: DNA
<213> ORGANISM: artificial sequence
<220> FEATURE:
<222> LOCATION: (1)..(20)
<223> OTHER INFORMATION: primer

<400> SEQUENCE: 6
ccgactacca gcaacaacac                                                    20

<210> SEQ ID NO 7
<211> LENGTH: 19
<212> TYPE: DNA
<213> ORGANISM: artificial sequence
<220> FEATURE:
<222> LOCATION: (1)..(19)
<223> OTHER INFORMATION: primer

<400> SEQUENCE: 7
actgcagtcc aatctgggt                                                     19

<210> SEQ ID NO 8
<211> LENGTH: 20
<212> TYPE: DNA
<213> ORGANISM: artificial sequence
<220> FEATURE:
<222> LOCATION: (1)..(20)
<223> OTHER INFORMATION: primer

<400> SEQUENCE: 8
atgaaatcaa cagaggcttg                                                    20

<210> SEQ ID NO 9
<211> LENGTH: 30
<212> TYPE: DNA
<213> ORGANISM: artificial sequence
<220> FEATURE:
<222> LOCATION: (1)..(30)
<223> OTHER INFORMATION: primer

<400> SEQUENCE: 9
```
atgtattttt gtatttcatg tgtacattcg         30

<210> SEQ ID NO 10
<211> LENGTH: 30
<212> TYPE: DNA
<213> ORGANISM: artificial sequence
<220> FEATURE:
<222> LOCATION: (1)..(30)
<223> OTHER INFORMATION: primer

<400> SEQUENCE: 10
cacgtagcta taattagttc attttcatca         30

<210> SEQ ID NO 11
<211> LENGTH: 23
<212> TYPE: DNA
<213> ORGANISM: artificial sequence
<220> FEATURE:
<222> LOCATION: (1)..(23)
<223> OTHER INFORMATION: primer

<400> SEQUENCE: 11
tgtacaagtg ccagatgctc gtt                23

<210> SEQ ID NO 12
<211> LENGTH: 26
<212> TYPE: DNA
<213> ORGANISM: artificial sequence
<220> FEATURE:
<222> LOCATION: (1)..(26)
<223> OTHER INFORMATION: primer

<400> SEQUENCE: 12
ccatttacgt ttgtgtgtgc atctgt             26

<210> SEQ ID NO 13
<211> LENGTH: 24
<212> TYPE: DNA
<213> ORGANISM: artificial sequence
<220> FEATURE:
<222> LOCATION: (1)..(24)
<223> OTHER INFORMATION: primer

<400> SEQUENCE: 13
ctgtgtctca gttttcctac ctgt               24

<210> SEQ ID NO 14
<211> LENGTH: 24
<212> TYPE: DNA
<213> ORGANISM: artificial sequence
<220> FEATURE:
<222> LOCATION: (1)..(24)
<223> OTHER INFORMATION: primer

<400> SEQUENCE: 14
tggaggtcat ccttatctcc tttc               24

<210> SEQ ID NO 15
<211> LENGTH: 25
<212> TYPE: DNA
<213> ORGANISM: artificial sequence
<220> FEATURE:
<222> LOCATION: (1)..(25)
<223> OTHER INFORMATION: primer

<400> SEQUENCE: 15
gacaagggtg attttcctct ttggt                                          25

<210> SEQ ID NO 16
<211> LENGTH: 22
<212> TYPE: DNA
<213> ORGANISM: artificial sequence
<220> FEATURE:
<222> LOCATION: (1)..(22)
<223> OTHER INFORMATION: primer

<400> SEQUENCE: 16
gtgattccaa tcatagccac ag                                             22

<210> SEQ ID NO 17
<211> LENGTH: 26
<212> TYPE: DNA
<213> ORGANISM: artificial sequence
<220> FEATURE:
<222> LOCATION: (1)..(26)
<223> OTHER INFORMATION: primer

<400> SEQUENCE: 17
aggctgacta tggagttatt ttaagg                                         26

<210> SEQ ID NO 18
<211> LENGTH: 24
<212> TYPE: DNA
<213> ORGANISM: artificial sequence
<220> FEATURE:
<222> LOCATION: (1)..(24)
<223> OTHER INFORMATION: primer

<400> SEQUENCE: 18
ttatcctcat tgacagaatt gcac                                           24

<210> SEQ ID NO 19
<211> LENGTH: 24
<212> TYPE: DNA
<213> ORGANISM: artificial sequence
<220> FEATURE:
<222> LOCATION: (1)..(24)
<223> OTHER INFORMATION: primer

<400> SEQUENCE: 19
gcagggcata acattatcca aaag                                           24

<210> SEQ ID NO 20
<211> LENGTH: 22
<212> TYPE: DNA
<213> ORGANISM: artificial sequence
<220> FEATURE:
<222> LOCATION: (1)..(22)
<223> OTHER INFORMATION: primer

<400> SEQUENCE: 20
gatcctctga cactcggttg ta                                             22

<210> SEQ ID NO 21
<211> LENGTH: 21
<212> TYPE: DNA
<213> ORGANISM: artificial sequence
<220> FEATURE:
<222> LOCATION: (1)..(21)
<223> OTHER INFORMATION: primer

<400> SEQUENCE: 21
tctgacccat ctaacgccta t                                              21

<210> SEQ ID NO 22
<211> LENGTH: 23
<212> TYPE: DNA
<213> ORGANISM: artificial sequence
<220> FEATURE:
<222> LOCATION: (1)..(23)
<223> OTHER INFORMATION: primer

<400> SEQUENCE: 22
gcccaaaaag acagacagaa aga                         23

<210> SEQ ID NO 23
<211> LENGTH: 25
<212> TYPE: DNA
<213> ORGANISM: artificial sequence
<220> FEATURE:
<222> LOCATION: (1)..(25)
<223> OTHER INFORMATION: primer

<400> SEQUENCE: 23
ggcaaatagg gggcaaaatt caaag                       25

<210> SEQ ID NO 24
<211> LENGTH: 21
<212> TYPE: DNA
<213> ORGANISM: artificial sequence
<220> FEATURE:
<222> LOCATION: (1)..(21)
<223> OTHER INFORMATION: primer

<400> SEQUENCE: 24
gaaaagctcc cgattatcca g                           21

<210> SEQ ID NO 25
<211> LENGTH: 23
<212> TYPE: DNA
<213> ORGANISM: artificial sequence
<220> FEATURE:
<222> LOCATION: (1)..(23)
<223> OTHER INFORMATION: primer

<400> SEQUENCE: 25
cttcctctgc ttcactttc acc                          23

<210> SEQ ID NO 26
<211> LENGTH: 23
<212> TYPE: DNA
<213> ORGANISM: artificial sequence
<220> FEATURE:
<222> LOCATION: (1)..(23)
<223> OTHER INFORMATION: primer

<400> SEQUENCE: 26
ccttctgtcc ttgtcagcgt tta                         23

<210> SEQ ID NO 27
<211> LENGTH: 23
<212> TYPE: DNA
<213> ORGANISM: artificial sequence
<220> FEATURE:
<222> LOCATION: (1)..(23)
<223> OTHER INFORMATION: primer

<400> SEQUENCE: 27
cctgggctct gtaaagaata gtg                         23

-continued

<210> SEQ ID NO 28
<211> LENGTH: 24
<212> TYPE: DNA
<213> ORGANISM: artificial sequence
<220> FEATURE:
<222> LOCATION: (1)..(24)
<223> OTHER INFORMATION: primer

<400> SEQUENCE: 28
atcagagctt aaactgggaa gctg                                          24

<210> SEQ ID NO 29
<211> LENGTH: 28
<212> TYPE: DNA
<213> ORGANISM: artificial sequence
<220> FEATURE:
<222> LOCATION: (1)..(28)
<223> OTHER INFORMATION: primer

<400> SEQUENCE: 29
tattagtcaa tgttctccag agacagac                                      28

<210> SEQ ID NO 30
<211> LENGTH: 21
<212> TYPE: DNA
<213> ORGANISM: artificial sequence
<220> FEATURE:
<222> LOCATION: (1)..(21)
<223> OTHER INFORMATION: primer

<400> SEQUENCE: 30
tgcagtccaa tctgggtgac a                                             21

<210> SEQ ID NO 31
<211> LENGTH: 24
<212> TYPE: DNA
<213> ORGANISM: artificial sequence
<220> FEATURE:
<222> LOCATION: (1)..(24)
<223> OTHER INFORMATION: primer

<400> SEQUENCE: 31
tgaaatcaac agaggcttgc atgt                                          24

<210> SEQ ID NO 32
<211> LENGTH: 24
<212> TYPE: DNA
<213> ORGANISM: artificial sequence
<220> FEATURE:
<222> LOCATION: (1)..(24)
<223> OTHER INFORMATION: primer

<400> SEQUENCE: 32
atgccccata ggttttgaac tcac                                          24

<210> SEQ ID NO 33
<211> LENGTH: 21
<212> TYPE: DNA
<213> ORGANISM: artificial sequence
<220> FEATURE:
<222> LOCATION: (1)..(21)
<223> OTHER INFORMATION: primer

<400> SEQUENCE: 33
tctcagatcc tctgacactc g                                             21

-continued

```
<210> SEQ ID NO 34
<211> LENGTH: 25
<212> TYPE: DNA
<213> ORGANISM: artificial sequence
<220> FEATURE:
<222> LOCATION: (1)..(25)
<223> OTHER INFORMATION: primer

<400> SEQUENCE: 34
caagtgattc caatcatagc cacag                                  25

<210> SEQ ID NO 35
<211> LENGTH: 23
<212> TYPE: DNA
<213> ORGANISM: artificial sequence
<220> FEATURE:
<222> LOCATION: (1)..(23)
<223> OTHER INFORMATION: primer

<400> SEQUENCE: 35
ctgaaaagct cccgattatc cag                                    23

<210> SEQ ID NO 36
<211> LENGTH: 22
<212> TYPE: DNA
<213> ORGANISM: artificial sequence
<220> FEATURE:
<222> LOCATION: (1)..(22)
<223> OTHER INFORMATION: primer

<400> SEQUENCE: 36
tccccaagtg aattgccttc ta                                     22

<210> SEQ ID NO 37
<211> LENGTH: 24
<212> TYPE: DNA
<213> ORGANISM: artificial sequence
<220> FEATURE:
<222> LOCATION: (1)..(24)
<223> OTHER INFORMATION: primer

<400> SEQUENCE: 37
aaacccgact accagcaaca acac                                   24

<210> SEQ ID NO 38
<211> LENGTH: 19
<212> TYPE: DNA
<213> ORGANISM: artificial sequence
<220> FEATURE:
<222> LOCATION: (1)..(19)
<223> OTHER INFORMATION: primer

<400> SEQUENCE: 38
gctaggccct tctgtcctt                                         19

<210> SEQ ID NO 39
<211> LENGTH: 25
<212> TYPE: DNA
<213> ORGANISM: artificial sequence
<220> FEATURE:
<222> LOCATION: (1)..(25)
<223> OTHER INFORMATION: primer

<400> SEQUENCE: 39
caaatcttac taccagcaac aacac                                  25

<210> SEQ ID NO 40
```

```
<211> LENGTH: 25
<212> TYPE: DNA
<213> ORGANISM: artificial sequence
<220> FEATURE:
<222> LOCATION: (1)..(25)
<223> OTHER INFORMATION: primer

<400> SEQUENCE: 40
ctgctgagtg atttgtctgt aattg                                          25

<210> SEQ ID NO 41
<211> LENGTH: 27
<212> TYPE: DNA
<213> ORGANISM: artificial sequence
<220> FEATURE:
<222> LOCATION: (1)..(27)
<223> OTHER INFORMATION: primer

<400> SEQUENCE: 41
tcacaccaca tttcaatcaa ggtccat                                        27

<210> SEQ ID NO 42
<211> LENGTH: 25
<212> TYPE: DNA
<213> ORGANISM: artificial sequence
<220> FEATURE:
<222> LOCATION: (1)..(25)
<223> OTHER INFORMATION: primer

<400> SEQUENCE: 42
tgctggacat ggtatcacag aagtc                                          25

<210> SEQ ID NO 43
<211> LENGTH: 25
<212> TYPE: DNA
<213> ORGANISM: artificial sequence
<220> FEATURE:
<222> LOCATION: (1)..(25)
<223> OTHER INFORMATION: primer

<400> SEQUENCE: 43
ttcagagagc ttgaattgtt ggtca                                          25

<210> SEQ ID NO 44
<211> LENGTH: 131
<212> TYPE: DNA
<213> ORGANISM: Homo sapiens
<220> FEATURE:
<221> NAME/KEY:
<222> LOCATION: (1)..(131)
<223> OTHER INFORMATION: Allele

<400> SEQUENCE: 44
actgcagtcc aatctgggtg acagagcaag accctgtctc atagatagat agatagatag    60
atagatagat agatagatag atagatagat agacagacag atagatacat gcaagcctct   120
gttgatttca t                                                        131

<210> SEQ ID NO 45
<211> LENGTH: 249
<212> TYPE: DNA
<213> ORGANISM: Homo sapiens
<220> FEATURE:
<221> NAME/KEY: Allele
<222> LOCATION: (1)..(249)

<400> SEQUENCE: 45
```

-continued

```
tgctggacat ggtatcacag aagtctggga tgtggaggag agttcatttc tttagtgggc      60
atccgtgact ctctggactc tgacccatct aacgcctatc tgtatttaca aatacattat     120
ctatctatct atctatctat ctatctatca atcaatcatc tatctatctt tctgtctgtc     180
tttttgggct gcctatggct caacccaagt tgaaggagga gatttgacca acaattcaag     240
ctctctgaa                                                             249
```